(12) United States Patent
Spits et al.

(10) Patent No.: US 7,964,406 B2
(45) Date of Patent: Jun. 21, 2011

(54) MEANS AND METHODS FOR PRODUCING A STABILIZED CELL OF INTEREST

(75) Inventors: Hergen Spits, San Francisco, CA (US); Benjamin Berkhout, Naarden (NL); Jurgen E. Seppen, Naarden (NL); David M. Markusic, Amsterdam (NL); Kees Weijer, Amsterdam (NL)

(73) Assignee: Academisch Medisch Centrum Bij De Universiteit Van Amsterdam, Amsterdam (NL)

( * ) Notice: Subject to any disclaimer, the term of this patent is extended or adjusted under 35 U.S.C. 154(b) by 0 days.

(21) Appl. No.: 11/659,921

(22) PCT Filed: Aug. 10, 2005

(86) PCT No.: PCT/NL2005/000581
§ 371 (c)(1),
(2), (4) Date: Aug. 2, 2007

(87) PCT Pub. No.: WO2006/016808
PCT Pub. Date: Feb. 16, 2006

(65) Prior Publication Data
US 2007/0289029 A1 Dec. 13, 2007

Related U.S. Application Data

(60) Provisional application No. 60/600,465, filed on Aug. 10, 2004.

(30) Foreign Application Priority Data

Aug. 10, 2004 (EP) .................................. 04077262

(51) Int. Cl.
*C12N 15/63* (2006.01)
*C12N 15/06* (2006.01)
*C12N 5/08* (2006.01)
(52) U.S. Cl. .................. 435/455; 435/326; 435/372
(58) Field of Classification Search .................. None
See application file for complete search history.

(56) References Cited

U.S. PATENT DOCUMENTS

| 4,997,764 | A | | 3/1991 | Dalla Favera |
| 5,684,147 | A | | 11/1997 | Agrawal et al. |
| 5,849,900 | A | | 12/1998 | Moelling |
| 5,866,757 | A | * | 2/1999 | Reisner .......................... 800/8 |
| 6,001,558 | A | | 12/1999 | Backus et al. |
| 2003/0152559 | A1 | | 8/2003 | Yang et al. |
| 2003/0158131 | A1 | | 8/2003 | Aldovini |
| 2005/0009180 | A1 | | 1/2005 | Yang et al. |
| 2005/0238626 | A1 | | 10/2005 | Yang et al. |

FOREIGN PATENT DOCUMENTS

| EP | 1 627 563 | 2/2006 |
| GB | 2 398 783 | 9/2004 |
| WO | WO 89/08146 | 9/1989 |
| WO | WO 94/08004 | 4/1994 |
| WO | WO 94/17086 | 8/1994 |
| WO | WO 95/06409 | 3/1995 |
| WO | WO 96/01313 | 1/1996 |
| WO | WO 01/20013 | 3/2001 |
| WO | WO 03/050262 | 6/2003 |
| WO | WO 03/052083 | 6/2003 |
| WO | WO 03/052083 A | 6/2003 |
| WO | WO 03/070193 | 8/2003 |
| WO | WO 03/079757 | 10/2003 |
| WO | WO 2005/052164 | 6/2005 |
| WO | WO 2005/102383 | 11/2005 |
| WO | WO 2006/132524 | 12/2006 |
| WO | WO 2007/058527 | 5/2007 |

OTHER PUBLICATIONS

Weijer et al., Blood, 2002, V.99 pp. 2752-2759).*
Kyba et al., PNAS, 2003, V.100, pp. 1-12.*
Database Biosis [Online], Biosciences Information Service, Philadelphia, PA, US; Nov. 16, 2003, Schuringa Jan Jacob et al: "Constitutive activation of STAT5A promotes human hematopoietic stem cell self-renewal and erythroid differentiation." XP002317908, Database accession No. PREV200400133695 abstract, & Blood, vol. 102, No. 11, Nov. 16, 2003, p. 330a, 45th Annual Meeting of the American Society of Hematology; San Diego, CA, USA; Dec. 6-9, 2003, ISSN: 0006-4971.
Database Biosis [Online], Biosciences Information Service, Philadelphia, PA, US, Nov. 16, 2003, Schuringa Jan Jacob et al: "Enforced activation of STAT5A facilitates ES-derived hematopoietic differentiation and reconstitutes hematopoiesis in vivo." XP002317909, Database accession No. PREV200400172604 abstract & Blood, vol. 102, No. 11, Nov. 16, 2003, p. 167a, 45th Annual Meeting of the American Society of Hematology; San Diego, CA, USA; Dec. 6-9, 2003, ISSN: 0006-4971.
Kobayashi Naoya et al: "Prevention of acute liver failure in rats with reversibly immoralized human hepatocytes" Science (Washington D C), vol. 287, No. 5456, Feb. 18, 2000, pp. 1258-1262, XP002159501, ISSN: 0036-8075, the whole document.
Das Atze T et al: "Viral evolution as a tool to improve the tetracycline-regulated gene expression system." The Journal of Biological Chemistry, Apr. 30, 2004, vol. 279, No. 18, Apr. 30, 2004, pp. 18776-18782, XP002317903, ISSN: 0021-9258, cited in the application, figures 1A,3.
Taggiai Elisabetta et al: "Development of a human adaptive immune system in cord blood cell-transplanted mice" Science (Washington D C), vol. 304, No. 5667, Apr. 2, 2004, pp. 104-107, XP002356076, ISSN: 0036-8075, the whole document.
Goldman J P et al: "Enhanced human cell engraftment in mice deficient in RAG2 and the common cytokine receptor gamma chain" British Journal of Haematology, Oxford, GB, vol. 103, No. 2, Nov. 1998, pp. 335-342, XP002249529; ISSN: 0007-1048, the whole document.

(Continued)

*Primary Examiner* — Michail A Belyavskyi
(74) *Attorney, Agent, or Firm* — TraskBritt, P.C.

(57) ABSTRACT

The invention provides a method for producing a stabilized cell of interest, said method comprising providing a stem cell and/or a precursor cell of said cell of interest with a nucleic acid sequence which, when present in said cell of interest, is capable of stabilizing said cell of interest, providing a non-human animal with said stem cell and/or precursor cell, allowing generation of said cell of interest in said animal, and obtaining said cell of interest. Said animal is preferably provided with a human stem cell and/or human precursor cell, allowing production of a human cell line.

6 Claims, 23 Drawing Sheets

OTHER PUBLICATIONS

Mulloy James C et al: "Maintaining the self-renewal and differentiation potential of human CD34+ hematopoietic cells using a single genetic element."Blood, vol. 102, No. 13, Dec. 15, 2003, pp. 4369-4376, XP002317905, ISSN: 0006-4971, p. 4374. left-hand column, last paragraph.

Stier Sebastian et al: "Notch1 activation increases hematopoietic stem cell self-renewal in vivo and favors lymphoid over myeloid lineage outcome," Blood, vol. 99, No. 7, Apr. 1, 2002, pp. 2369-2378, XP002317904, ISSN: 0006-4971, p. 2375, left-hand column.

Gimeno R et al: "Monitoring the effect of gene silencing by RNA interference in human CD34<+> cells injected into newborn RAG2<-/-> [gamma]c <-/-> mice: Functional inactivation of p53 in developing T cells" Blood Dec. 15, 2004 United States, vol. 104, No. 13, Dec. 15, 2004, pp. 3886-3893, XP002317351, ISSN: 0006-4971, the whole document.

Schuringa Jan Jacob et al: "Constitutive activation of STAT5A promotes human hematopoietic stem cell self-renewal and erythroid differentiation" Journal of Experimental Medicine, vol. 200, No. 5, Sep. 6, 2004, pp. 623-635, XP002317907, ISSN: 0022-1007.

Office Action for U.S. Appl. No. 10/097,542 dated Feb. 9, 2009.

Office Action for U.S. Appl. No. 11/665,510 dated Mar. 11, 2009.

U.S. Appl. No. 10/097,542, filed Mar. 8, 2002, Berkhout et al., Viral Replicons and Viruses Dependent on Inducing Agents.

U.S. Appl. No. 11/665,510, filed Jun. 20, 2007, Berkhout et al., Nucleic Acids Against Viruses, in Particular HIV.

U.S. Appl. No. 11/921,925, filed Apr. 15, 2009, Hergen Spits, Means and Methods for Generating a T Cell Against an Antigen of Interest.

U.S. Appl. No. 12/085,107, filed May 16, 2008, Berkhout et al., Inducible Expression Systems.

U.S. Appl. No. 12/086,269, filed Jun. 6, 2008, Hergen Spits, Means and Methods for Influencing the Stability of Cells.

U.S. Appl. No. 12/086,328, filed Apr. 6, 2009, Spits et al., Means and Methods for Influencing the Stability of Antibody Producing Cells.

Alajez, et al., Therapeutic potential of a tumor-specific, MHC-unrestricted T-cell receptor expressed on effector cells of the innate and the adaptive immune system through bone marrow transduction and immune reconstitution: Blood, Jun. 15, 2005, vol. 105, No. 12; pp. 4583-4589.

Chlewicki, et al., High-affinity, Peptide-specific T Cell Receptors can be Generated by Mutations in CDR1, CDR2 or CDR3; J. Mol. Biol.; 2005; 346, 223-239.

Clay, et al., Efficient Transfer of a Tumor Antigen-Reactive TCR to Human Peripheral Blood Lymphocytes Confers Anti-Tumor Reactivity, Journal of Immunology, 1999, pp. 507-513, vol. 163, The Williams and Wilkins Co. Baltimore, MD, US.

Clay, e t al. Potential Use of T Cell Receptor Genese to Modify Hematopoietic Stem Cells for the Gene Therapy of Cancer, Pathology Oncology Research, 1999, pp. 3-15, vol. 5, No. 1, Budapest, Hungary.

Das, et al., Abstract, A Conditionally Replicating Virus as a Novel Approach Toward an HIV Vaccine, Methods in Enzymology, 2004, pp. 359-379, vol. 388, Academic Press, San Diego, US.

Gossen, et al., Abstract, Transcriptional Activation by Tetracyclines in Mammalian Cells, Science, Jun. 23, 1995, pp. 1766-1769, vol. 268, American Association for the Advancement of Science, US.

Kang, et al. Long-term expression of a T-cell receptor beta-chain gene in mice reconstituted with retrovirus-infected hematopoietic stem cells, Proc. Natl. Acad. Sci., Dec. 1990, pp. 9803-9807, vol. 87, National Academy of Science, Washington, DC, US.

Knodel, et al., Abstract, Blimp-1 over-expression abrogates IL-4-and CD40-mediated suppression of terminal B cell differentiation but arrests isotype switching, European Journal of Immunology, 2001, pp. 1972-1980, vol. 31, No. 7.

Knott, et al., Tetracycline-dependent Gene Regulation: Combinations of Transregulators Yield of a Variety of Expression Windows, Biotechniques, 2002, pp. 796-806, vol. 32, No. 4; Informs Life Sciences Publishing, Westborough, MA, US.

Krueger, et al., Single-chain Tet Transregulators, Nucleic Acids Research Jun. 15, 2003, pp. 3050-3056, vol. 31, No. 12 Oxford University Press, Surrey, GB.

Mathas, et al., Abstract, Intrinsic inhibition of transcription factor E2A by HLH proteins ABF-1 and Id2 mediates reprogramming of neoplastic B cells in Hodgkin lymphoma, Nature Immunology, Feb. 2006, pp. 207-215, vol. 7, No. 2.

Mehta, et al., IL-21 induces the apoptosis of resting and activated primary B cells, Journal of Immunology, Apr. 15, 2003, pp. 4111-4118, vol. 170, No. 8, The Williams and Wilkins Co., Baltimore, US.

Ozaki, et al., Regulation of B cell differentiation and plasma cell generation by IL-21, a novel inducer of Blimp-1 and Bcl-6, Journal of Immunology, Nov. 1, 2004, pp. 5361-5371, vol. 173, No. 9.

PCT International Search Report, PCT.NL2006/00625, dated Apr. 10, 2007.

PCT International Search Report, PCT/NL2005/000739, dated Nov. 29, 2006.

PCT International Search Report, PCT/NL2005/000848, dated Jul. 10, 2006.

PCT International Search Report, PCT/NL2006/000277, dated Sep. 1, 2006.

PCT International Search Report, PCT/NL2006/000575, dated Jul. 27, 2007.

Petrie, et al., T Cell Receptor Gene Recombination Patterns, and Mechanisms: Cell Death, Rescue, and T Cell Production, J Exp Med 1995; 182: 121-7.

Salucci, et al., Tight control of gene expression by a helper-dependent adenovirus vector carrying the rtTA2S-M2 tetracycline transactivator and repressor systems, Gene Therapy, 2002, pp. 1415-1421, vol. 9, Macmillam Press Ltd., Basingstoke, GB.

Schvarts, et al., A senescence rescue screen identifies BCL6 as an inhibitor of anti-proliferative p19ARF-p53 signaling, Genes and Development, Mar. 15, 2002, pp. 681-686, vol. 16, No. 6.

Shaffer, et al., Blimp-1 orchestrates plasma cell differentiation by extinguishing the mature B cell gene expression program, Immunity, Jul. 2002, pp. 51-62, vol. 17, No. 1.

Shapiro-Shelef, et al., Blimp-1 is required for maintenance of long-lived plasma cells in the bone marrow, The Journal of Experimental Medicine, Dec. 5, 2005, pp. 1471-1476, vol. 202, No. 11.

Shen Chun-Pyn, et al., B-cell-specific DNA binding by an E47 homodimer, Molecular and Cellular Biology, 1995, pp. 4518-4524, vol. 15, No. 8.

Traggiai, et al., Abstract: An efficient method to make human monoclonal antibodies from memory B cells: potent neutralization of SARS conoranavirus, Nature Medicine, Aug. 2004, pp. 871-875, vol. 10, No. 8.

Urlinger, et al., Exploring the sequence space for the tetracycline-dependent transcriptional activators: novel mutations yield expanded range and sensitivity, Proceedings of the National Academy of Sciences of USA, pp. 7963-7968, Jul. 5, 2000, vol. 97, No. 14, National Academy of Science, Washington, DC, US.

Vickers, et al., Efficient reduction of target RNAs by small interfering RNA and RNase H-dependent antisense agents, 2003, The Journal of Biological Chemistry, vol. 278, pp. 7108-7118.

Yamochi, et al. Adenovirus-mediated high expression of BCL-6 CV-1 cells induces apoptotic cell death accompanied by down-regulation of BCL-2 and BCL-XL, Oncogene, Jan. 14, 1999, pp. 487-494, vol. 18, No. 2.

Yang, et al. Generation of Functional antigen-specific T Cells in defined genetic backgrounds by retrovirus-mediated expression of TCR cDNAs in hematopoietic precursor cells, Proceedings of the National Academy of Sciences of USA, Apr. 30, 2002. pp. 6204-6209, vol. 99, No. 9, National Academy of Science, Washington, DC, US.

Yang, et al., Long-term in vivo provision of antigen-specific T cell immunity by programming hematopoietic stem cells, Proceedings of the National Academy of Sciences of USA, Mar. 22, 2005, pp. 4518-4523, vol. 102, National Academy of Science, Washington, DC, US.

Zhou, et al., Improved single-chain transactivators of the Tet-On gene expression system, Biotechnology, 2007, p. 6, vol. 7.

Zhou, et al., Modification of the Tet-On regulatory system prevents the conditional-live HIV-1 variant from losing doxycycline-control, Retrovirology, 2006, p. 82, vol. 3.

Zhou, et al., Optimization of the Tet-On system for regulated gene expression through viral evolution, Gene Therapy, Oct. 2006, pp. 1382-1390, vol. 13, No. 19.

* cited by examiner

A

B

Vβ

A

B

MEANS AND METHODS FOR PRODUCING A STABILIZED CELL OF INTEREST

CROSS-REFERENCE TO RELATED APPLICATION

This application is the national phase of PCT/NL2005/000581, filed Aug. 10, 2005, designating the United States, and published, in English, on Feb. 16, 2006, as WO 2006/016808 A2, and claims the benefit, under 35 U.S.C. §119(e) of U.S. Provisional Patent Application 60/600,465 filed on Aug. 10, 2004.

BACKGROUND OF THE INVENTION

The invention relates to the field of cell biology. More particularly the invention relates to the production of stabilized cells.

DETAILED DESCRIPTION OF THE INVENTION

Figure 1:
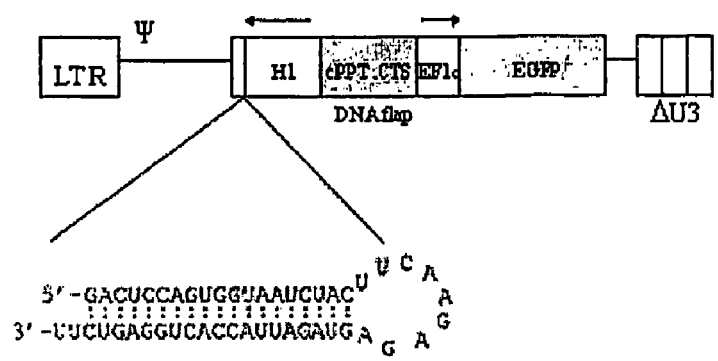
FIG. 1. p53 knock-down in human hematopoietic precursors. (A) Schematic representation of the lentiviral RNA interference vector pTRIPΔU3-EF1alpha p53. The predicted short hairpin RNA targeting the human p53 is shown. (B) Human hematopoietic progenitors (CD34$^+$) were isolated and transduced with the lentiviral vector pTRIPΔU3-EF1alpha p53, after 1 week in culture with cytokines sorted based on the expression of GFP. Cells were then gamma irradiated and six hours later whole-cell extracts were prepared, separated on 10% SDS-polyacrylamide gel electrophoresis and immunoblotted to detect human p53. The blot was reprobed with an antibody against beta actin as a loading control.
Figure 1:
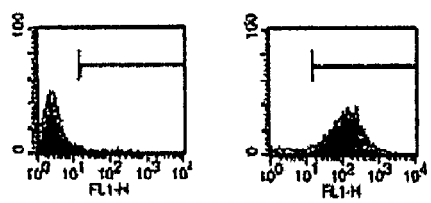
Figure 1:
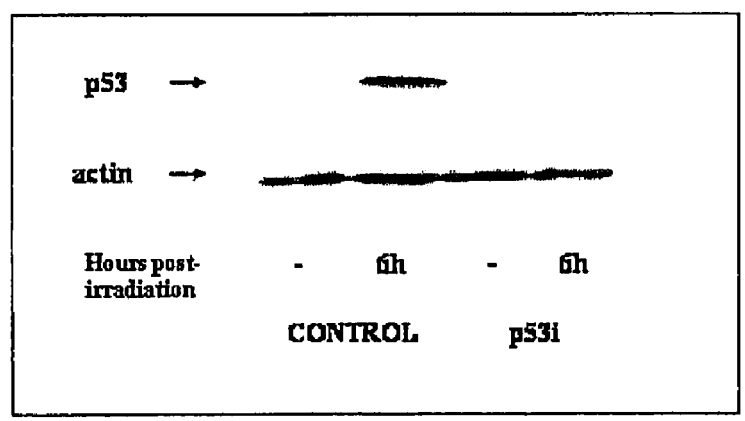

Ex vivo production of cells has been explored for a wide variety of applications. Cells of a sample obtained from an individual are, for instance, further cultured ex vivo for diagnostic purposes. Cultured cells are also used for (medical) testing, for instance to establish (beneficial) effects of candidate drug compounds. Moreover, cells are often cultured in order to harvest products secreted by said cells, such as enzymes, hormones and/or antibodies.

Production of monoclonal antibodies (mAbs) is an important application. Monoclonal antibodies represent multiple identical copies of a single antibody molecule that bind to antigens with the same affinity and promote the same effector functions. Monoclonal antibodies react with the same epitope on an antigen.

Amongst the benefits of mAbs is their ability to target specific cells or chemical mediators that could be involved in disease causation. This specificity confers certain clinical advantages on mAbs over more conventional treatments while offering patients an effective, well-tolerated therapy option with generally low side effects.

Monoclonal antibodies are, for instance, produced by fusing B cells, obtained from a test animal such as a mouse that has been immunized with a particular antigen, to (mouse) cancer cells in order to make hybridoma cells. The B cells confer antibody production capability, while the cancer cells enable hybridomas to divide indefinitely and grow well in cell-culture. Individual hybridomas producing the desired antibody from a single lymphocyte can then be selected for large-scale culture and mAb production.

Mouse mAbs are of limited therapeutic use in humans because immune responses are evoked. Mouse mAbs therefore do not provide long-term therapeutic benefits. This anti-mouse immune response also causes undesired side-effects. Furthermore, mouse mAbs cannot efficiently activate other important human immune-system components.

Therefore, efforts have been undertaken to make mAbs appear more human. One approach has been to engineer mouse/human-hybrid antibodies that still bind antigen, but are less likely to provoke an immune response.

Gene regions that exclusively make the mouse CDR have been isolated, and spliced into the human antibody gene regions required to complete a functional antibody molecule. These CDR-grafted antibodies are more than 90% human. Alternatively, mice carrying human Ig genes have been produced.

Another approach is the production of a phage display library by incorporating genes for human antibody variable regions (V genes) into the genes of a bacteriophage so that phages carry different human V genes. The altered phage genes direct phage-infected bacteria to make the corresponding human antibody fragments, which are automatically incorporated onto the viral surface.

In order to directly obtain human monoclonal antibodies with a desired specificity it would be convenient to isolate a B cell capable of producing such antibody and to culture the B cell ex vivo. However, hybridoma technology with human B cells has not been very successful because the resulting hybridomas are unstable. Many attempts for ex vivo culturing of B cells have been undertaken. It is well documented that human naïve and memory B cells can be cultured for a limited period following engagement of CD40 in the presence of cytokines, including IL-2, IL-4 and IL-10 (Arpin et al., 1995; Banchereau et al., 1991) and it is believed that this system mimics the in vivo response of B cells towards cognate antigen primed CD40L-expressing helper T cells. In the absence of CD40 ligation, IL-10 alone or in combination with IL-2 induces differentiation into antibody-producing cells (Arpin et al., 1997; Malisan et al., 1996). The mechanisms of regulation of survival and proliferation of mature B cells cultured under these conditions are only partly known.

Engagement of CD40 on B cells has multiple effects including protection against apoptosis, (partial) inhibition of differentiation and induction of cytokine responsiveness by B cells (Foy et al., 1996). Expression of a large number of cell cycle inhibitors were decreased by CD40 engagement including Rb-1 and Rb-2 (Dadgostar et al., 2002), and it is likely that down regulation of such genes release resting B cells from quiescence. Although CD40 triggering leads to a brief proliferative response, cytokines are instrumental in sustaining cell cycle progression of the triggered B cells. IL-2 and IL-4 are the most efficient cytokines that promote continued cell cycle progression of CD40 or surface Ig-stimulated B cells. B cell cultures described in the above mentioned papers are only stable during a limited period.

Another approach for immortalizing B cells is Epstein-Barr virus transformation. Although many attempts have failed, Traggiai et al. have reported a method for Epstein-Barr virus transformation of human B cells, which cells were obtained from a patient who recovered from severe acute respiratory syndrome coronavirus (SARS-CoV) infection. Monoclonal antibodies specific for different viral proteins were isolated (Traggiai et al., 2004).

Yet another approach for immortalizing B cells is described in patent application WO 03/052083. This application describes a method of stabilizing B cells wherein human B cells are isolated from a transgene mouse, after which the cells are transduced with constitutively active signal transducer of activation and transcription (CA-STAT). A prolonged life span of the B cells was observed. However, transduction efficiencies are low (between 5 and 20%). This means that many B cells capable of producing antibodies specifically binding a certain antigen need to be isolated in order to perform a transduction with a reasonable chance of success. A high amount of B cells that produce antibodies against one specific antigen is often unavailable.

Another disadvantage of most prior art methods is that it is often not possible to obtain human B cells capable of producing antibodies against any desired antigen. For instance, human B cells against autoantigens such as cytokines (for example Interleukin-10 and TNF-alpha), and antigens expressed on tissues (for example pancreas and skin) or a non tumor-specific part of a tumor (for example antigens that are expressed on malignant melanoma but also on normal melanocytes) are difficult to obtain. Furthermore, a human is of course not immunized with a desired antigen, such as a pathogen.

It is an object of the present invention to provide a method for producing a stabilized cell of interest. It is a further object to provide a method for producing a human B cell line, capable of producing antibodies against an antigen of interest.

In one aspect, the invention provides a method for producing a stabilized cell of interest, said method comprising:

providing a stem cell and/or a precursor cell of said cell of interest with a nucleic acid sequence which, when present in said cell of interest, is capable of stabilizing said cell of interest;

providing a non-human animal with said stem cell and/or precursor cell;

allowing generation of said cell of interest in said animal; and obtaining said cell of interest.

Preferably, said non-human animal is provided with said stem cell and/or progenitor cell after said stem cell and/or progenitor cell has been provided with said stabilizing nucleic acid sequence. In one embodiment however a stem cell and/or progenitor cell that is already present in a non-human animal is provided with said stabilizing nucleic acid.

Although prior art methods focus on immortalizing a cell of interest after it has been isolated, the present invention provides the insight that it is possible to generate a stabilized cell of interest by genetically altering a stem cell or precursor cell of said cell of interest. According to the invention a stabilized cell of interest is obtained when a stem cell and/or precursor cell is transduced with a nucleic acid sequence capable of stabilizing said cell of interest. Preferably, expression and/or activity of said nucleic acid is capable of being switched on or off. This is, for instance, performed by placing said nucleic acid sequence under control of an inducible promotor and/or by fusing said nucleic acid to an inactivating agent. After said transduced stem cell and/or precursor cell has been administered to a non-human animal, said stem cell and/or precursor cell is still capable of differentiating into a stabilized cell of interest. It would be expected that transduction of a stem cell or a precursor cell with an immortalizing nucleic acid sequence would result in an immortalized stem cell or precursor cell which continues replicating without differentiating. According to the present invention, a stem cell or precursor cell provided with an immortalizing nucleic acid sequence is still capable of differentiating into a stabilized cell of interest. Said stabilized cell of interest is preferably less sensitive to growth arrest stimuli and/or apoptotic stimuli as compared to the same kind of cell that has not been stabilized. In one embodiment, said stabilized cell of interest has a prolonged replication life span.

Said nucleic acid sequence is preferably in an inactive state under natural circumstances. In one embodiment a stem cell or precursor cell of a cell of interest comprising an immortalizing nucleic acid sequence differentiates into a cell of interest, whereas the resulting cell of interest in turn does not rapidly differentiate into a replication-deficient differentiated cell when said immortalizing nucleic acid sequence is activated. Instead, the resulting cell of interest is capable of continuing replication. Said cell of interest is harvested from said animal and preferably further cultured ex vivo, for instance, producing a cell line. Hence, transduction of a stem cell and/or precursor cell with an immortalizing nucleic acid sequence of the invention does not prevent said stem cells and/or precursor cells from differentiating. The resulting cells of interest are preferably less sensitive to growth arrest stimuli and/or apoptotic stimuli and/or preferably do not, or to a significantly lesser extent, differentiate into replication-deficient cells, especially when an inducible immortalizing nucleic acid sequence is activated. In one embodiment, said immortalizing nucleic acid sequence is activated when said cell of interest is present in said non-human animal. This is, for instance, performed by administering an activating agent to said non-human animal. Said nucleic acid sequence is preferably activated during ex vivo culturing of said cell of interest. Said activating agent is preferably administered to a culture medium comprising said cell of interest.

A method of the present invention has the advantage that the transduction efficacy of a stem cell or precursor cell is higher than the transduction efficacy of more differentiated cells of interest such as B cells. Therefore, less cells of interest need to be isolated from said non-human animal. Isolated cells of interest have a higher frequency of comprising said immortalizing nucleic acid sequence as compared to cells of interest that undergo transduction after isolation.

A stabilized cell of interest is defined herein as a cell that is less sensitive to growth arrest stimuli and/or apoptotic stimuli and/or that has a prolonged replicative lifespan as compared to the same kind of cell under the same circumstances that is not stabilized. Said stabilized cell is also called herein an immortalized cell. Preferably, said replicative lifespan comprises at least 6 weeks. More preferably, said replicative lifespan comprises at least 8 weeks, more preferably at least 3 months, more preferably at least 4 months, more preferably at least 6 months, more preferably at least 8 months, more preferably at least 10 months, and most preferably at least 12 months.

Said cell of interest preferably comprises a mammalian cell. More preferably, said cell of interest comprises a human cell. In one preferred embodiment, said cell of interest comprises a cell capable of producing a desired product such as, for instance, an enzyme, hormone or an antibody. Stabilization of a cell capable of producing a desired product allows ex vivo culturing of said cell and prolonged production of said desired product. Obtained product is, for instance, optionally purified and used in the production of a pharmaceutical composition and/or a (medical) test kit. In another preferred embodiment of the invention, said cell comprises an immune cell, preferably a B cell, a T cell, a natural killer cell, or an antigen presenting cell such as a dendritic cell. Stabilization of an immune cell allows for medical research and therapy. One important application is the production of (monoclonal) antibodies by stabilized B cells. Human B cell lines are generated with a method of the present invention, allowing for human antibody production. Hence, in one aspect, a method of the invention is provided wherein said immune cell comprises a B cell, preferably a human B cell. In another preferred embodiment, said cell of interest comprises a T cell, more preferably a human T cell. In another preferred embodiment, said cell of interest comprises a hepatocyte, more preferably a human hepatocyte. In the art, no efficient method for the expansion of human hepatocytes is available. Now that a method of the invention has been provided, expansion and differentiation of human hepatocytes has become possible. Stabilized hepatocytes of the invention are suitable for use, for example, in artificial liver systems, for instance to treat patients with acute liver failure or as a bridge to transplantation. Said hepatocytes are suitable for use in transplantation as an alternative to whole organ transplantation. In one embodiment, stabilized hepatocytes of the invention are used to study metabolism of drugs and for testing candidate drug compounds.

The term "a cell capable of producing a desired product" refers to a cell which has not irreversibly lost its capability of producing said product, and/or which has not irreversibly lost its capability of differentiating into a cell capable of producing said product. For instance, with a method of the present invention a B cell line is generated comprising B cells capable of replicating. Said B cells have retained their capability of differentiating into antibody producing plasma cells.

In a preferred aspect, a method of the invention is provided wherein said stem cell and/or precursor cell comprises a human stem cell and/or precursor cell, so that stabilized human cells of interest are obtained. More preferably, said precursor cell comprises a $CD34^+$ precursor cell. With a method of the invention, said human stem cell and/or precursor cell differentiates into a stabilized human cell. In one embodiment, said human cell is capable of being stabilized at any desired time point, preferably by administration of an activating agent. Said human cell of interest is preferably further cultured ex vivo after it has been obtained from said animal, generating a human cell line. Examples are a human B cell line for the production of human (monoclonal) antibodies and a human pancreatic beta-cell line for the production of insulin.

Said nucleic acid sequence which, when present in said cell of interest, is capable of stabilizing said cell of interest is also referred to herein as an immortalizing nucleic acid sequence or a stabilizing nucleic acid sequence. A cell derived from a stem cell and/or precursor cell comprising said nucleic acid sequence is less sensitive to growth arrest stimuli and/or apoptotic stimuli and/or has a prolonged replicative lifespan as compared to the same kind of cell under the same circumstances that does not comprise said nucleic acid sequence. Said nucleic acid sequence of the invention is, for instance, capable of overcoming cell cycle arrest and/or preventing senescence, differentiation and/or apoptosis. Preferably, said nucleic acid sequence is capable of inducing and/or enhancing replication of said cell of interest. The presence of said nucleic acid sequence in a cell of interest preferably prolongs replication life span, for instance by preventing differentiation of said cell, since differentiation often involves a loss of replication capacity (this is called terminal differentiation). For instance, during a T cell dependent B cell response, the B cells undergo extensive proliferation followed by differentiation in antibody-producing plasma cells, which is accompanied by cell cycle arrest. In one embodiment, a nucleic acid sequence of the invention at least in part prevents said differentiation and cell cycle arrest.

In a preferred embodiment, said nucleic acid sequence comprises at least a functional part of a gene encoding a Signal Transducer of Activation and Transcription (STAT) protein. Preferably, said STAT protein comprises a constitutively active STAT protein (CA-STAT). Several STAT proteins are known. For instance, it is described in the art that IL-4 activates STAT6 and, indirectly, STAT5 (Lischke et al., 1998; Rolling et al., 1996) while IL-2 activates STAT3 and STAT5 (reviewed in (Leonard and O'Shea, 1998)). STAT3 and STAT6 molecules are involved at some point in B cell development and differentiation. STAT6 affects the choice of immunoglobulin isotype (IgE) during class switch recombination (Kaplan et al., 1996; Shimoda et al., 1996), while STAT3 is implicated in plasma cell differentiation (Reljic et al., 2000). The role of STAT5 in B cell development and differentiation is less well defined. There are two known forms of STAT5, STAT5a and STAT5b, which are encoded by two different, tandemly-linked genes. They play both unique and redundant roles in the response of cells to a wide variety of growth factors (Teglund et al., 1998).

In another preferred embodiment, said nucleic acid sequence comprises at least a functional part of a gene encoding BCL-6. BCL-6 encodes a transcriptional repressor, which is frequently activated by chromosomal translocation in non-Hodgkin's lymphoma. The chromosomal translocations involving BCL-6 invariably affect the promoter only, and leave the open reading frame of BCL-6 intact. BCL-6 is required for normal B cell development and maturation and is required for the formation of germinal centers. (Ye, 1997). BCL-6 prevents differentiation of B cells to plasma cells through inhibition of Blimp-1.

In yet another preferred embodiment, said nucleic acid sequence is capable of at least in part inactivating p53 expression. The tumor suppressor p53 plays an important role in regulation of the cell cycle and apoptosis in response to DNA damage caused by irradiation or exposure to genotoxic mediators. P53 mediates several cellular responses including cell cycle arrest, senescence, differentiation and apoptosis depending on the cell type and the microenvironment. While mutations occur in the gene encoding p53 in human cancers including tumors of hematopoietic origin, its function in normal human hematopoietic development remains largely unexplored. P53 plays a role in regulating the replicative life span of mature human T cells in vitro through suppression of human telomerase reverse transcriptase (hTERT). Telomeres are DNA repeats at the distal ends of the chromosomes, which protect against chromosome end-to-end fusions. Telomeres are shortened at each cell division, and cells with critically short telomeres undergo cell cycle arrest and become senescent. hTERT, which prevents telomere shortening, is transiently upregulated in T cells upon stimulation through the TCR, and expression of a dominant negative mutant of hTERT significantly decreased the lifespan of both $CD4^+$ and $CD8^+$ T cells, indicating that hTERT plays a regulatory role in the lifespan of human T cells. Downregulation of p53, for instance by RNA interference (RNAi), extends the lifespan of cells of interest such as mature human T cells and neutralizes the inhibition by dominant negative hTERT, indicating that p53 regulates hTERT expression in primary human T cells.

According to the present invention, the incorporation of a nucleic acid sequence encoding at least a functional part, derivative or analogue of a STAT protein and/or BCL 6 into a stem cell or progenitor cell results in a stabilized cell of interest. Moreover, the incorporation of a nucleic acid sequence capable of at least in part inactivating p53 expression, such as, for instance, RNA interference-inducing DNA fragments that target p53 nucleic acid sequence, into a stem cell or progenitor cell results in a stabilized cell of interest. Preferably, a nucleic acid sequence of the invention is incorporated into a stem cell or a B cell precursor cell, resulting in a stabilized B cell and/or a B cell capable of being stabilized. Said B cell is preferably further cultured ex vivo. Preferably, said STAT protein comprises a constitutively active STAT5 protein, as described in WO 03/052083 (incorporated herein by reference). More preferably, said STAT protein comprises a constitutively active STAT5a, and/or constitutively active STAT5b protein.

By at least a functional part of a STAT protein and/or BCL-6 is meant a proteinaceous molecule that has the same capability—in kind, not necessarily in amount—of stabilizing a cell of interest as compared to a STAT protein and/or BCL-6. A functional part of a STAT protein is, for instance, devoid of amino acids that are not, or only very little, involved in said capability. A derivative of a STAT protein and/or BCL-6 is defined as a protein which has been altered such that the capability of said protein of stabilizing a cell of interest is essentially the same in kind, not necessarily in amount. A derivative can be provided in many ways, for instance through conservative amino acid substitution. An analogue of a STAT protein and/or BCL-6 is defined as a molecule having the same capability of stabilizing a cell of interest in kind, not necessarily in amount. Said analogue is not necessarily derived from said STAT protein and/or BCL-6.

A nucleic acid sequence capable of at least in part inactivating p53 expression is defined herein as a nucleic acid sequence which is capable of inhibiting transcription and/or translation of a p53 encoding nucleic acid sequence, or as a nucleic acid sequence encoding a proteinaceous molecule which is capable of inhibiting transcription and/or translation of a p53 encoding nucleic acid sequence. Said nucleic acid sequence capable of at least in part inactivating p53 expression is, for instance, capable of specifically binding p53 or a p53 encoding nucleic acid sequence. In one aspect said nucleic acid sequence capable of at least in part inactivating p53 expression encodes a proteinaceous molecule capable of specifically binding p53 or a p53 encoding nucleic acid sequence.

Continuous expression of an immortalizing nucleic acid of the present invention is not always desired. For instance, production of a compound of interest such as an antibody, hormone or protein often requires differentiation of replicating cells. Once a B cell line has been established, a part of the B cell population is selected for antibody production. Since antibody production requires differentiation of the selected B cells, expression of an immortalizing nucleic acid sequence capable of prolonging replication life span is, preferably, at least in part inhibited. In one aspect of the present invention, said immortalizing nucleic acid sequence of the invention is therefore capable of being switched on and off. For instance, replication of cultured cells is regulated.

In the art, many ways are known of switching a nucleic acid sequence on or off. It is possible, for instance, to introduce antisense nucleic acid into a cell of interest, which antisense nucleic acid is capable of binding (mRNA of) an immortalizing nucleic acid sequence of the invention, thereby inactivating it. Said antisense nucleic acid is preferably generated under certain defined circumstances. In one embodiment, a cell of interest comprising an immortalizing nucleic acid sequence of the invention is provided with a nucleic acid sequence encoding a proteinaceous molecule capable of specifically binding (an expression product of) said immortalizing nucleic acid sequence of the invention. Said nucleic acid sequence encoding said proteinaceous molecule is preferably produced under certain defined circumstances only, and/or said proteinaceous molecule is preferably capable of specifically binding said (expression product of said) immortalizing nucleic acid sequence of the invention under certain defined circumstances only. As is known by the skilled person, many alternative methods for switching a nucleic acid sequence on or off are available in the art.

An immortalizing nucleic acid sequence of the invention is preferably switched on or off with a method as described in patent application WO 03/052083, herein incorporated by reference. One method comprises the step of associating an inactivating agent with (an expression product of) said immortalizing nucleic acid sequence, such as, for instance, a STAT5 protein. The inactivating agent is then switched on or off, for instance depending on the stage of a cell of interest. Said inactivating agent, for example, may comprise an inducible promoter/excision system such as cre-lox or FLP/FRT excision system.

In one embodiment, nucleic acid inducing RNA interference is used. For instance, double stranded interfering RNA (RNAi) or DNA that produces RNAi is used to control expression of an immortalizing nucleic acid sequence of the invention, such as p53.

In a preferred embodiment, said inactivating agent comprises a proteinaceous molecule that is associated with an expression product of an immortalizing nucleic acid sequence of the invention (such as a STAT5 protein) as a fusion protein. Preferably, a nucleic acid sequence encoding said inactivating agent is fused to said immortalizing nucleic acid sequence and expressed in a cell of interest so as to produce a fusion protein.

As outlined in WO 03/052083, said inactivating agent is preferably switched on or off by altering said fusion protein's environment. For example, said estrogen receptor and STAT5 are produced in a cell of interest as a fusion protein (STAT5-ER). Said estrogen receptor acts as an inactivating agent to STAT5, because said fusion protein is inactive, since it forms a complex with heat shock proteins in the cytosol preventing said STAT5 protein from reaching the nucleus. However, upon incubation with 4 Hydroxy-Tamoxifen (4HT), said fusion protein (STAT5-ER) dissociates from said heat shock proteins and is transported to the nucleus in its active form. Replication of said cell of interest is enhanced by STAT5. Removal of 4HT results in cessation of growth of cells of interest as the expressed STAT5 and estrogen receptor become associated again with heat shock proteins and are therefore inactive. Removal of 4HT thus results in termination of replication of a cell of interest. Thus, in this embodiment, the inactivating agent ER is switched on or off using 4HT ((WO 03/052083, pages 14-15) and (Scheeren et al. (2005) Nature Immunology, Vol 6, No. 3, page 306, last column, last paragraph—page 307, first column, first paragraph), both incorporated herein by reference). A non-limiting example of production of STAT5b-ER fusion constructs is described in Scheeren et al. (2005) Nature Immunology, Vol 6, No. 3, page 311, first column, first whole paragraph (lines 3-14). This paragraph is incorporated herein by reference.

Another example of an inactivating agent is a transcription factor binding site, preferably upstream or downstream of an immortalizing nucleic acid sequence of the invention, whereby expression of said nucleic acid sequence is under the control of a transcription factor. Expression of said nucleic acid is switched on or off by the presence or absence, respectively, of a transcription factor (a transactivator). The presence or absence of said transactivator is, for instance, controlled by manipulating its expression or function in a cell of interest. This is, for instance, conveniently achieved by providing said cell of interest with two plasmids; the first plasmid encoding said transcription factor (transactivator), and the second plasmid encoding an immortalizing nucleic acid sequence of the invention such as STAT5. Said second plasmid preferably also comprises a nucleic acid binding site for said transactivator, preferably upstream of said immortalizing nucleic acid sequence such that expression of said immortalizing nucleic acid sequence is under the control of said transactivator. When desired, expression of said immortalizing nucleic acid sequence is switched off, for instance by contacting said cell with an agent that inactivates the transactivator. By removing the agent, the transactivator is active and allows expression of said immortalizing nucleic acid sequence. An example of such a system is the tetracycline regulatable system, such as described by Bujard and collaborators (Gossen, et al., 1995).

Many methods are known in the art for providing a stem cell and/or precursor cell with an immortalizing nucleic acid sequence of the invention. For instance, calcium phosphate transfection, DEAE-Dextran, electroporation, or liposome-mediated transfection is used. Alternatively, direct injection of the nucleic acid is employed. Preferably however, said nucleic acid is introduced into the cell by a vector, preferably a viral vector. Various terms are known in the art which refer to introduction of nucleic acid into a cell by a vector. Examples of such terms are "transduction," "transfection" or "transformation." Techniques for generating a vector with an immortalizing nucleic acid sequence and for introducing said vector into a cell are known in the art. Marker genes such as, for instance, antibiotic resistance or sensitivity genes, and/or genes encoding markers such as cell surface antigens or fluorescent proteins like green fluorescence protein, are preferably used in identifying clones containing the introduced nucleic acid, as is well known in the art.

Said vector preferably comprises a retroviral vector. More preferably, said vector comprises a lentiviral vector, because lentiviral vectors have at least two advantages: they are capable of efficiently transducing dividing and non-dividing cells, and they are not silenced during development, providing stable, long-term gene expression.

In a preferred embodiment, an immortalizing nucleic acid sequence of the invention, such as, for instance, a nucleic acid sequence encoding STAT or BCL-6, or a nucleic acid sequence capable of at least in part inactivating p53 expression, is operably linked to an inducible promoter. Expression of said immortalizing nucleic acid sequence is regulated by said inducible promoter. In one embodiment, said inducible promoter is active in a cell of interest, and is inactivated by administration of an inactivating agent. Preferably however, said inducible promoter is generally inactive in a cell of interest with low background expression, such that said immortalizing nucleic acid sequence is not expressed, or is to a small extent expressed in said cell. Upon administration of an inducing agent, said inducible promoter is activated, which results in expression of said immortalizing nucleic acid sequence and stabilization of said cell of interest. Said inducing agent is preferably not naturally present in said cell of interest. In one embodiment, a vector comprising said immortalizing nucleic acid sequence operably linked to an inducible promoter is used. Inducible promoters, suitable for use in a method of the present invention, are known in the art. In one embodiment, a tetracyclin and/or doxycyclin inducible Tet operon as disclosed in WO 01/20013, herein incorporated by reference, is used.

A vector of the invention preferably comprises a Tet-dependent transcriptional regulatory system. The Tet-dependent transcriptional regulatory system is one of the best studied systems with proven efficacy both in vitro and in vivo (Freundlich, Baron, Bonin, Gossen and Bujard, Methods Enzymology 283, 159-173, 1997; Baron and Bujard, Methods Enzymology 327, 401-421, 2000). This system is based on the bacterial Tn10 Tetracycline operator, and is made up of two components; the tetracycline repressor protein (TetR), and the tetracycline operator sequence (TetO), which the TetR binds to with a high specificity. In the absence of tetracycline, TetR dimerizes, binds to the TetO, and prevents gene expression. Tetracycline is able to bind to the TetR, inducing a conformational change, leading to the disassociation of TetR from the TetO and gene expression.

This system has been adapted for use in a mammalian system by the fusion of the VP16 transactivation domain of H. simplex virus to TetR to make a tetracycline responsive transactivator (tTA), and by designing a tetracycline responsive promoter element by fusing seven repeats of the TetO to a minimal CMV promoter (Tet Responsive Element, TRE). In the absence of tetracycline or doxycycline (a tetracycline analogue), tTA is active and initiates transcription of genes placed under control of the TRE. Addition of doxycycline prevents transcriptional activation.

Preferably however, a vector of the present invention comprises a Tet-dependent transcriptional regulatory system, which is inactive in the absence of tetracycline and/or doxycycline, and which is capable of being activated by administration of tetracycline and/or doxycycline. A vector of the invention therefore preferably comprises a TetR mutant as described in Urlinger et al. (Urlinger S; Baron U; Thellmann M; Hasan M; Bujard H; Hillen W. Proc. Natl. Acad. Sci. (2000) Vol 97, No 14, 7963-7968), containing four amino acid substitutions in which three of the substitutions are located where the inducer molecule binds, and the final substitution is located in the dimerization domain. When this TetR mutant is fused to a VP16 transactivation domain, a reverse phenotype is obtained where transcriptional activation is dependent on the presence of doxycycline. This mutant is named rtTA.

The rtTA as described by Urlinger et al (Urlinger S et al; Proc. Natl. Acad. Sci. (2000) Vol 97, No 14, 7963-7968) has several limitations including requiring high levels of doxycycline for maximal activation (1-2 μg/ml), which may not be readily reached in certain tissues, residual affinity to the TRE in the absence of doxycycline, and cellular toxicity from the VP16 activation domain. A vector of the invention therefore more preferably comprises an immortalizing nucleic acid sequence operably linked to a Tet-dependent transcriptional regulatory system comprising an improved mutant of rtTA called rtTA2-S2 and rtTA2-M2 (Urlinger S et al; Proc. Natl. Acad. Sci. (2000) Vol 97, No 14, 7963-7968). These mutants have been generated by performing random and directed mutagenesis on the TetR, and identifying several mutants that performed better than the originally described rtTA. To reduce cellular toxicity, the VP16 transcriptional activation domain was modified to a minimal activation domain containing three repeats of the "F" type to minimize the sequestering of the cellular transcriptional machinery (Urlinger S et al; Proc. Natl. Acad. Sci. (2000) Vol 97, No 14, 7963-7968).

Most Tet regulated transgene expression systems rely on two separate constructs, one containing the TRE (Tet Responsive Element) and nucleic acid of interest (transgene), and the second containing rtTA driven by a constitutive promoter. Working with this binary system can be challenging both in vitro and in vivo where a cell requires transduction by two different vectors, rendering experimental reproducibility difficult. Other difficulties are encountered with the generation of Tet regulated transgenic animals, requiring the generation of two separate transgenic animal lines and successful crossing to create a double transgenic animal. The present inventors have therefore combined an inducible promoter (PtetO$_7$CMVm), nucleic acid of interest (also called transgene) and rtTA2-S2 into a single cassette, and cloned this into a lentiviral vector backbone. Two different cassettes have been generated where rtTA2-S2 is either constitutively expressed with the CMV promoter or is placed in an autoregulatory loop, where the TRE drives the expression of both the transgene and rtTA2-S2 linked by an EMCV IRES element. The present inventors tested these two systems in a panel of human primary and established cell lines and found that the autoregulatory loop performed better than the constitutively expressed rtTA2-S2 in all cell lines tested. One aspect of the invention, therefore, provides a vector comprising an autoregulatory loop for rtTA and transgene expression. An advantage of such a system is the low uninduced expression levels because the rtTA-transactivator is not synthesized in the absence of doxycycline. Toxicity of basal rtTA expression is avoided.

Figure 15:
FIG. 15. Schematic representation of inducible lentiviral vectors. (A) vectors with constitutive expression of rtTA, for instance TetO$_7$mCMV CMV rtTA3. (B) vectors with autoregulatory expression, for instance TetO$_7$mCMV IRES rtTA-S2 or TetO$_7$mCMV IRES rtTA3.
Figure 15:

This concept was previously demonstrated in the context of a replication-competent HIV-based vector (Verhoef K, Marzio G, Wolfgang H, Bujard H, Berkhout B. Strict control of human immunodeficiency virus type 1 replication by a genetic switch: Tet for Tat. Journal of Virology 2001; 75:979-987). An example of a preferred vector of the present invention is depicted in FIG. 15B.

A potential disadvantage of this vector system is that a more sensitive Tet-system is required to "kick-start" the expression loop. Using more sensitive Tet-systems which were obtained through virus evolution methods (Das A T, Zhou X, Vink M, Klayer B, Verhoef K, Marzio G, Berkhout B. Viral evolution as a tool to improve the tetracycline-regulated gene expression system. Journal of Biological Chemistry 2004; 279:18776-18782), the present inventors were able to activate this gene expression loop. A mutant rtTA, from here on referred to as rtTA3, was used in the autoregulatory cassette generated from directed (Urlinger S et al; Proc. Natl. Acad. Sci. (2000) Vol 97, No 14, 7963-7968) and viral (Das A T et al, Journal of Biological Chemistry 2004; 279:18776-18782; WO 01/20013) evolution. rtTA3 exhibits a thirteen-fold increased sensitivity to doxycycline compared to wild-type rtTA (see table 1 of Das A T et al, Journal of Biological Chemistry 2004; 279:18776-18782). The present invention thus provides a doxycycline regulated transgene expression lentiviral vector comprising rtTA3, capable of tight and graded expression of a transgene. In a preferred aspect, said vector comprises rtTA3 operably linked to an internal ribosome entry site, such that said rtTA3 is placed in an autoregulatory loop where the TRE drives the expression of both the transgene and rtTA3. Use of said vector in a method of the invention is also herewith provided. However, said vector is also suitable for immortalizing a cell of interest in other ways, for instance, via transduction of a cell of interest after said cell of interest has been obtained. Use of a vector comprising rtTA3 and a gene of interest for transducing a cell of interest is therefore also herewith provided. Preferably, said rtTA3 is operably linked to an internal ribosome entry site, such that said rtTA3 is placed in an autoregulatory loop where the TRE drives the expression of both said gene of interest and rtTA3. More preferably, said gene of interest comprises an immortalizing nucleic acid sequence, such that said cell of is stabilized. Said cell of interest preferably comprises a hepatocyte or an immune cell, preferably a B cell.

A vector of the present invention furthermore preferably comprises a human hepatitis B virus posttranscriptional regulatory element (HBV PRE). The HBV PRE is a cis-acting element able to increase expression of transgenes when included in the transcribed region of said gene, probably by stimulating export of unspliced mRNA from the nucleus (Seppen et al. Journal of Hepatology 36 (2002) 459-465). The PRE element contains the start codon and most of the coding region of the HBVx protein. HBVx is essential for viral replication, and is implicated in the development of hepatocellular carcinoma associated with HBV infection.

In addition to an immortalizing nucleic acid sequence of interest, it is sometimes desired to provide a cell of interest with a second compound. For instance, a cell of interest is preferably additionally provided with telomerase reverse transcriptase such that shortening of the telomeres of said cell of interest is prevented. Said compound is, for instance, provided to said cell of interest by providing said cell with a nucleic acid sequence encoding said compound. Preferably, a vector comprising both said immortalizing nucleic acid sequence and a nucleic acid sequence encoding said compound is used, because the use of single transduction step vectors is less challenging than the use of two independent vectors, since cotransfer of two independent elements is not efficient in primary cells. Said nucleic acid sequence encoding said additional compound is, for instance, inserted between said inducible promoter and said immortalizing nucleic acid sequence. Of course, said insertion preferably does not result in a frame shift of the downstream region comprising said immortalizing nucleic acid sequence. Alternatively, said nucleic acid sequence encoding said additional compound is inserted downstream of said immortalizing nucleic acid sequence. Preferably however, a bidirectional promoter is used, such as, for instance, the bidirectional promoter from pBI-4 described in Unsinger et al. (Unsinger et al., Retroviral vectors for the transduction of autoregulated, bidirectional expression cassettes. Molecular Therapy Vol 4, No 5, November 2001, pages 484-489). Said nucleic acid sequence encoding said additional compound is preferably located on one site of said bidirectional promoter, while said immortalizing nucleic acid sequence is located on the other site of said promoter. Preferably, said bidirectional promoter is an inducible promoter. More preferably, said promoter is inducible by doxycycline, such as the bidirectional promoter from pBI-4 described in Unsinger et al. This allows (separate) regulation of said nucleic acid sequences.

In another embodiment, an immortalizing nucleic acid sequence is incorporated into a vector as an immortalizing nucleic acid sequence-estrogen receptor fusion construct. Preferably, an ER-STAT5 vector as described in the examples is used, which is inducible by tamoxifen (T. D. Littlewood, D. C. Hancock, P. S. Danielian, M. G. Parker and G. I. Evan, A modified oestrogen receptor ligand-binding domain as an improved switch for the regulation of heterologous proteins. Nucleic Acid Res. 23 (1995), pp. 1686-1690, incorporated herein by reference).

Hence, a method of the invention is provided wherein said nucleic acid sequence, which, when present in said cell of interest, is capable of stabilizing said cell of interest, is operably linked to an inducible promoter. Preferably, said promoter is inducible by doxycyclin and/or tamoxifen. In another preferred embodiment, said stem cell and/or precursor cell is transduced with a vector, preferably a lentiviral vector, comprising said nucleic acid sequence, which, when present in said cell of interest, is capable of stabilizing said cell of interest. Preferably, said stem cell and/or precursor cell is transduced with an ER-STAT5 vector. More preferably, said stem cell and/or precursor cell is transduced with a vector comprising an inducible promoter (preferably PtetO$_7$CMVm), a nucleic acid of interest, and rtTA2-S2. Most preferably, said stem cell and/or precursor cell is transduced with a vector comprising an inducible promoter (preferably PtetO$_7$CMVm), a nucleic acid of interest, and rtTA3. Said rtTA2-S2 and/or rtTA3 is preferably operably linked to an internal ribosome entry site (IRES), such that said rtTA2-S2 and/or rtTA3 is placed in an autoregulatory loop. An isolated or recombinant nucleic acid sequence comprising an inducible promoter (preferably PtetO$_7$CMVm), a nucleic acid of interest, and rtTA3 (preferably operably linked to an IRES) is also herewith provided. Said nucleic acid of interest preferably comprises an immortalizing nucleic acid sequence of the present invention. A vector of the present invention furthermore preferably comprises a human hepatitis B virus posttranscriptional regulatory element (HBV PRE). Most preferably, a vector of the invention comprises a vector as depicted in FIG. 15B.

A method of the present invention is particularly suitable for producing immortalized immune cells. For instance, hematopoietic stem cells (or B cell precursor cells) are transduced with an immortalizing nucleic acid sequence and administered to a non-human animal. B cells obtained from said animal are stabilized. In one embodiment, said B cells are less sensitive to growth arrest stimuli and/or apoptotic stimuli. Preferably, said B cells have a prolonged replication life span. Preferably, said non-human animal is provided with an antigen of interest before an immune cell of interest is obtained. After said antigen of interest is administered to said animal, immune cells such as T cells, or B cells capable of producing antibodies against said antigen of interest, are obtained. Since these immune cells already comprise an immortalizing nucleic acid sequence, these immune cells are suitable for continued culturing ex vivo. Preferably, said nucleic acid is activated during said culturing. In one embodiment of the invention, a human B cell line is produced. Said B cell line is suitable for the production of (monoclonal) antibodies against any antigen of interest. Preferably, said antigen of interest is at least an immunogenic part of an antigen (preferably expressed by (viral) pathogens such as for instance RSV), a human autoantigen, a tumor-associated antigen, TNF-alpha and/or an antigen expressed on malignant melanoma cells. Since non-human animals are used, it is possible to produce human B cells against a desired antigen by immunizing said animal with said antigen. Human B cells capable of producing antibodies against human auto-antigens are also produced, because non-human animals are used.

When human cells are produced in a non-human animal, said animal's immune system is preferably at least partly impaired, in order to at least partly avoid animal immune responses against said human cells. This is, for instance, accomplished by irradiating said animal before it is provided with said human stem cell and/or human precursor cell. Preferably however, a knock out non-human animal is used which is devoid of at least one gene responsible for said animal's immune response. Preferably, said animal is essentially devoid of at least one gene involved in the production of endogenous B cells, endogenous T cells and/or endogenous natural killer cells. A knock out animal is, for instance, produced by gene silencing or by introducing mutations using methods well known in the art. Gene silencing is for instance performed by providing said animal with a compound capable of specifically binding (an expression product of) said gene. Said compound, for instance, comprises a protein or antisense RNA. Mutations are, for instance, induced using site specific mutagenesis. Many alternative methods for producing a knock out non-human animal are known in the art which do not need further explanation here. Hence, a method of the invention is provided wherein said animal is essentially devoid of at least one kind of endogenous hematopoietic cell.

In a preferred embodiment, a non-human animal is used which is essentially devoid of endogenous B cells, endogenous T cells, and/or endogenous natural killer (NK) cells. Said non-human animal preferably comprises a mouse, more preferably a RAG2$^{-/-}$ γc$^{-/-}$ mouse (Kirberg J, Berns A, von Boehmer H. Peripheral T cell survival requires continual ligation of the T cell receptor to major histocompatibility complex-encoded molecules. J Exp Med. 1997; 186:1269-1275, incorporated herein by reference; Weijer K, Uittenbogaart C H, Voordouw A, Couwenberg F, Seppen J, Blom B, Vyth-Dreese F A, Spits H. Intrathymic and extrathymic development of human plasmacytoid dendritic cell precursors in vivo. Blood. 2002; 99:2752-2759, incorporated herein by reference) which is a double mutant strain lacking B, T and NK cells. Transplantation of human stem cells and/or human hematopoietic precursor cells into said mouse results in a mouse with a human hematopoietic system (Weijer et al, 2002 (incorporated herein by reference); Traggiai et al, 2004). Said mouse is very suitable for use in a method of the present invention, since generated stabilized human cells of interest are not, or to little extent, attacked by murine immune responses.

In one aspect of the invention, said stem cell and/or precursor cell is administered to said animal within one week after birth. Preferably, said stem cell and/or precursor cell is administered to said animal within three days after birth, more preferably within one day after birth. It has been demonstrated by the present inventors that early injection results in increased T cell and B cell engraftment.

With a method of the invention, a stabilized cell of interest is obtained which can be further cultured ex vivo, for instance, producing a cell line. The invention therefore provides a stabilized cell of interest obtainable by a method of the invention. Preferably, said cell of interest comprises an immune cell, such as a B cell, a T cell or a hepatocyte. Most preferably, said cell of interest comprises a human B cell or a human hepatocyte. An isolated stem cell and/or precursor cell of a cell of interest, said stem cell and/or precursor cell comprising a nucleic acid sequence, which, when present in said cell of interest, is capable of stabilizing said cell of interest, is also herewith provided. Particularly, the production of stabilized human cells of interest is provided, since human replicating cells are particularly suitable for therapy, medical testing and/or the production of human compounds of interest, such as human antibodies, human hormones and/or human proteins such as human enzymes. The invention therefore preferably provides a method of the invention wherein said precursor comprises a human CD34$^+$ precursor cell. Preferably, a stem cell and/or precursor cell of the invention comprises at least a functional part of a gene encoding a STAT protein and/or BCL 6, and/or a nucleic acid sequence capable of at least in part inactivating p53 expression. Said STAT protein preferably comprises a constitutively active STAT protein. In a preferred embodiment, said stem cell and/or precursor cell is transduced by a vector of the present invention. Most preferably, said vector comprises an inducible promoter, so that expression of said immortalizing nucleic acid sequence is regulated. A non-human animal comprising a stem cell and/or precursor cell and/or a cell of interest of the present invention is also herewith provided. Said animal is suitable for producing cells of interest, such as human B cells, preferably capable of producing antibodies against an antigen of interest.

A method of the invention is particularly suitable for production of stabilized B cells. The invention thus provides a method for producing a B cell line comprising:
  obtaining a B cell with a method of the invention; and
  culturing said B cell ex vivo.

Said B cell preferably comprises a human B cell. Said stabilized B cells are particularly suitable for production of (monoclonal) antibodies. In order to obtain B cells capable of producing antibodies which are specifically directed against an antigen of interest, said antigen of interest is administered to said non-human animal in order to evoke a (human) immune response.

The invention thus furthermore provides a method for producing antibodies specifically directed towards an antigen of interest, comprising:
  providing a stem cell and/or a precursor cell of a B cell with a nucleic acid sequence which, when present in a B cell, is capable of stabilizing said B cell;
  providing a non-human animal with said stem cell and/or precursor cell;
  providing said non-human animal with said antigen of interest;
  allowing generation of a B cell capable of producing antibodies specifically directed towards said antigen of interest;
  obtaining said B cell; and
  harvesting antibodies produced by said B cell or by a B cell derived therefrom.

Preferably, said precursor cell is provided with at least a functional part of a gene encoding a STAT protein and/or BCL 6, and/or with a nucleic acid sequence capable of at least in part inactivating p53 expression. Said B cell is preferably cultured ex vivo after it has been obtained from said animal. In one embodiment, a B cell line is generated. Since production of stabilized human B cells is favored, said precursor cell preferably comprises a human $CD34^+$ precursor cell.

In one embodiment, said non-human animal comprises a mouse. Preferably, said mouse comprises a $RAG2^{-/-}$ $\gamma c^{-/-}$ mouse, since said mouse is particularly suitable for generation of a human hematopoietic system.

The invention is further illustrated by the following examples. The examples do not limit the scope of the invention in any way.

EXAMPLES

Example 1

Material and Methods

Mice

H-2d $RAG2^{-/-}$ mice (kindly provided by Dr. Antonius Rolink and Dr. Shunichi Takeda; Basel Institute for Immunology, Basel, Switzerland (Takeda S, Rodewald H R, Arakawa H, Bluethmann H, Shimizu T. Immunity. 1996; 5:217-228)) were crossed with IL-$2R\gamma c^{-/-}$ mice (Blom B, Spits H, Krimpenfort P. In: Smit Sibing a CT, Das P C, Lowenberg B, eds. Cytokines and Growth Factors in Blood Transfusion. London: Kluwer Academic Publishers; 1997:3-12) to obtain $H-2^d$ $RAG2^{-/-}$IL-$2R\gamma c^{-/-}$ mice (further referred to as $RAG2^{-/-}$ $\gamma c^{-/-}$ mice: Weijer K, Uittenbogaart C H, Voordouw A, Couwenberg F, Seppen J, Blom B, Vyth-Dreese F A, Spits H. Blood. 2002; 99:2752-2759; Kirberg J, Berns A, von Boehmer H. J Exp Med. 1997; 186:1269-1275). These mice are immunodeficient as they show a total absence of T, B and NK lymphocytes. Mice were bred and maintained in isolators, and were fed autoclaved food and water. All manipulations were performed under laminar flow.

Fetal Liver and Cord Blood Cell Preparation

Human fetal liver was obtained from elective abortions. Gestational age was determined by ultrasonic measurement of the diameter of the skull and ranged from 14 to 20 weeks. The use of this tissue was approved by both Medical Ethical Committees of the Netherlands Cancer Institute and Academic Medical Center and was contingent on informed consent. Human fetal liver cells were isolated by gentle disruption of the tissue by mechanical means, followed by density gradient centrifugation over Ficoll-Hypaque (Lymphoprep; Nycomed Pharma, Oslo, Norway). Single-cell suspensions were prepared by mincing tissues and pressing them through a stainless steel mesh. Large aggregates were removed, and the cells were washed once with medium before isolation of $CD34^+$ cells. Transplantation of human $CD34^+$ cells into $RAG2^{-/-}$ $\gamma c^{-/-}$ mice and evaluation of human cell engraftment Enrichment of $CD34^+$ cells (>98% pure, as assessed by flow cytometry, data not shown) was performed using the CD34 Progenitor Cell Isolation Kit (Miltenyi Biotec, Bergisch Gladbach, Germany). $CD34^+$ cells (0.2 to 2 million cells) were transplanted ip into sub-lethally irradiated (350 cGy) newborn $RAG2^{-/-}$ $\gamma c^{-/-}$ mice (<1 week old). Peripheral blood was collected from the tail vein every 3-4 weeks after transplantation to determine the kinetics of human cell engraftment. Mice were sacrificed at different time points after transplantation, and peripheral blood (PB), liver, lung, spleen, bone marrow (BM) and the thymus were evaluated for the presence of human cells. A total body irradiation (TBI) of 3.5 Gy is performed since non-irradiated mice do not always show a repopulation with human cells. Mononuclear cells (MNC) were isolated by density gradient centrifugation over Ficoll-Hypaque and stained with anti-human CD45 (Becton and Dickinson, San Jose, Calif.) and other markers. Expression of these markers was measured on a FACS Calibur (Becton and Dickinson) and analyzed with the FCS express program (Denovosoftware, Ontario, Canada). The grafted human mononuclear population was defined on the basis of forward and side scatter parameters, and the percentage of positive cells for a given marker was determined for cells falling within the leukocyte and $CD45^+$ gates. There were no cells present that reacted with the anti-human CD45 in non-transplanted $RAG2^{-/-}$ $\gamma c^{-/-}$ mice. Specific subsets of human cells were quantified by staining with anti-human specific mAbs, which were conjugated with fluorescein isothiocyanate (FITC), phycoerythrin (PE), peridinin chlorophyll protein (PerCP) or allophycocyanin (APC): CD11c, CD19, CD34 and CD45RA (Coulter-Immunotech), CD3, CD4, CD8, CD10, CD14, CD16, CD20, CD56, CD83 and CD123 (Becton and Dickinson); CD38 and CD45RO (Dako, Glostrup, Denmark) and BDCA-2 (Miltenyi Biotec).

Lentivirus Production

Replication-defective self-inactivating HIV vectors were produced by transient transfection of 293T cells using FUGENE (Roche, Nutley, N.J.) and three different plasmids. The plasmids used were: the VSV-G envelope coding plasmid pMD.G, the packaging plasmid pCMVDR8.91 designed to provide the Gag, Pol, Tat and Rev proteins to produce the virus particle, and the transfer vector pTRIPdeltaU3-E1alpha (Sirven A, Ravet E, Charneau P, Zennou V, Coulombel L, Guetard D, Pflumio F, Dubart-Kupperschmitt A. Mol. Ther. 2001; 3:438-448). pTRIPdeltaU3-E1alpha has been modified to include the siRNA cassette from the pSUPER vector containing the human p53 targeting sequence 5'GACTC-CAGTGGTAATCTAC (SEQ ID NO:1), described by Brummelkamp et al (Brummelkamp T R, Bernards R, Agami R. Science. 2002; 296:550-553) and also carries the enhanced GFP gene driven by the elongation-factor-1-alpha promoter. Twenty hours after the transfection, medium was replaced by Yssel's medium (Yssel H, De Vries J E, Koken M, van Blitterswijk W, Spits H. Methods. 1984; 72:219-227), and two samples of virus were collected at 24 and 48 hours. The virus-containing supernatants were centrifuged for 10 minutes at 1800 rpm to remove cells and then passed through a 0.22 mm filter and kept at −80° C. until use.

Transduction Protocol

Transduction of $CD34^+$ human cells was performed by one cycle of overnight exposure to viral supernatant on retronectin (Takara Shuzo Co, Otsu, Japan) coated 24-well plates in the absence of cytokines. Next day, cells were washed, and, either injected ip into mice, or kept in culture in Yssel's medium in the presence of Thrombopoietin, Stem Cell Factor and IL-7 at 10 ng/ml each (all from Peprotech). The efficiency of transduction was estimated by determining the percentage of GFP positive cells, 2-3 days later, by flow cytometry.

Western Blot

Total cellular extracts were prepared by lysing equal numbers of cells in RIPA buffer for 30 minutes on ice. Equivalent amounts of proteins, determined by the Bio-Rad Protein Assay (Bio-Rad, Munchen, Germany), were loaded onto 10% SDS gels. P53 protein was detected using the monoclonal antibody DO-1 from Santa Cruz Biotechnology, and beta-actin as a loading control using a polyclonal antibody, 1-19, also from Santa Cruz.

Human T Cell Culture

The expansion of human T cells from blood and spleen of $RAG2^{-/-}$ mice, reconstituted with human transduced stem cells, was done by stimulation with a feeder mix consisting of irradiated allogeneic human peripheral blood cells (PBLs) from two different donors and an irradiated EBV-transformed B cell line (JY), PHA (Gibco, Grand Island, N.Y.), and recombinant human IL-2 (rhIL-2; Roche, Nutley, N.J.), as described (Spits H, Ijssel H, Terhorst C, de Vries J E. J. Immunol. 1982; 128:95-99). All the cultures involving human cells were done in Yssel's medium.

Detection of Apoptotic Cells

Cellular viability was analyzed by flow cytometry, before or 24 hours after gamma-irradiation (3000 Rad), or after treatments with staurosporine (1 µM) or fludarabine (5 µM). Briefly, cells were harvested and washed in ice-cold HEPES buffer (10 mM HEPES, 150 mM KCl, 1 mM $MgCl_2$, and 1,3 mM $CaCl_2$, pH 7.4). Cells were then incubated with APC-labeled Annexin-V (Becton Dickinson (San Jose, Calif., USA)) for 20 minutes. Just before analysis of the samples by flow cytometry, propidium iodide (PI) (Sigma, St. Louis, Mo.) was added (final concentration 5 µg/ml). Viable cells were defined as negative for both Annexin V and PI stainings.

Results

Introduction of siRNA into Human $CD34^+$ Cells by Lentivirus-Mediated Gene Transfer Lentiviruses have two key advantages over other gene delivery systems; they can infect non-cycling cells and are not silenced during development. Several groups have described the use of small nuclear RNA promoters (H1 (Brummelkamp T R, Bernards R, Agami R. Science. 2002; 296:550-553) and U6 (Dick J E, Lapidot T, Pflumio F. Immunol Rev. 1991; 124:25-43)) for the expression of RNAi in mammalian cells. The H1 promoter was used to drive expression of siRNA designed to target the human p53 protein, and lentiviral vectors expressing the siRNA cassette were prepared (FIG. 1A). A highly enriched population of $CD34^+$ cells was isolated from human fetal liver and subsequently transduced with the siRNA/GFP expressing lentiviral vectors. The transduction efficiencies routinely ranged between 20 and 50% as indicated by the levels of GFP expression determined by flow cytometry. No obvious effect on cell growth or survival of the transduced cells was observed in vitro after culture for 3 weeks in the presence of cytokines as described above under the heading "material and methods." The proportion of $CD34^+$ derived cells expressing the GFP marker remained comparable to that of the initial population (data not shown).

To demonstrate that the introduced construct was active and able to knock down the expression of p53 in these cells, we sorted the $CD34^+$ cells after transduction based on their GFP expression. The expression of p53, which is very low in a normal situation, is upregulated very quickly after exposure of cells to several genotoxic stimuli, including gamma-irradiation. Both untransduced and control-transduced (not shown) cells responded to irradiation by increasing the levels of p53 whereas the cells expressing the p53 siRNA construct did not (FIG. 1B), demonstrating that the construct was able to silence gene expression in hematopoietic stem cells.

The Effect of Knock Down of p53 on T Cell Development and Homeostasis.

Figure 2:
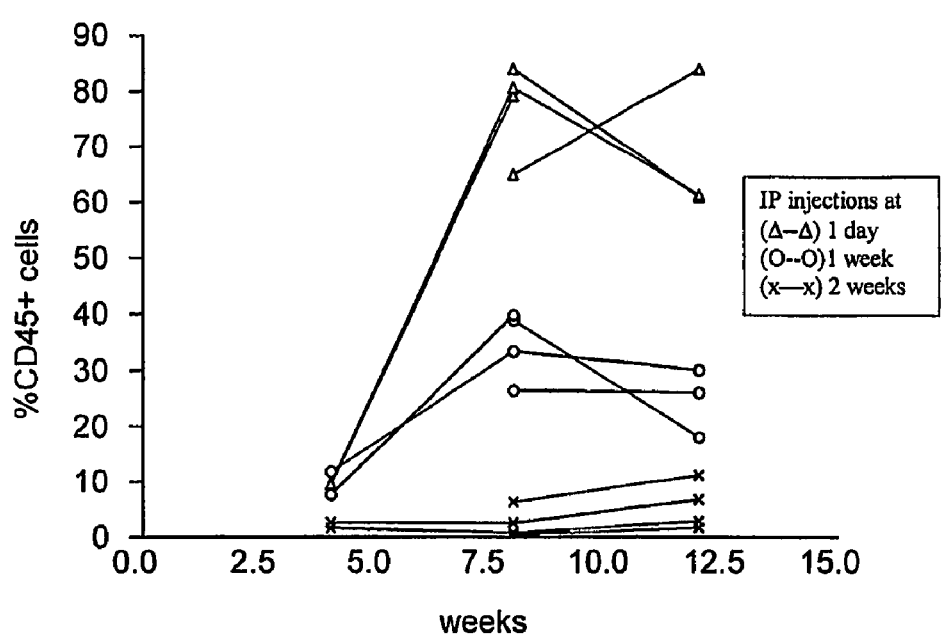
FIG. 2. Intraperitoneally engraftment of newborn RAG2$^{-/-}$ γc$^{-/-}$ mice at the age of 1 day, 1 week or 2 weeks, with CD34$^+$FL cells. Three groups of 4 new born RAG2$^{-/-}$ γc$^{-/-}$ mice, respectively 1 day (Δ-Δ), 1 week (O-O) or 2 weeks old (x-x), were intraperitoneally grafted with 0.5×106 MACS-selected CD34$^+$FL cells. At 4, 8 and 12 weeks all mice were bled and the blood was subjected to analysis by FACS to determine the percentage of CD45$^+$ human cells.

To examine the effects of p53 knock down on T cell development, we employed the human-SCID mouse model pioneered by Dick and colleagues (Dick J E, Lapidot T, Pflumio F. Immunol Rev. 1991; 124:25-43). The SOD mouse model is based on the capacity of these primitive cells (termed as SCID-repopulating cells) to repopulate the BM of C.B-17-Prkdcscid (SCID) mice (Lapidot T, Pflumio F, Doedens M, Murdoch B, Williams D E, Dick J E. Science. 1992; 255: 1137-1141) and, more recently, NOD/LtSz-Prkdcscid (NOD/SCID) mice (Pflumio F et al. Blood. 1996; 88:3731-3740; and Bonnet D et al, Nat. Med. 1997; 3:730-737) with multilineage lymphoid and myeloid cells. However, for the study of T cell development these mice have limitations, since development of T cells was only occasionally observed, apparently due to the presence of an active innate immune system in the mice. Recently, it was reported that $CD34^+$ cells upon intravenously (iv) injection into $RAG2^{-/-}$ $γc^{-/-}$ mice can develop into B cells and plasmacytoid DC (pDC) (Weijer K et al, Blood. 2002; 99:2752-2759.). In addition, we observed that T cells develop in these adult mice following iv injection of $CD34^+$ cells (results not shown). Although the success rate was 80%, it took an average of 12-16 weeks to observe a consistent T cell engraftment in the periphery. Moreover, the thymus of these mice remained small with less than $0.8 \times 10^6$ cells. Considering that thymic microenvironment of the 6-8 weeks old $RAG2^{-/-}$ $γc^{-/-}$ mice may not be optimal for human T cell development, we decided to inject human precursors at an earlier time point. Newborn (less than 1 week old), 1 week, or 2 week-old mice were injected ip with fetal liver-derived $CD34^+$ cells, and the peripheral blood was analyzed 8 and 12 weeks after injection. FIG. 2 shows that the engraftment with human cells in the periphery is higher in the less than 1 day-old mice than in older mice. Injection of one-week old mice also resulted in significant engraftment, but in two week-old mice there was no development of human cells after ip injection of $CD34^+$ cells (FIG. 2).

Analysis of 78 mice that were injected ip between day 1 and 3 after birth revealed reconstitution with human $CD45^+$ cells (Table 1) in 64 mice (83%). 32 Mice showed over 50% reconstitution, and the remainder between 10 and 50%. All mice with human $CD45^+$ cells in their peripheral blood also had T cells in the thymus and other organs.

TABLE 1

Summary of results from 12 experiments: 78 newborn mice (<1 week of age) were injected with $0.5$-$2.0 \times 10^6$ $CD34^+$ fetal liver cells intraperitoneally. Mice were bled 6-11 weeks after injection and blood was analyzed by FACS. The percentages of $CD45^+$ cells in the lymphocyte gate are given.

| % human $CD45^+$ cells in peripheral blood | Number of mice (n = 78) | % of mice |
| --- | --- | --- |
| <10% | 13 | 16 |
| 10-30% | 16 | 20 |
| 30-50% | 17 | 22 |
| >50% | 32 | 42 |

The structure of the thymus of mice that were injected ip 1 day after birth was examined by confocal microscopy 10 weeks post transplant. A differentiated thymus was observed with $CD1^+CD4^+$ and $CD4^+CD8^+$ cells in the cortex-like region and single positive $CD4^+$ and $CD8^+$ T cells in the medulla like-region (results not shown).

Figure 3:
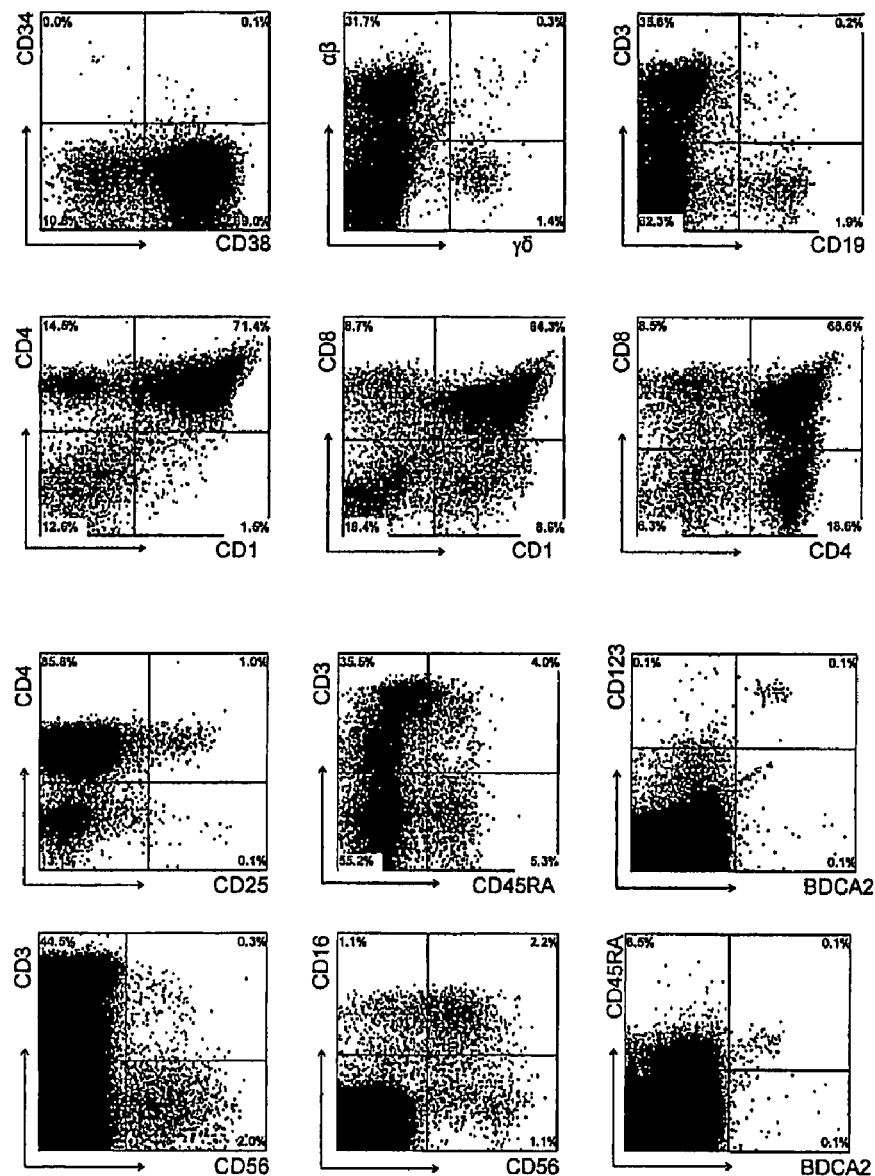
FIG. 3. Repopulation of thymus of RAG2$^{-/-}$ γc$^{-/-}$ mice, 11 weeks after ip injection with CD34$^+$ hematopoietic stem cells from fetal liver. FACS profiles of thymus: Thymocytes were stained with antibodies against stem cell markers CD34 and CD38, T cell markers TCR alpha beta and TCR gamma delta, CD1, CD3, CD4, CD8, CD25, CD45RA, NK cell markers CD16 and CD56, plasmacytoid DC markers CD123 and BDCA2 and B cell marker CD19. The cells in the analysis of CD16 and CD56 are not only gated on CD45$^+$ cells, but also on CD3− cells.

To further validate the newborn-mouse model, we first analyzed the T cells in the thymus and various peripheral organs in a large series of mice injected with untransduced $CD34^+$ fetal liver cells. In addition, we analyzed these mice for the presence of other leukocyte subsets. Eight to 10 weeks after injection, 2 to 10 million cells could be recovered from the thymus. An extensive flow cytometric analysis (FIG. 3) revealed the presence of all T lineage subsets, including double positive $CD4^+CD8^+$ cells and $CD4^+$ and $CD8^+$ single positive T cells. Furthermore, a subset of the $CD3^{+high}$ cells expressed $CD45RA^+$. This population represents T cells just before emigration to the periphery. Interestingly, CD25 was expressed on a subset of CD4+ T cells which are likely regulatory T (Treg) cells previously described by Stephens et al. (Stephens L A et al., Eur J. Immunol. 2001; 31:1247-1254). The observation that these CD25+CD4+ cells are also highly positive for glucocorticoid-induced tumor necrosis factor receptor family-related gene (GITR) and cytoplasmic CTLA-4 (results not shown) supports the notion that these cells represent Treg cells. In addition to TCR alpha beta+ cells and CD3+CD56+cells, the thymus also contained substantial numbers of CD3−CD56+NK cells; with about half expressing CD16. The percentage of NK cells (2%) was much higher than what is normally found in the thymus of children (<0.1%). Without being bound to theory, it is possible that the mouse thymus environment favors the generation of NK cells. Alternatively, the much higher proportion of NK cells may be a consequence of a lower expansion rate of TCR alpha beta+ cells than in a normal human thymic microenvironment. We also observed relatively high proportions of TCR gamma delta+ cells (1.5% versus less than 0.1% in a normal thymus) and B cells (2.2% versus less than 0.1% in a normal thymus), and these high percentages may be also a consequence of a low expansion rate of TCR alpha beta+ cells. In contrast to the increased percentages of NK cells, B and TCR gamma delta cells, that of BDCA2+CD123$^{high}$ pDC was within the normal range (0.1%).

Figure 4:
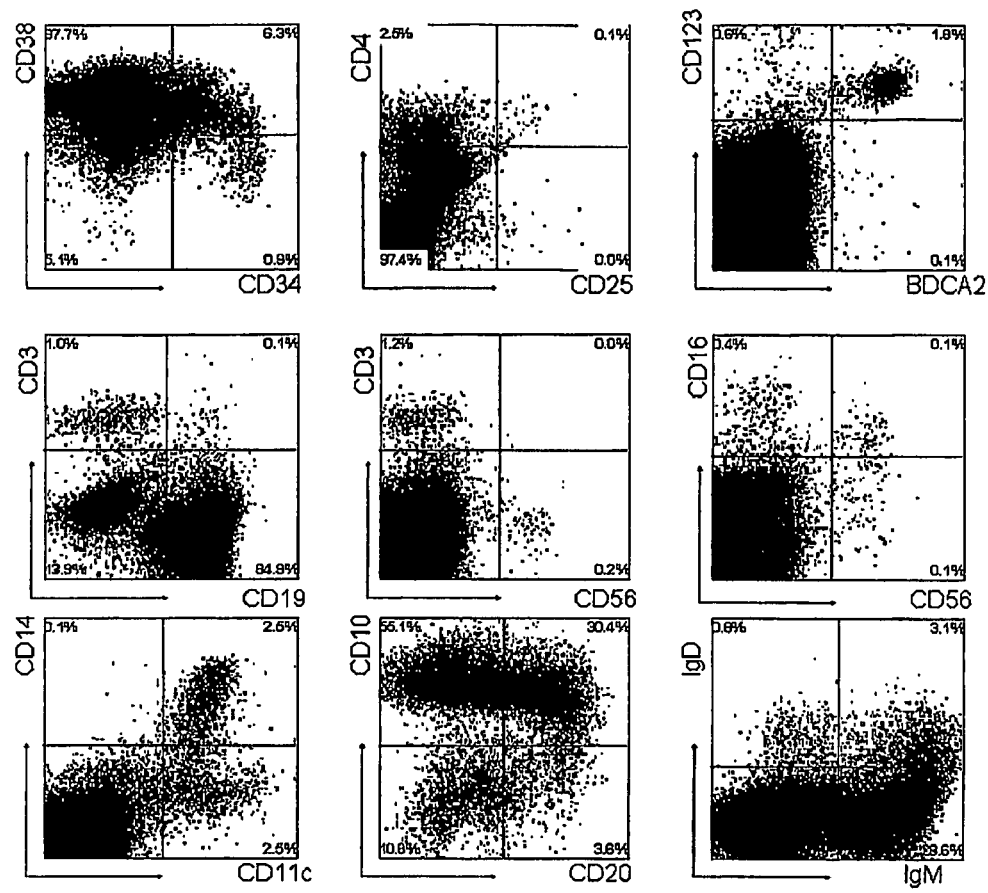
FIG. 4. Repopulation of bone marrow, spleen, liver and lung of RAG2$^{-/-}$ mice, 11 weeks after ip injection with CD34$^+$ hematopoietic stem cells from fetal liver. (A) FACS profiles of bone marrow. Bone marrow cells were stained with antibodies against stem cell markers CD34 and CD38, T cell markers CD3, CD4, CD25, NK cell markers CD16 and CD56, plasmacytoid DC markers CD123 and BDCA2, B cell markers CD11, CD19, CD20, IgM and IgD and myeloid cells markers CD11c and CD14. The cells in the analysis of IgM and IgD are not only gated on CD45$^+$ cells, but also on CD19$^+$ cells. (B) FACS profiles of spleen. Spleen cells were stained with the same antibodies as bone marrow cells. (C) FACS profiles of liver. Liver cells were stained with antibodies against stem cell markers CD34 and CD38, T cell marker CD3, plasmacytoid DC markers CD123 and CD4 and B cell marker CD19. (D) FACS profiles of lung. Lung cells were stained with antibodies against T cell marker CD3, plasmacytoid DC markers CD123 and CD4 and B cell markers CD19.
Figure 4:
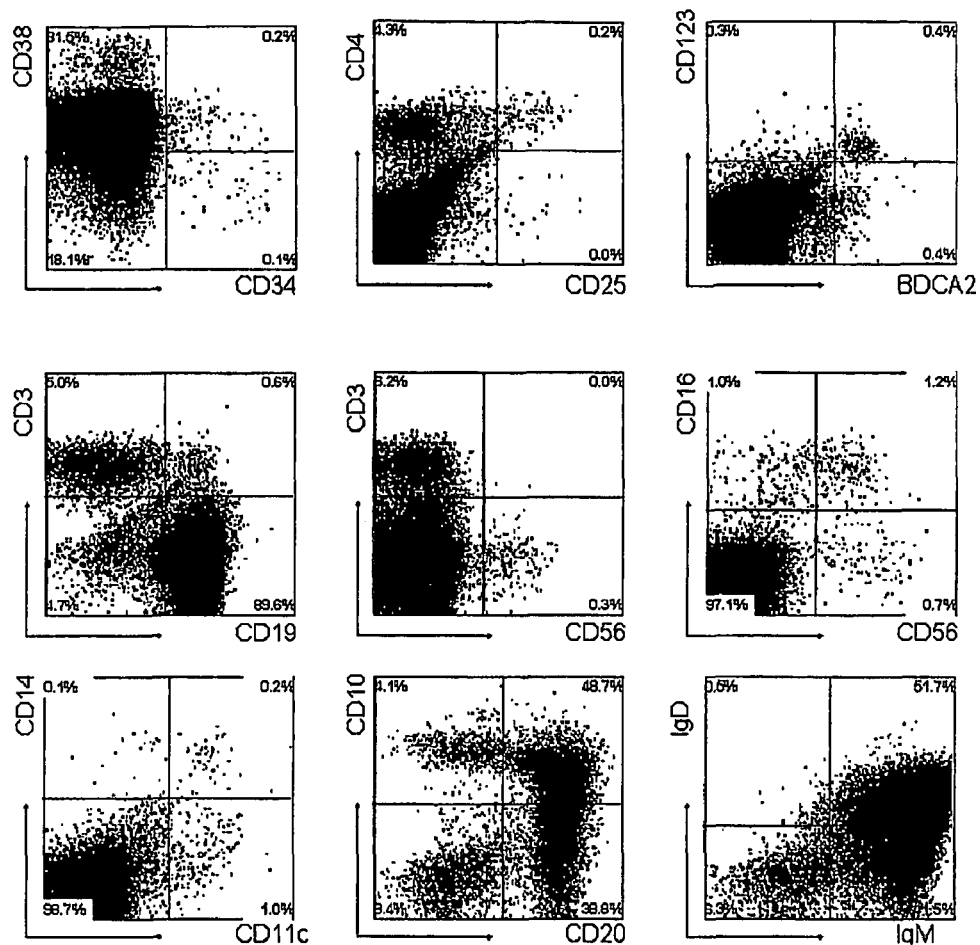
Figure 4:
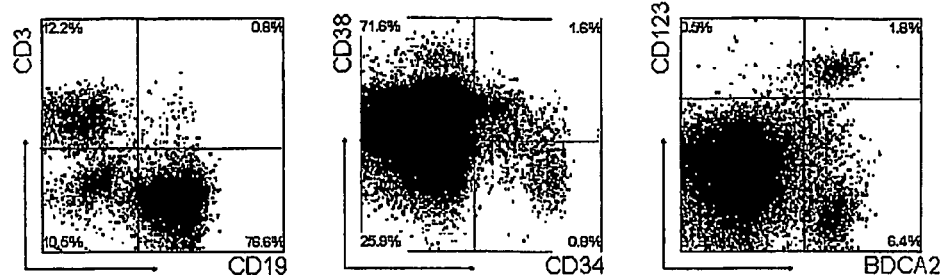
Figure 4:
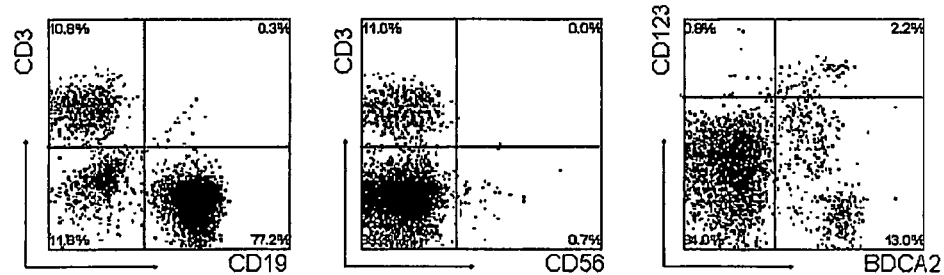

The T cells that develop in the thymus migrate to multiple anatomic locations. Variable percentages of T cells were not only found in the thymus, but also in bone marrow, spleen, liver, and lungs (FIG. 4). The bone marrow had a low proportion of T cells (1%), while in the lung this percentage was 11%. The liver and spleen contained comparable percentages of T cells. The CD4:CD8 ratios (3-4:1) were similar in all organs and were within the range normally observed in humans. Interestingly, in the spleen and bone marrow, a population of CD3+CD4+CD25+ cells could be detected which presumably contains Treg cells and recently activated CD4+ T cells. Our results show that ip injection of CD34+ cells into newborn mice results in a relatively rapid reconstitution of human T cells in the majority of the mice.

CD34+ cells developed into multiple lineages when injected into newborn RAG2$^{-/-}$ γc$^{-/-}$ mice. B cells were the most dominant cell population that developed in the peripheral blood and various organs in mice that were injected one day after birth. The highest percentage of CD19+ B cells was found in the bone marrow (FIG. 4A). Not unexpectedly, the majority of the B cells in the spleen (FIG. 4B) were CD10+ CD20+ cells and co-expressed IgM and IgD. In the bone marrow, the majority of the B cells were CD20−CD10+, suggesting that the mouse bone is the site for human B cell development. Inspection of the bone marrow (FIG. 4A) revealed the presence of CD34+ cells, a small percentage of which expressed only low levels of CD38, suggesting that some primitive CD34+CD38$^{dim}$ progenitor cells remain in their undifferentiated state.

Significant numbers of pDC were found in all organs; pDC were most clearly present in the bone marrow (FIG. 4A) and liver (FIG. 4C), but were also present in the lungs (FIG. 4D). NK cells could also be detected in peripheral blood and various organs, but the percentages were, in general, much lower than in the thymus. CD11c and CD14+ monocytes were observed in the organs (FIG. 4), indicating that, not only human lymphoid, but also human myeloid development took place in these mice.

We then injected a series of mice with CD34+ fetal liver cells transduced with p53 siRNA or with an empty vector. Table 2 shows that the percentages of thymocytes in GFP+ and GFP− cells were similar both in the mice injected with p53 siRNA or control-transduced CD34+ cells. Similarly, we could not detect significant (conclusive) differences in the periphery of these animals when liver or spleen cells were analyzed. Thus, we conclude that inactivation of p53 does not lead to a survival advantage of p53 siRNA expressing peripheral T cells.

TABLE 2

| Mouse | Construct | GFP+ | GFP− |
|---|---|---|---|
|  |  | Percentage of CD3+ cells |  |
| n = 1 | p53i | 25.2 | 22.1 |
| n = 2 | p53i | 97.2 | 94.8 |
| n = 3 | p53i | 87.7 | 96.3 |
| n = 4 | p53i | 99.4 | 94 |
| n = 5 | p53i | 56.7 | 33.2 |
| n = 6 | p53i | 68.3 | 85.8 |
| n = 7 | p53i | 98.7 | 53.6 |
| n = 1 | control | 25.9 | 32.4 |
| n = 2 | control | 97.4 | 95.5 |
| n = 3 | control | 95.7 | 76 |

Figure 5:
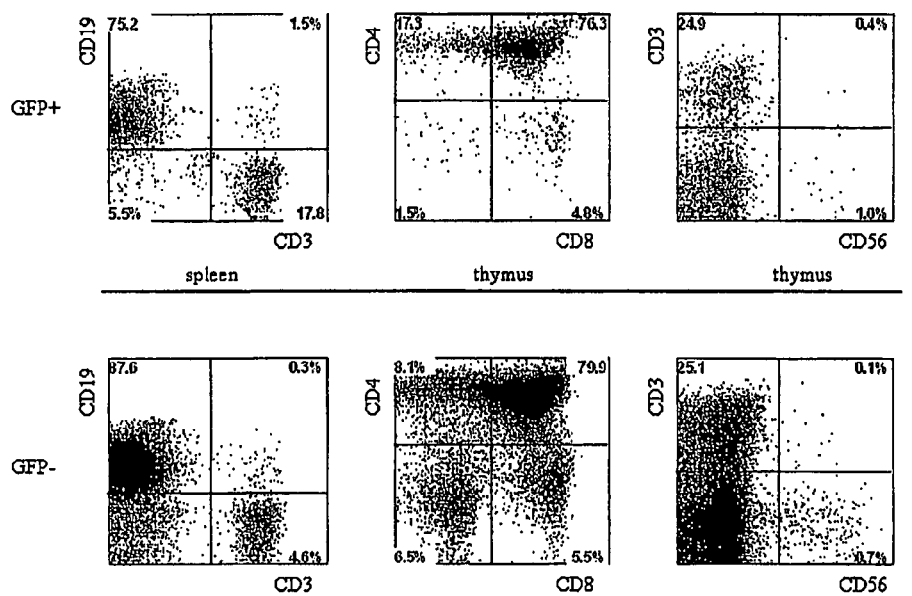
FIG. 5. Multilineage presence of GFP$^+$ expressing cells in mice transplanted with lentivirus transduced human hematopoietic progenitors. New born RAG2$^{-/-}$ γc$^{-/-}$ mice were ip injected with human CD34$^+$ hematopoietic stem cells isolated from fetal liver and transduced with the pTRIPΔU3-EF1alpha p53 RNAi lentivirus. Mononuclear cell suspensions from the thymus and spleen of these mice were stained with various human-specific monoclonal antibodies and analyzed by flow cytometry. Cells positive for human CD45 were gated and further analyzed comparing the GFP positive and negative populations. Examples of T cell development in thymus and spleen are given. Cells are stained with antibodies directed to CD3, CD4, CD8 and CD56 and analyzed by FACS.

Inspection of the thymus of mice injected with p53 siRNA and control-transduced cells revealed the presence of GFP+ cells in the CD4CD8 double negative, double positive and single positive T cell compartments. However, we did not observe differences in the phenotypes of any of the subsets of T and non-T cells in the thymus (FIG. 5A) when gating on p53 siRNA-GFP+, on untransduced cells (GFP−) or control-GFP+ (not shown). Also, we did not observe differences in the presence of T cells in any of the p53 siRNA-GFP+, or on untransduced cells in the spleen (the phenotypes of T cells of a representative mouse are shown in FIG. 5).

Figure 6:
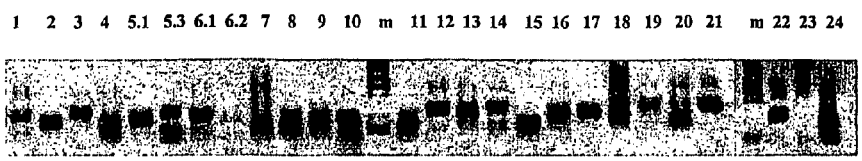
FIG. 6. V beta family representation from p53i GFP$^+$ expressing T cells in mice transplanted with lentivirus-transduced human hematopoietic progenitors.

Given the important role of p53 in the control of cell proliferation and induction of apoptosis in response to DNA damage, it was of interest to know if the reduced levels of p53 may have an effect in the composition of the TCR repertoire. We investigated the TCR diversity in T cells isolated from mice injected with CD34+ cells transduced with the p53i construct. By PCR analysis, we could establish that all the Vbeta families were represented in the repertoire (FIG. 6). Furthermore, detailed analysis of the CDR3 region clearly demonstrate that the peripheral T cells present in these mice are polyclonal (data not shown), indicating that downregulation of p53 during T cell development does not result in prevalence of some clones.

Figure 7:
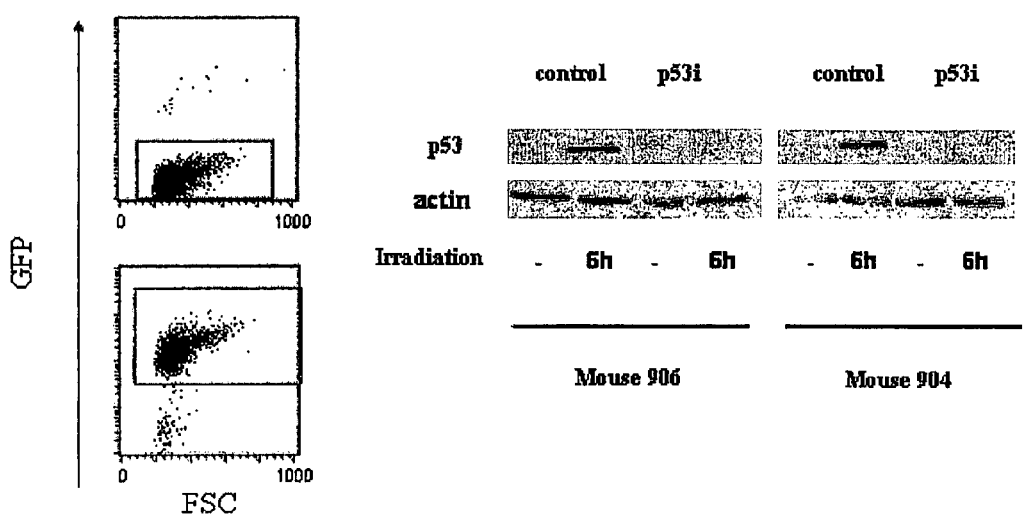
FIG. 7. The lentivirus construct is present and active in mature cells derived from transduced human CD34$^+$ precursors. (A). T cells were isolated from spleen and peripheral blood of mice reconstituted with transduced human CD34$^+$ cells, expanded in vitro and sorted based on the expression of GFP. Cells were then gamma-irradiated and six hours later whole-cell extracts were prepared, separated on 10% SDS-polyacrylamide gel electrophoresis and immunoblotted to detect human p53. A western blot with antibody against beta-actin was used as a control. Results from two animals are shown. (B) T cells expressing the p53i or control-GFP constructs were treated with different stimuli and assayed 24 hours later for apoptosis induction using a combination of propidium Iodine (PI) and Annexin V double staining and flow cytometry. Double negative cells represent the viable population (indicated by the percentages).
Figure 7:
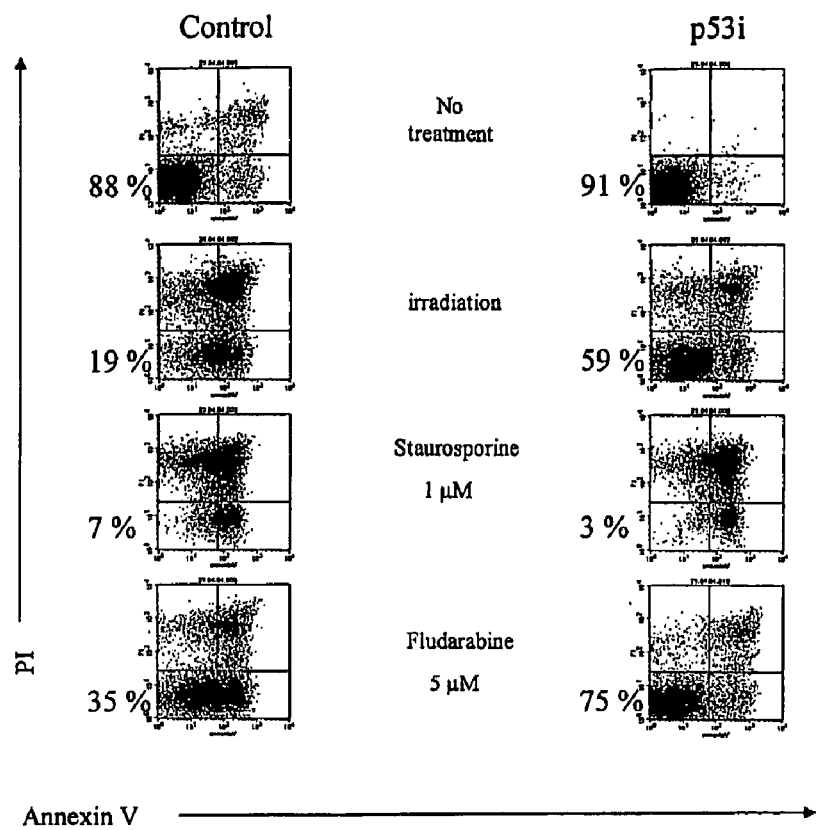

To interpret these results, it was important to verify the stable expression and efficiency of the construct in knocking down the expression of p53 in cells isolated from the periphery of these animals. Human mononuclear cells, isolated from the spleens and blood of mice transplanted 10 weeks earlier with transduced CD34+ cells, were cultured in the presence of human PBMC from two different donors, the EBV cell line JY, PHA and IL-2. Under these conditions, T cells proliferated extensively. Since only mature T cells can be expanded using this protocol (Res P et al, J Exp Med. 1997; 185:141-151), our data indicate that the human T cells that developed in the RAG2$^{-/-}$ γc$^{-/-}$ mice were functionally mature and could respond to signals triggered by TCR ligation. In addition, the T cells were capable to respond to alloantigens and to produce a broad array of cytokines upon restimulation in vitro, indicating that they were able to recognize and respond to foreign antigens (data not shown). After expansion of the T cells derived from the p53 siRNA transduced CD34+ cells in vivo, we sorted the GFP+ and GFP− T cells, and tested the levels of p53 after gamma-irradiation from two different reconstituted animals. In both mice, p53 increased in the non-transduced population, whereas the p53 levels in cells containing the p53 siRNA construct remained almost undetectable (FIG. 7A). Consequently, these p53 siRNA+ cells are less susceptible to apoptosis induced by gamma-irradiation or treatment with fludarabine (FIG. 7B). Hence, these p53 siRNA+ cells are stabilized. In contrast, loss of p53 did not affect the sensitivity of T cells to apoptosis induced by dexamethason and staurosporine, which are p53-independent apoptosis-inducing agents (FIG. 7 and data not shown).

Figure 8:
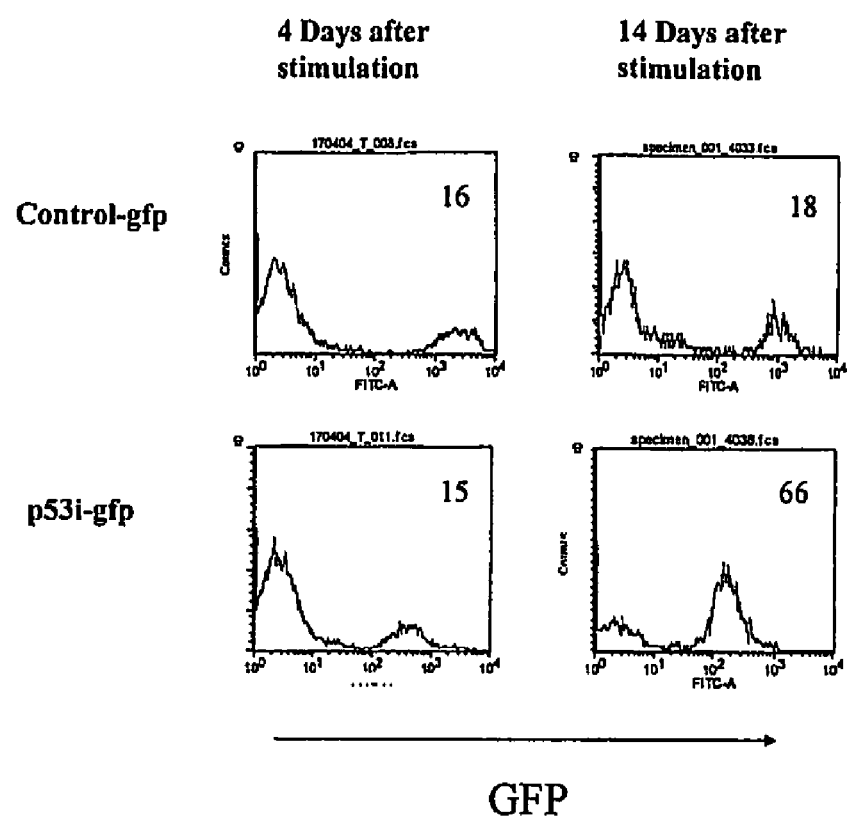
FIG. 8. Reduced content of p53 favors the outgrowth of mature T cells derived from human CD34$^+$ precursors. T cells were isolated from spleen and peripheral blood of mice reconstituted with transduced human CD34$^+$ cells and expanded in vitro as described in material and methods of example 1. The percentage of GFP positive cells was established by flow cytometry at two different time points after stimulation.

In addition to its pro-apoptotic function, p53 is also involved in the induction of growth arrest in response to different stimuli. Moreover, p53 is a negative regulator of hTERT, which regulates the replicative life span of T cells (Roth A et al, Blood. 2003; 102:849-857). We studied the growth of the p53 siRNA-expressing cells after TCR stimulation. The presence of GFP in our constructs allowed us to examine the dynamics of a population of T cells transduced either with p53i or with a control construct in relation to untransduced cells. As is shown in FIG. 8, we detected a progressive accumulation of the cells with reduced content of p53, indicating that p53 siRNA+ T cells have a growth advantage compared to the untransduced or control transduced cells. Interestingly, these differences are not detected shortly after stimulation, but only when the cells are kept in culture for a longer time period, indicating that the immediate response to TCR stimulation is similar in p53 siRNA expressing cells and controls (FIG. 8 and data not shown). These results clearly show that the p53 siRNA introduced into the CD34+ cells remained active in down modulating p53 protein in the T cell offspring. Our data also indicate that although down modulation of p53 protects the T cells against stress and upregulates hTERT, it does not affect human T cell development or homeostasis of T cells in this system.

Lack of Effect of P53 RNAi on Development of B Cells, Plasmacytoid Dc or Monocytes in Different Organs.

The fact that multiple lineages developed upon injection of CD34+ cells into new-born mice allowed us to analyze the effects of p53 knock down on development of B cells, pDC and monocytes as well. In table 3, it is shown that the percentages of B cells in the GFP+ and the GFP− populations are similar in cells developed from the control-GFP and p53 siRNA-GFP-transduced CD34+ cells. In addition, no differences in expression of B cell differentiation markers were noted between untransduced control-GFP and p53 siRNA-GFP cells (FIG. 9).

Figure 9:
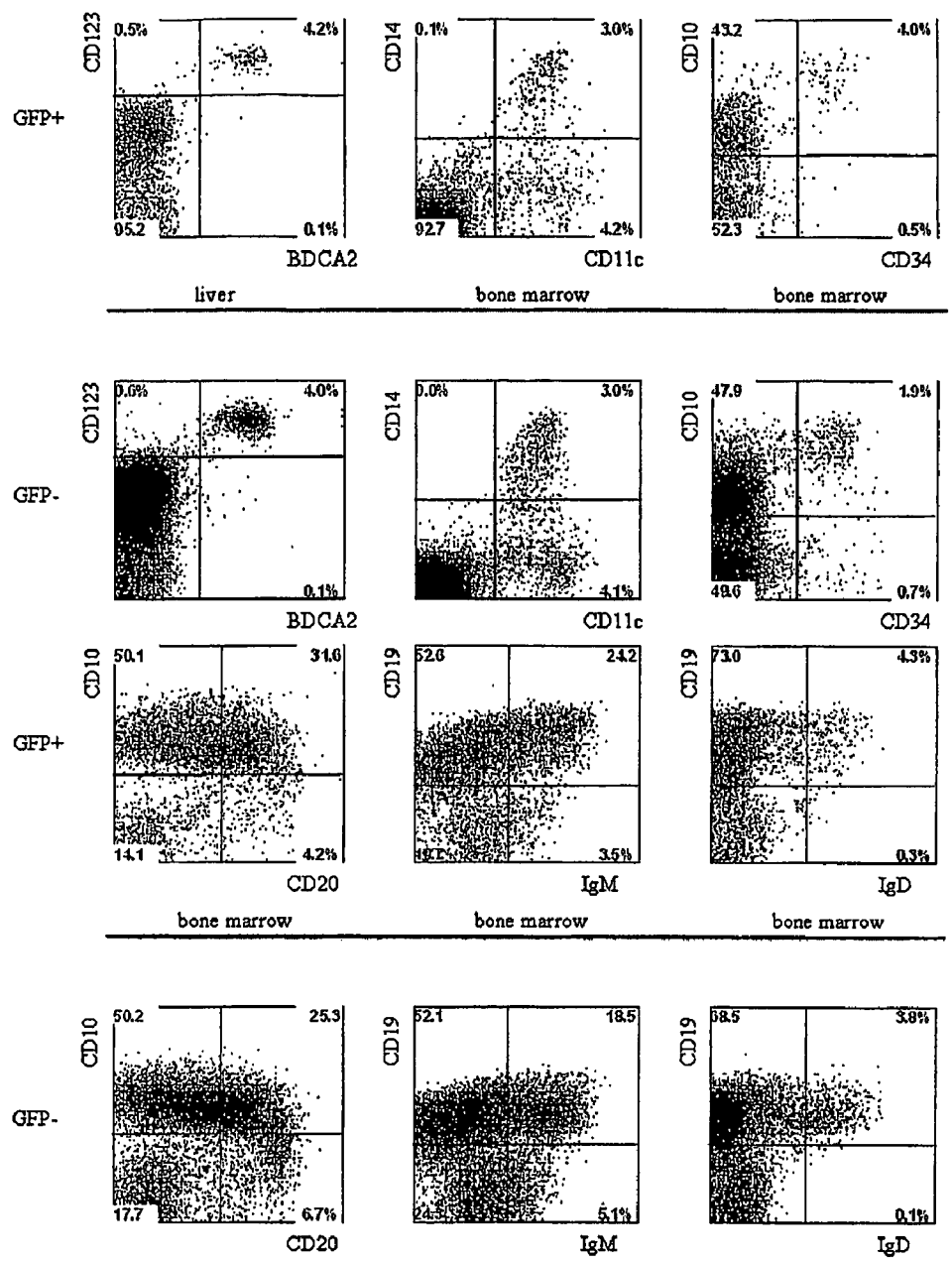
FIG. 9. Multilineage presence of GFP$^+$ expressing cells in the bone marrow and liver of mice transplanted with lentivirus-transduced human hematopoietic progenitors. Newborn RAG2$^{-/-}$ γc$^{-/-}$ mice were ip injected with human CD34$^+$ hematopoietic stem cells isolated from fetal liver and transduced with the pTRIPΔU3-EF1alpha p53 RNAi lentivirus. Mononuclear cell suspensions from the liver and the bone marrow of these mice were stained with various human-specific monoclonal antibodies and analyzed by flow cytometry. Cells positive for human CD45 were gated and further analyzed comparing the GFP positive and negative populations. Examples of plasmacytoid DC, myeloid and B cell development are shown. Liver and bone marrow cells are stained with antibodies directed to CD123, BDCA2, CD11c, CD14, CD10, CD34, CD10, CD19, CD20, IgM and IgD.
Figure 10:
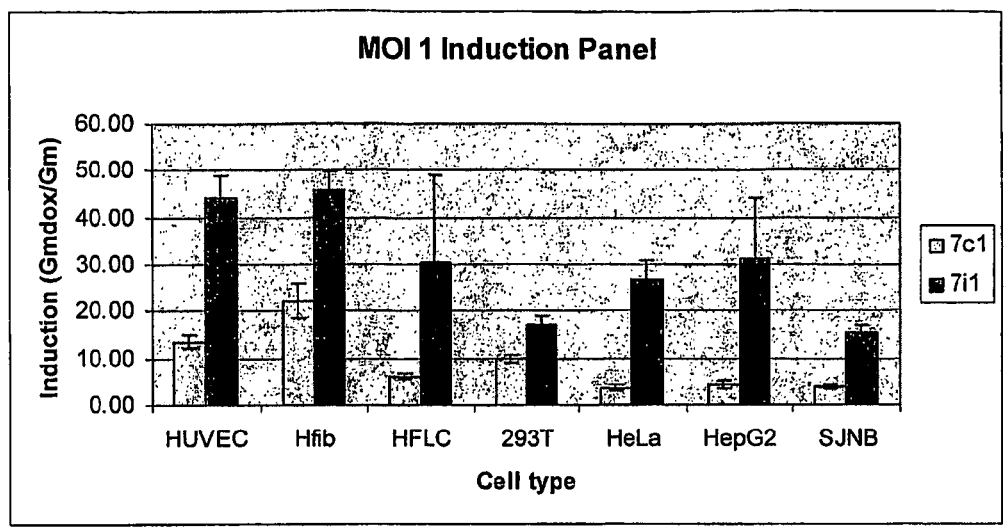
FIG. 10. Cell panel 7TetOmCMV CMV vs IRES.

Moreover, we could also demonstrate that knocking down p53 had no effect on development of pDC and monocytes, as the percentages of these cells in the GFP+ populations were very similar in untransduced, the control-transduced, as well as in the p53 siRNA transduced samples (FIG. 9).

TABLE 3

| Mouse | Construct | GFP+ | GFP− |
|---|---|---|---|
| | | Percentage of CD19+ cells | |
| n = 1 | p53i | 48.7 | 44.2 |
| n = 2 | p53i | 83.2 | 81.5 |
| n = 3 | p53i | 78 | 80.9 |
| n = 4 | p53i | 26.7 | 75.8 |
| n = 5 | p53i | 80.1 | 76.3 |
| n = 6 | p53i | nd | nd |
| n = 7 | p53i | 75.9 | 62.2 |
| n = 1 | control | 27.7 | 44.8 |
| n = 2 | control | 69.8 | 73.9 |
| n = 3 | control | 63.6 | 67.6 |

Discussion

We show here that the newborn RAG2$^{-/-}$ γc$^{-/-}$ mouse is suitable for generating stabilized human cells of interest. A robust T cell development was observed upon ip injection of CD34+ cells into new-born mice which proceeded at an accelerated pace compared to what was observed previously with adult mice. Besides main-stream CD4+ and CD8+ T cells, all the other subsets of T cells could be observed, including TCR gamma delta cells, CD3+CD56+ T cells and CD25+CD4+ cells that could represent Treg cells. We also observed development of B cells, NK cells, pDC and monocytes in the circulation and peripheral organs of the mice injected with CD34+ cells. In addition, CD15+CD11c+CD24+ granulocytes and a low but consistent percentage of human glycophorin positive cells were present (manuscript in preparation). Together, these data indicate the generation of a rather complete repertoire of human leukocytes in these mice, demonstrating that these newborn double KO mice are suitable for studying "human" immune responses in vivo.

By using siRNA directed against p53 in a lentiviral vector that contained the marker GFP under control of an independent promoter, we demonstrated the feasibility of GFP to track development of genetically modified CD34+ precursors in vivo. Biochemical analysis revealed that, in CD34 precursors, the p53 siRNA expression results in >95% reduction in gamma-irradiation-induced p53 expression. Since we found that the siRNA construct remained stably and functionally expressed in the T cell progeny, it is demonstrated that the siRNA remains expressed during differentiation of CD34+ cells into mature leukocytes.

p53 siRNA+ T cells isolated from the mice, showed in vitro growth advantage in comparison to control-transduced or untransduced T cells. We demonstrated that downmodulation of p53 renders human T cells resistant to gamma-irradiation. Hence, downmodulation of p53 results in stabilization of cells.

Example 2

A single Lentiviral vector with dox-dependent transgene expression is designed. In our design, we evaluate placing rtTA under constitutive expression of the CMV promoter, or autoregulatory expression by placing rtTA downstream of the TRE and GFP using an IRES element. An evaluation of both vector systems on a panel of human primary and established cells lines indicate that the autoregulatory loop has lower basal transgene activation, higher transgene induction. It is furthermore shown that the induction kinetics for the autoregulatory loop are faster than that of a constitutively expressed rtTA and appear to be better tolerated upon long term culturing and repeated cycles of induction.

Subsequently, rtTA2-S2 is replaced by a recently published virally evolved rtTA (Das A T et al, Journal of Biological Chemistry 2004; 279:18776-18782) that we call rtTA3. This newly described rtTA3 has both a 13-fold higher sensitivity to dox as compared to wild type rtTA, and has higher transcriptional activation and induction for a broad range of dox concentrations compared to rtTA2-M2. Introduction of rtTA3 within the autoregulatory loop allows for activation of the loop at lower concentrations of dox and allows for a dox dependent graded expression of GFP with a maximal expression reached at a dox concentration of 100 ng/mL.

Materials and Methods:
Reagents:
Dox (Sigma). Stock solutions were made by dissolving dox 10 mg/ml in water and filter sterilized. Stocks were kept frozen at −20° C.

Lentiviral Vector Preparation

Lentiviral vectors were prepared as previously reported (Seppen, J, Rijnberg, M., Cooreman, M. P., and Oude Elferink, R. P. (2002). Lentiviral vectors for efficient transduction of isolated primary quiescent hepatocytes. J Hepatol 36, 459-65). Briefly, HEK 293T cells were transfected using the Calcium Phosphate precipitation with a third generation lentiviral vector system containing four plasmids. 24 hours following transfection, the media was replaced supplemented with 25 mM HEPES pH 7.4. Virus containing supernatant was collected 48 hours following transfection, alliquoted, and frozen at −80° C.

Cell Lines and Culturing

HEK293T, HeLa, HepG2, SJNB-8, HUVEC, Human Fibroblasts, Human Fetal Liver cells. All were cultured in standard DMEM media supplemented with 10% fetal bovine serum, penn/strep, glutamine.

Virus Titer and Transduction

Viral titers were determined by transduction of HeLa cells. Briefly, virus is added in serial dilutions to HeLa cells supplemented with DEAE Dextran and transduced for four hours. 72 hours following transduction, cells are harvested and GFP expression is measured by flow cytometry to calculate virus titers. Titers were determined by induction with 1000 ng/ml dox.

SDS-Page and Western Blotting

Sds Page and Western Blotting were Performed as Described: Seppen, J., R. R. van der, N. Looije, N. P. van Til, W. H. Lamers, and R. P. Oude Elferink. (2003). Long-term correction of bilirubin UDPglucuronyltransferase deficiency in rats by in utero lentiviral gene transfer. Mol. Ther. 8:593-599.

Results:

Our initial attempts at constructing a single Tet-On lentiviral vector was an adaptation from a previously described tet-dependent conditionally replicating HIV-1 (Verhoef et al, 2001), which contained two repeats of the TetO located within the viral LTR. As reported in Table 4, we were unable to obtain high viral titers with these vectors. We then proceeded to use the TRE consisting of seven repeats of the TetO fused to a minimal CMV promoter in the backbone of a third generation lentiviral vector containing the central polypurine tract (cPPT) and hepatitis B post transcriptional regulatory element (PRE) (Barry et al, 2001). With these new vectors, we were able to increase viral titers 1 to 2 orders of magnitude, and specifically with the autoregulatory loop vectors to obtain viral titers comparable to those obtained using a constitutive promoter to drive transgene expression. (data not shown).

TABLE 4

Titers of Inducible Lentiviral vectors

| Virus | Titers |
|---|---|
| TetO located in LTR | |
| LTRtetO CMV rtTA-S2 | $1.56 \times 10^4 \pm 1.25 \times 10^4$ |
| LTRtetO IRES rtTA-S2 | $4.18 \times 10^3 \pm 8.52 \times 10^2$ |
| LTRtetO IRES rtTA3 | $1.03 \times 10^5 \pm 7.71 \times 10^4$ |
| Constitutive rtTA expression | |
| TetO$_7$mCMV CMV rtTA-S2 | $2.15 \times 10^5 \pm 1.41 \times 10^5$ |
| TetO$_7$mCMV CMV rtTA3 | $1.18 \times 10^5 \pm 6.55 \times 10^4$ |
| Autoregulatory loop rtTA | |
| TetO$_7$mCMV IRES rtTA-S2 | $1.0 \times 10^6 \pm 2.51 \times 10^5$ |
| TetO$_7$mCMV IRES rtTA3 | $1.25 \times 10^6 \pm 3.66 \times 10^5$ |

A panel of human primary and established cell lines were transduced at a multiplicity of infection (MOI) of 1 with either 7C1 or 7I1 and were induced with a dox concentration of 1000 ng/ml. Induction levels were measured as GFP expression with dox divided by GFP expression without dox, and reflect both overall gene expression levels and basal expression. In all cell lines tested, the autoregulatory loop gave higher levels of induction compared to constitutive expression of rtTA (table 5).

TABLE 5

Fold induction of TetO$_7$mCMV CMV rtTA-S2 (7C1) vs TetO$_7$mCMV IRES rtTA-S2 (7I1)

| Virus | HUVEC | Fibroblast | HFLC | 293T | HeLa | HepG2 | SJNB |
|---|---|---|---|---|---|---|---|
| 7C1 | 13.55 ± 1.25 | 22.15 ± 3.75 | 6.06 ± 0.70 | 9.82 ± 0.76 | 3.72 ± 0.52 | 4.19 ± 0.77 | 3.95 ± 0.27 |
| 7I1 | 44.02 ± 4.93 | 45.81 ± 3.77 | 30.27 ± 18.85 | 17.01 ± 1.95 | 26.72 ± 4.22 | 31.14 ± 13.00 | 15.28 ± 1.61 |

We designed the autoregulatory loop such that we expected low basal expression of rtTA without induction. To evaluate this, we transduced early passage primary human fibroblast at a MOI of 1 with either Lenti TetO$_7$mCMV CMV rtTA-S2 or Lenti TetO$_7$mCMV IRES rtTA-S2. Following expansion, the cells were untreated or treated with 1000 ng/ml dox for 72 hours and then harvested for generating lysates.

Figure 11:
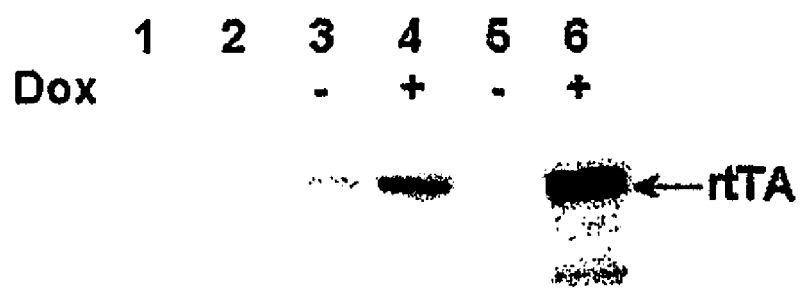
FIG. 11. rtTA Western blot Human Fibroblasts MOI 1 transduced Western blot of HeLa lysates. Lane 1 mock transduced cells, 2 Lenti pgk eGFP, 3,4 TRE d2eGFP CMV rtTA2-S2, 5,6 TRE d2eGFP IRES rtTA2-S2.
Figure 12:
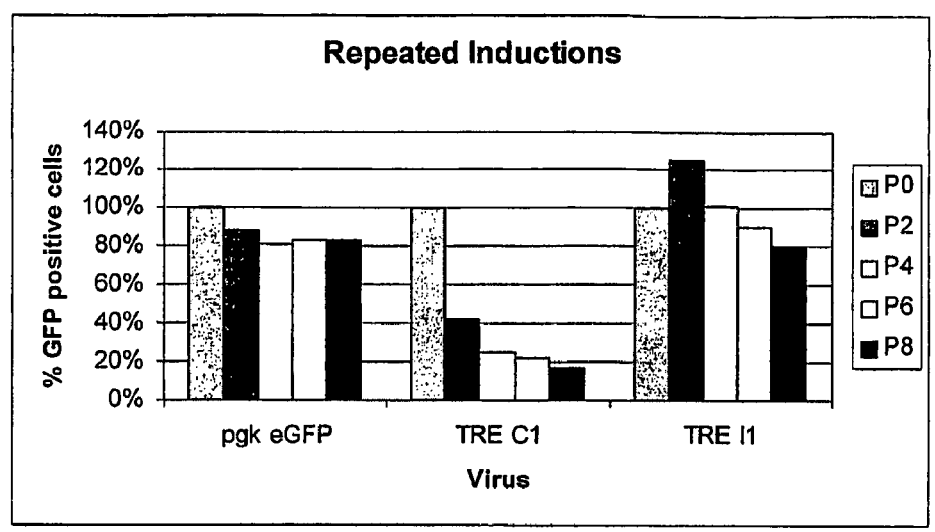
FIG. 12. Repeated induction results MOI 0.1 HeLa. HeLa cells were transduced at a MOI of 0.1 with either pgk eGFP, TRE d2eGFP CMV rtTA2-S2, or TRE d2eGFP IRES rtTA2-S2. The number of GFP positive cells detected upon first induction was set to 100% with all other measurements normalized to the first induction.

In the absence of doxycycline, we were unable to detect the expression of rtTA in the autoregulatory loop (FIG. 11 lane 5), confirming that basal expression of rtTA in our autoregulatory loop system was indeed extremely low, while we could clearly see expression of rtTA in the constitutively expressing virus FIG. 11 lane 3.

Repeated Induction on HeLa 7C1 vs 7I1

We next evaluated both systems for the ability to go through repeated cycles of induction by transducing HeLa cells at a MOI of 0.1 with either 7C1 or 7I1, and alternating induction and withdrawal of dox where each passage represents either an on or off state. As a control, we included HeLa cells transduced with lenti pgk eGFP at an MOI of 0.1. The percentage of GFP positive cells following one cycle decreased by more than 50%, and after several cycles of induction fell to 20% of starting values, while levels for the IRES rtTA2-S2 transduced cells remained stable compared to the pgk eGFP control, indicating that autoregulatory regulation of rtTA is better tolerated because toxicity of rtTA is avoided.

Figure 13:
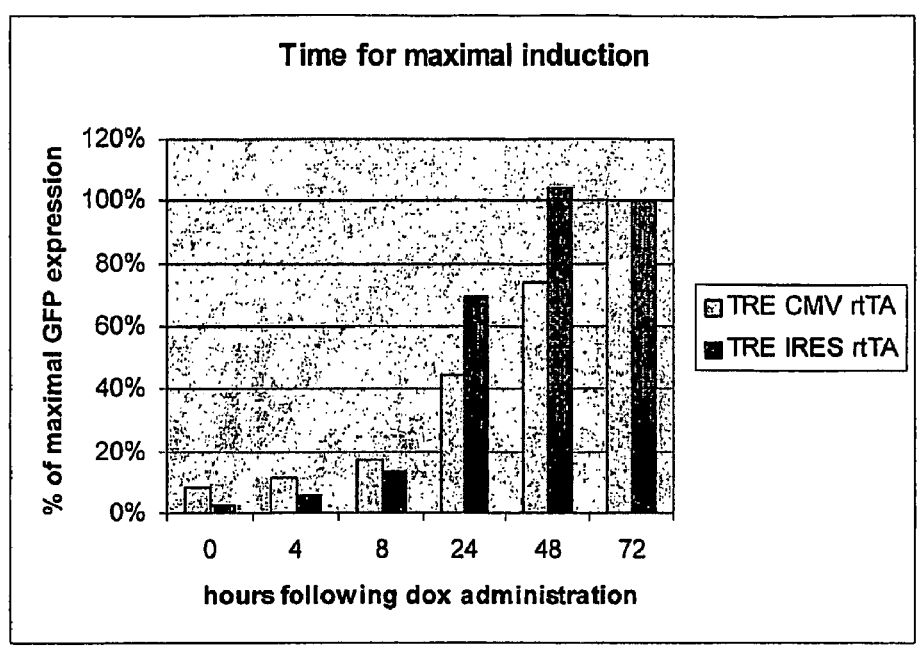
FIG. 13. Time for maximal GFP expression. MFI at 72 hours was set as maximum level of induction and all other values are based as a percentage of this value.

Another concern with using autoregulatory expression of rtTA was that the time for maximal activation would be considerably slower as compared to constitutive expression. To determine the time for maximal induction we transduced HeLa cells at an MOI of 1 with either TRE d2eGFP CMV rtTA2-S2 or TRE d2eGFP IRES rtTA2-S2 and added dox (1000 ng/ml) at fixed time points. We found that there was no increase in GFP expression following 72 hours (unpublished observations), so we set this time as the arbitrary level for maximal expression. As can be seen in FIG. 13, autoregulatory expression of rtTA reaches a maximal level faster than constitutively expressed rtTA (24 hours 70% vs. 45% of max and 48 hours 100% vs. 75%). These results indicate that, not only is there no loss in induction time using an autoregulatory loop, but that we reach maximal expression faster as compared to a constitutively expressed rtTA.

Figure 14:
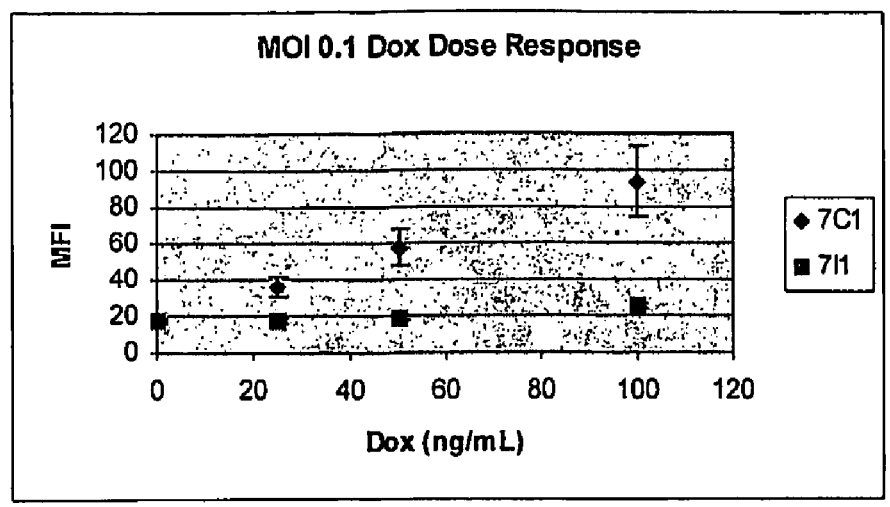
FIG. 14. Concentration (dox dose response) 7C1 and 7I1 Human Fib MOI 0.1.
Figure 14:
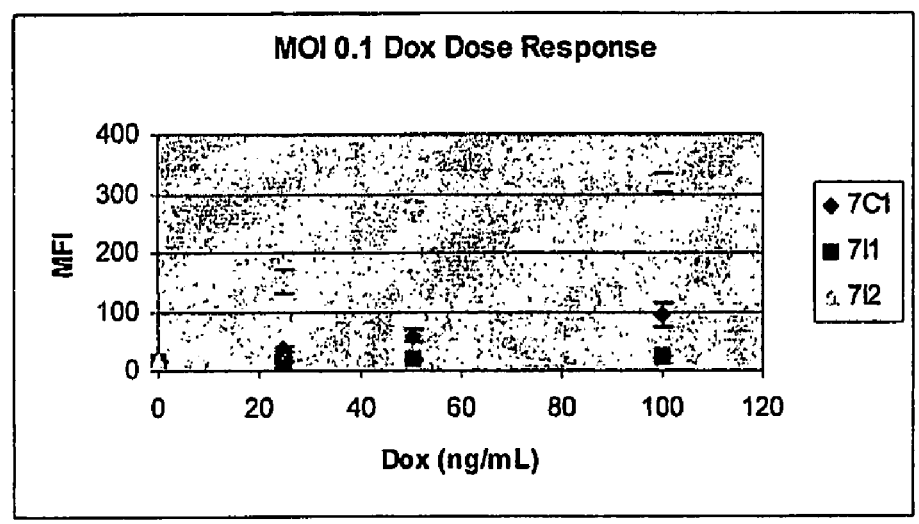

An important feature of regulated gene expression is to have a correlation between the concentration of the inducer molecule and the level of transgene expression. We compared the level of GFP expression between the two different systems over a range of dox concentrations (0 to 1000 ng/ml). We observed that at lower dox concentrations we were unable to turn on GFP expression with the autoregulatory loop (FIG. 14 panel A). The autoregulatory loop requires higher concentrations of dox for startup because of the very low expression of rtTA2-S2 under basal conditions. We hypothesized that the rtTA2 S2 was not sensitive enough to dox to activate the loop when using low concentrations of dox. To test this idea, we replaced the rtTA2-S2 with a mutant rtTA, rtTA3, containing three amino acid substitutions described by (Urlinger S et al; Proc. Natl. Acad. Sci. (2000) Vol 97, No 14, 7963-7968 and Das A T et al, Journal of Biological Chemistry 2004; 279: 18776-18782), which has a 13-fold greater sensitivity to dox as compared to wild type rtTA and improved transcriptional activation. For further discussion, this rtTA mutant will be referred to as rtTA3. When we introduced rtTA3 into the autoregulatory, we saw a graded expression of GFP over a range of dox concentrations tested with a maximal level of expression obtained at 100 ng/ml dox (FIG. 14 panel B).

Example 3

This example shows a role of STAT5 in regulation and proliferation of B cells.
Materials and Methods
B Cell Isolation B cells were obtained from tonsils or peripheral blood of adults. Tonsillectomies were performed in the department of surgery for children of the Free University of Amsterdam. T cells were depleted using anti-CD4 and anti-CD8 conjugated microbeads (Miltenyi Biotec, Amsterdam, The Netherlands). Next, the cells were incubated with anti-CD19 FITC conjugated (DAKO, Glostrup, Denmark) and anti-CD3 phycoerythrin (PE) conjugated (Becton Dickinson), followed by sorting of the CD19$^+$CD3$^-$ population using the MoFlo (Cytomation/DAKO, Glostrup, Denmark) or FacStarPlus (Becton Dickinson, San José, Calif.). The resulting B cells were >99% pure upon reanalysis.
Retroviral Constructs and Production of Recombinant Retrovirus Constitutive active mutants of STAT5a and b have been described previously (Ariyoshi et al., 2000; Onishi et al., 1998). DNAs encoding these mutants and wildtype STAT5b were obtained from T. Kitamura (IMSUT, Tokyo, Japan). BCL-6 was identified in a senescence rescue screen in murine fibroblasts as an inhibitor of anti-proliferative p19ARF-p53 signaling (Shvarts et al., 2002). These DNAs were ligated into LZRS-linker-IRES-GFP vector that was described previously (Heemskerk et al., 1997; Heemskerk et al., 1999). For knock down experiments, the pSUPER construct previously described by Brummelkamp et al. (Brummelkamp et al., 2002) was adapted. To allow identification of transduced cells by flow cytometry, a GFP expressing cassette was added to the pSUPER construct such that the pol3 promoter for the transcription of the siRNA probe and the PGK promoter driving GFP expression are in opposite direction. The siRNA sequences specifically targeting STAT5 (1365: 5'-GCAGCA-GACCATCATCCTG-3' (SEQ ID NO:19); 1668 3'-GAC-CCAGACCAAGTTTGCA-5' (SEQ ID NO:20)) and BCL-6 (789 5'-TGTGTGCCACAGCAATATC-3' (SEQ ID NO:21); 970 3'-GATGAGATTGCCCTGCATT-5' (SEQ ID NO:22)) mRNA were designed using the Ambion homepage (on the worldwide web at: ambion.com). Sequences were inserted into the BglII-HindIII sites of pSUPER-GFP. Subsequently, the pol3-siRNA-pgk-GFP cassette was subcloned into the self-inactivating derivate of the LZRS retroviral construct.

The retroviral plasmids were transfected into a helper-virus free amphotropic producer cell line Phoenix-A, a derivative of the human embryonic kidney cell line 293 (Kinsella and Nolan, 1996) (a kind gift of Dr. G. Nolan, Stanford University, Palo Alto, Calif.), using Fugene-6 (Roche Diagnostics Netherlands, Almere, Netherlands) according to manufacturers protocols. Two days later, selection of transfected cells started by the addition of 2 µg/ml puromycin (Becton Dickinson Clontech Laboratories, Palo Alto, Calif.). Ten to 14 days after transfection, 6×10$^6$ cells were plated per 10 cm Petri dish (Becton Dickinson Discovery Labware, Bedford, Mass.) in 10 ml complete medium (Iscove's medium (Life Technologies BV, Breda, The Netherlands), 8% Fetal Calf Serum (FCS), Penicillin, Streptomycin) without puromycin. The next day, the medium was refreshed, and on the following day retroviral supernatant was harvested, centrifuged and frozen in cell free aliquots at −70° C. This approach affords a reproducible rapid, large scale and high titer retroviral production of over 3×10$^6$ infectious virus particles/ml.

The CA and wildtype (WT) STAT5b estrogen receptor (ER) fusion constructs were made as follows: A PCR was performed with either the N604H STAT5b mutant (Ariyoshi et al., 2000; Onishi et al., 1998) or wildtype STAT5b cDNAs to introduce a BglII site in lieu of the stop codon. A XhoI/BglII digestion product was generated, which was ligated with a BamHI/EcoRI digest of pBS-ER(C term) (kindly provided by Dr. Kurata, DNAX Institute Palo Alto Calif.)(Kurata et al., 1999) and a XhoI/EcoRI digest of pBS-SK$^+$ to create ΔCA- or ΔWT-STAT5b-ER. A XhoI/NotI digest of LZRS-CA-STAT5b-IRES-ΔNGFR or LZRS-WT-STAT5b-IRES-ΔNGFR was then ligated to a partial NotI/XhoI digest of pBS ΔCA-STAT5b-ER or ΔWT-STAT5b-ER to create LZRS-CA-STAT5b-ER and LZRS-WT-STAT5b-ER. Using this, we made a construct with CA-STAT5b-ER or WT-STAT5b-ER downstream of IRES and ΔNerve Growth Factor Receptor (ΔNGFR), a signaling-incompetent mutant of the NGFR, kindly provided by Dr. C. Bonini (Bonini et al., 1997) or the green fluorescent protein GFP. A monoclonal antibody against NGFR (Chromaprobe, Mountain View, Calif.) was used to visualize ΔNGFR-expressing cells.
Retroviral Transduction The recombinant human fibronectin fragments CH-296 transduction procedure (RetroNectin™; Takara, Otsu, Japan) was performed as described previously (Heemskerk et al., 1997; Heemskerk et al., 1999). Non-tissue culture-treated 24 wells plates (Costar, Badhoevedorp, Netherlands) were coated with 0.3 ml of 30 µg/ml recombinant human fibronectin fragment CH-296 at room temperature for 2 hours or overnight at 40° C. The CH-296 solution was removed, followed by incubation with 2% human serum albumin (HSA) in phosphate buffered saline (PBS) for 30 min at room temperature, followed by washing once with PBS. 5×10$^5$ B cells were plated in 0.25 ml complete medium mixed with 0.25 ml of thawed retroviral supernatant and polybrene (final concentration 4 µg/ml) and incubated for 6 hours at 37° C. Next, 0.25 ml of supernatant was removed and 0.25 ml of fresh retroviral supernatant plus polybrene was added and incubated at 37° C. overnight. The next morning, cells were washed and transferred to 24 wells tissue culture treated plate (Costar) with irradiated (80 Gy) CD40L (CD154) expressing L cells (CD40L-L), IL-2 (20 U/ml) and IL-4 (50 ng/ml).

Cell Culture

B cells were cultured in complete medium at 37° C. in humidified air containing 5% $CO_2$. CD40L-L cells, 80 Gray irradiated, were seeded $5 \times 10^4$ cells per well in 24 wells tissue culture treated plates (Costar). $5 \times 10^4$ sorted B cells were added together with IL-2 (20 U/ml) and IL-4 (50 ng/ml). After one week the cells were used for retroviral transduction. After transduction B cells were cultured again with irradiated CD40L-L cells, IL-2 and IL-4.

Immunohistological Staining for pTyr-STAT5 and CD20

Immunohistological analysis of pTyr-STAT5 and CD20 on human tonsil tissues, obtained from children undergoing tonsillectomy, was performed using immunofluorescence and CLSM analysis as described previously, with minor modifications (Vyth-Dreese et al., 1995). Briefly, formalin fixed, paraffin embedded human tonsil sections, upon citrate retrieval, were pre-incubated in 5% (v/v) normal goat serum (Central Laboratory of the Netherlands Red Cross Blood Transfusion Service (CLB), Amsterdam, The Netherlands). Subsequently, sections were incubated in rabbit anti-pTyr-STAT5b antibody (Cell Signaling Technology, Beverly, Mass., USA) and mouse anti-CD20 (L26, DAKO) at 4° C. overnight, followed by incubations in biotinylated goat anti-rabbit IgG (DAKO), streptavidin/biotin-conjugated horseradish peroxidase complex (ABC-protocol, DAKO) and Tyramide-Alexa Fluor 568 (Molecular Probes Europe, Leiden, The Netherlands). CD20 was visualized using Alexa Fluor 633-conjugated goat anti-mouse IgG (Molecular Probes). In between incubations, sections were rinsed extensively in PBS containing 1% bovine serum albumin (BSA, Sigma Aldrich, Zwijndrecht, The Netherlands). Within each test, isotype matched control antibodies and normal rabbit IgG were included as negative controls. Confocal fluorescence images were obtained on a Leica TCS SP (Leica Microsystems, Heidelberg, Germany) confocal system, equipped with a Kr/HeNe laser combination. Images were taken using a $40 \times 1.25$ NA objective. Color photomicrographs were taken from electronic overlays.

To localize STAT5 expression, CA-STAT5b-ER-IRES-ΔNGFR transduced B cells were attached on polylysine coated coverslips. After fixation with 3.7% formaldehyde at RT for 15 min, cells were permeablized with 0.1% Triton X-100 for 45 sec. Primary antibodies were mouse anti-NGFR and rabbit anti-ER (MC-20, Santa Cruz Biotechnology, Santa Cruz, Calif.). Secondary antibodies were anti-mouse-FITC (Becton Dickinson Pharmingen, Heidelberg, Germany) and anti-Rabbit-TexasRed (Molecular probes, Eugene, Oreg.). Confocal fluorescence images were obtained on a Leica TCS SP (Leica).

Phenotyping of B Cells

Antibodies against the human molecules IgD, IgG, CD3, CD19, CD20, CD27, CD38, CD40, CD45, CD56, CD70, CD80, CD86, HLA-DR (Becton Dickinson, Pharmingen) directly labeled with FITC, PE, or APC and IgM, kappa light chain, lambda light chain, CD138, directly labeled with PE (DAKO) were used for flow cytometry analysis. Stained cells were analyzed using a FACSCalibur™ (Becton Dickinson Immunocytometry systems, San Jose, Calif.) and FACS data was processed with CellQuest™ computer software (Becton Dickinson Immunocytometry systems).

RT-PCR

Total RNA was isolated from thawed pellets with the RNeasy® mini kit (Qiagen Sciences, Germantown, Md.). RNA was reverse transcribed in a volume of 20 µL, containing 5× first strand buffer, 500 µM dNTP's, 25 µg/L Oligo (dT), 200 U superscript II RT (Life Technologies). One microliter of cDNA solution was subjected to PCR in a 50 µl solution containing 20 mM Tris-HCL, 50 mM KCL, 1.5 mM $MgCl_2$, 5 mM dNTP's, 2.5 U Taq DNA polymerase (Life Technologies), and 30 µmol of each primer. PCR conditions were as follows: 7 min denaturing step at 94° C. followed by 30 cycles of 30 sec at 94° C., 30 sec at 62° C. (HPRT), 52° C. (LMP-1), 58° C. (EBNA1/2), 58° C. (BCL-6) and 30 sec at 72° C., and a final 7 min extension at 72° C. The oligonucleotides used for reverse transcriptase (RT) PCR were:

```
                                     (SEQ ID NO: 2)
HPRT forward,    5'-TATGGACAGGACTGAACGTCTTGC-3', (SEQ ID NO: 3)
HPRT reverse,    5'-GACACAAACATGATTCAAATCCCTGA-3', (SEQ ID NO: 4)
LMP-1 forward,   5'-GCGACTCTGCTGGAAATGAT-3', (SEQ ID NO: 5)
LMP-1 reverse,   5'-GACATGGTAATGCCTAGAAG-3', (SEQ ID NO: 6)
EBNA1/2 forward, 5'-AGCAAGAAGAGGAGGTGGTAAG-3', (SEQ ID NO: 7)
EBNA1/2 reverse, 5'-GGCTCAAAGTGGTCTCTAATGC-3', (SEQ ID NO: 8)
BCL-6 forward,   5'-AAGGGTCTGGTTAGTCCACAG-3', (SEQ ID NO: 9)
BCL-6 reverse,   5'-GGTCACACTTGTAGGGTTTGTC-3'.
```

PCR conditions to detect $V_H$ genes were similar as described (Guikema et al., 1999; von Lindern et al., 2000), involving a 7 min denaturing step at 94° C. followed by 35 cycles of 1 min at 94° C., 1 min at 60° C. and 1 min at 72° C., and a final 10 min extension at 72° C. The oligonucleotides used for RT-PCR were as follows:

```
                                     (SEQ ID NO: 10)
VH1/7 forward, 5'-TCTGGGGCTGAGGTGAAGAA-3', (SEQ ID NO: 11)
VH2 forward,   5'-ACCTTGAAGGAGTCTGGTCCT-3', (SEQ ID NO: 12)
VH3 forward,   5'-GGGGGTCCCTGAGACTCTC-3'

(SEQ ID NO: 13)
VH4 forward,   5'-GCCCAGGACTGGTGAAGC-3', (SEQ ID NO: 14)
VH5 forward,   5'-CTGGTGCAGTCTGGAGCAG-3', (SEQ ID NO: 15)
Cµ reverse,    5'-GAGGATCCGGGTGCTGCTGATGTCAGA-3', (SEQ ID NO: 16)
Cγ reverse,    5'-GGGTCTAGACAGGCAGCCCAGGGCCGCTGTG
               C-3'.
```

Western Blotting

Cell extracts were prepared in RIPA lysis buffer (150 mM NaCl, 1% NP-40, 0.1% SDS, 0.5% DOC, 50 mM TRIS-HCl pH 8.0) supplemented with a protease inhibitor cocktail (Boehringer Ingelheim B V, Ingelheim, Germany). Proteins were transferred to Protran nitrocellulose transfer membranes (Schleicher and Schuell BioScience Inc., Keene, N.H.). Primary antibodies conjugated to horse radish peroxidase (HRP) used for Western blotting were BCL-6 (C-19), STAT5b (C-17), ER (MC-20) and actin (1-19) all from Santa Cruz Biotechnology (Santa Cruz, Calif., USA). For the detection of the STAT5 knock down western, equal amounts of protein were loaded using a Bradford test (BCA protein assay reagent kit (Pierce Biotechnology Inc., Rockford, Ill., USA). For the other Western blots, actin was used as a loading control. Detection of proteins was done using enhanced chemiluminescence (Pierce).

Luciferase Reporter Transactivation Assay

Cotransfection of the reporter construct, the constitutively active *Renilla reniformis* luciferase-producing vector prL-CMV (Promega, San Luis Obispo, Calif., USA), and the expression vector LZRS in 293T cells was done with the Fugene transfection reagent in accordance with the manufacturer's instructions (Roche, Basel, Switzerland). Detection of the firefly (*P. pyralis*) and *R. reniformis* luciferases was done using the Dual Luciferase assay kit according to manufacturer's instructions (Promega). The BCL-6 promoter region −657/+471 in the pGL3 basic vector was kindly provided by Dr. S. Hirosawa (Tokyo Medical and Dental University, Tokyo, Japan). Mutations of the STAT5 binding site in the BCL-6 promoter fragments were generated by a two-step PCR approach. The first-step PCR was performed with the BCL-6(F) or BCL-6(R) primer and the corresponding GLprimer2 and RVprimer4 (Promega). BCL-6(F), 5'-GAA-CATGTCTCTAAAGTGCAGGA-3' (SEQ ID NO:17); BCL-6(R), 5'-TCCTGCACTTTAGAGACATGTTC-3' (SEQ ID NO:18). Corresponding PCR products were then purified, mixed and reamplified using the GLprimer2 and RVprimer4 primers. The amplified PCR fragments were cloned directly into the pCR2·1TOPO vector (Invitrogen, Leek, The Netherlands), according to the manufacturers instructions. Sequencing with primers M13(F) and M13(R) was performed with an ABI sequencer (Perkin Elmer Corp, Norwalk, Conn.) using the dye-terminator cycle-sequencing kit (Perkin Elmer). The mutated BCL-6 promoter region was subcloned in pGL3 through SacI and BglII digestion.

Results

Figure 16:
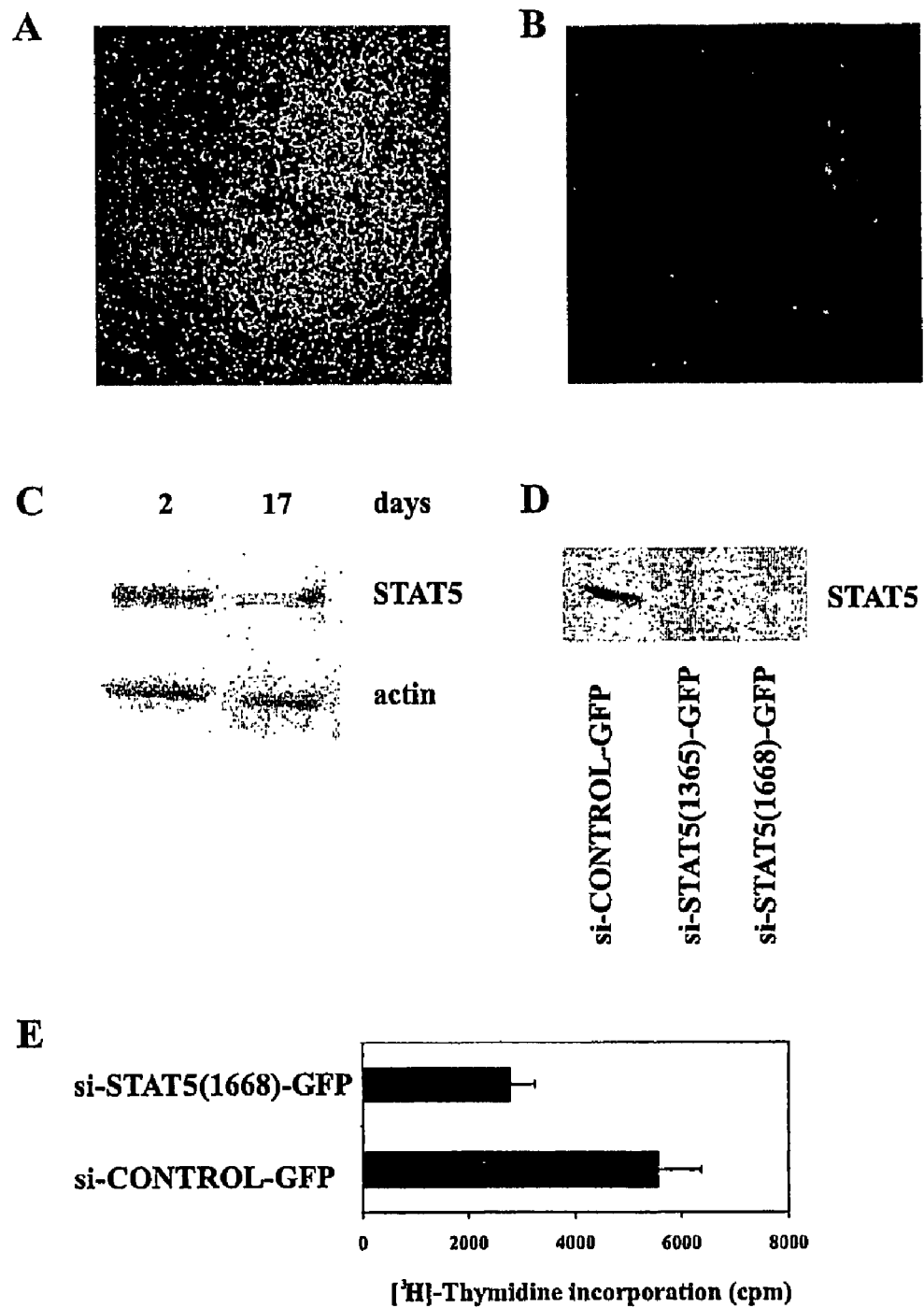
FIG. 16. Detection of STAT5 in human B cells in vivo and in vitro. (A) Formalin fixed, paraffin embedded tonsil tissue was doublestained for pTyr-STAT5 (green) and CD20 (red) as outlined in the Methods section of example 3. In the germinal center, co-localization of pTyr-STAT5 and CD20 is observed on B cells in dark and light zone areas, observable as a patched, membrane-like staining pattern. (B) Doublestained isotype control staining. Results are representative for 3 experiments. Original magnification×800. (C) Human B cells were cultured for the indicated time on CD40L-L cells with IL-2 and IL-4, and total cell lysates were analyzed by Western blot analysis for the levels of STAT5 protein. The blot was stripped and reprobed with an antibody against actin to confirm equal loading of the lanes. (D) Knock down efficiency of siRNA probes (1365 and 1668) specifically targeting the STAT5 mRNA. The Raji B cell line was transduced with either pSIN-control-GFP, pSIN-siSTAT5(1365)-GFP, or pSIN-siSTAT5(1668)-GFP. Total cell lysates of GFP$^+$ cells were analyzed for STAT5 protein expression. Equal loading was assured after protein measurement using the Bradford test. (E) Proliferative response of human B cells transduced with either pSIN-control-GFP or pSIN-siSTAT5(1668)-GFP. GFP$^+$ B cells were sorted and cultured in duplo in a 96-well plate with CD40L-L cells, IL-2 and IL-4 for 3 days, of which the last 18 hours in the presence of (Chan et al.)-Thymidine (1μ Ci/well). Incorporation of (Chan et al.)-Thymidine is expressed as counts per minute (cpm).

Tyrosine Phosphorylated STAT5 is Expressed in Germinal Center B Cells in Human Tonsils Since STAT5 is activated by several B cell growth factors in vitro, we investigated whether tyrosine phosphorylated (pTyr)-STAT5 could be detected under physiological conditions in human tonsils. We performed a CLSM analysis of tonsil sections costained for pTyr-STAT5 and CD20. FIG. 16A clearly shows co-localization of pTyr-STAT5 on $CD20^{dim}$ B cells in germinal center areas, showing a typically patched, membrane-like staining pattern. A similar staining pattern was detectable on T cells in the T cell areas of the tonsil (data not shown). Tonsil sections double-stained with isotype control antibodies did not show any staining (FIG. 16B).

Knocking Down STAT5 by RNA Interference Inhibits Proliferation of Human B Cells

Human B cells can be cultured in vitro for only a limited period following engagement of CD40 in the presence of cytokines, including IL-2, IL-4 and IL-10. The reason why the B cells die after several weeks is incompletely understood. Here we address whether the amount of STAT5 protein is a limiting factor, which may cause nonresponsiveness to growth factors. Human $CD19^+$ B cells were sorted and cultured on CD40L-L cells together with IL-2 and IL-4. Samples were taken after 2 and 17 days of culture, and Western blotting was performed on total cell lysates using a STAT5 antibody. Clearly, STAT5 protein levels were reduced in the B cells after 17 days of culture as compared to 2 days of culture (FIG. 16C). This shows that the B cells eventually die because of limited STAT5 levels.

To directly investigate the role of STAT5 in proliferation of B cells, we chose to knockdown STAT5 levels by specifically targeting STAT5 for degradation by RNA interference. STAT5 siRNA probes (1365 and 1668) were designed and tested for their knockdown efficiency in Raji B cells endogenously expressing STAT5. The STAT5 siRNAs were subcloned in our self-inactivating retroviral construct which also includes the GFP marker driven by the PGK promoter (pSIN GFP). Raji B cells were retrovirally transduced with either the STAT5(1365) or STAT5(1668) siRNA expressing viruses, or a control virus and sorted based on GFP expression. As shown in FIG. 16D, the STAT5(1668) siRNA very efficiently reduced the amount of STAT5 protein expression near to completion compared to control transduced Raji cells, while STAT5(1365) siRNA was less efficient, but also significantly reduced STAT5 levels. To analyze the effect of STAT5 on B cell proliferation, we transduced the STAT5(1668) siRNA probe, in parallel with the control virus, into $CD19^+$ sorted peripheral blood B cells, and cultured these on CD40L-L with IL-2 and IL-4. After sorting the $GFP^+$ B cells, they were cultured in duplo ($10^4$ cells/well) on CD40L-L cells, IL-2 and IL-4 for 3 days, of which the last 18 hours in the presence of (Chan et al.)-Thymidine (1µ Ci/well). It is clear that inhibiting STAT5 protein expression dramatically reduced the proliferative capacity of the B cells by 50% (FIG. 16E).

Effect of STAT5 on the Expansion of Primary Human B Cells

Figure 17:
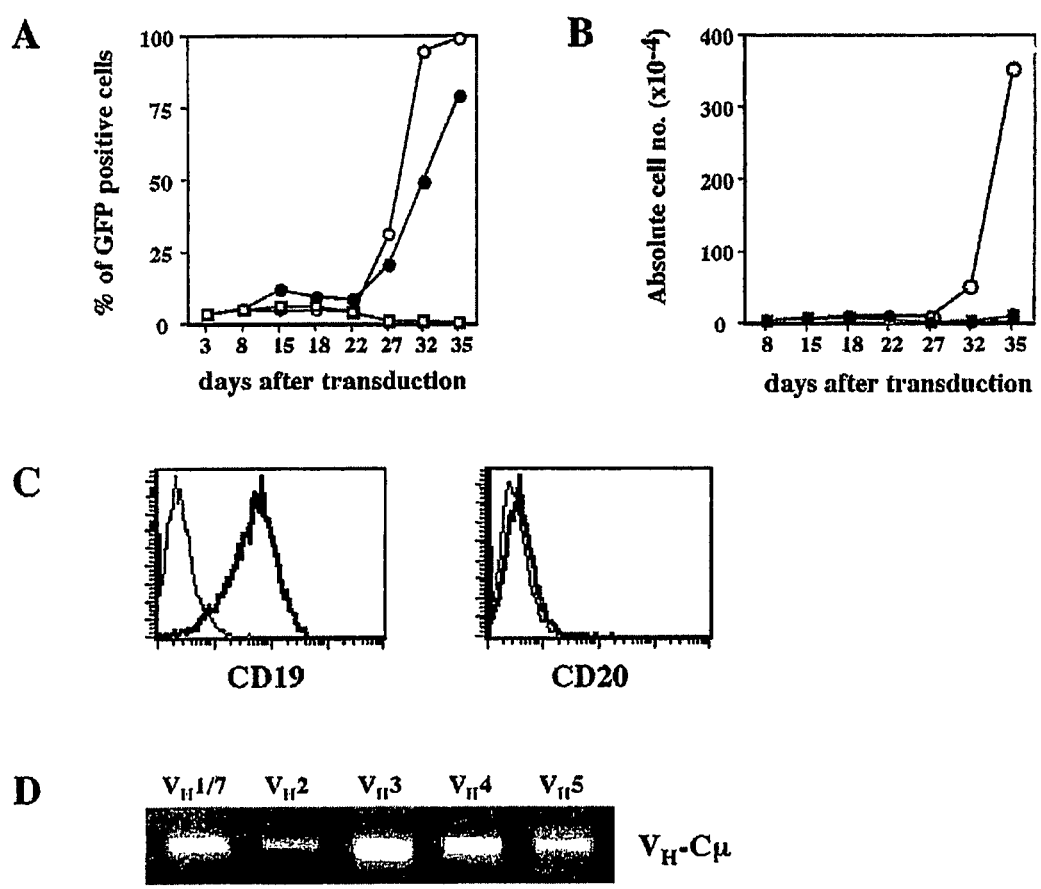
FIG. 17 Expression of CA-STAT5b leads to survival and expansion of B cells, while expression of WT-STAT5b results in survival only. (A) CD19$^+$ B cells were sorted from tonsil, cultured with CD40L, IL-2 and IL-4 and transduced with control-IRES-GFP (open squares), WT-STAT5b-IRES-GFP (closed circles) or CA-STAT5b-IRES-GFP (open circles) and cultured further with CD40L, IL-2 and IL-4. Shown are percentages of GFP$^+$ cells as determined by flow cytometric analysis at the indicated time points. Shown is a representative experiment out of 3. (B) Absolute cell number counts were determined based on the percentages of GFP$^+$ cells determined in (A); control-IRES-GFP (open squares), WT-STAT5b-IRES-GFP (closed circles) or CA-STAT5b-IRES-GFP (open circles). (C) Expression of CD19 and CD20 (bold lines) compared to isotype matched control antibody stainings (thin lines) on CA-STAT5b-IRES-GFP transduced B cells cultured for 3 months in CD40L, IL-2 and IL-4 as determined by flow cytometric analysis. (D) RT-PCR analysis of V$_H$-C□ gene recombinations in CA-STAT5b-IRES-GFP transduced B cells cultured for 3 months in CD40L, IL-2 and IL-4.

The following observations prompted us to examine the role of STAT5 in regulation of growth of human B cells: 1) pTyr-STAT5 can be detected in human B cells in vivo; 2) STAT5 protein levels decline in human B cells cultured in vitro on CD40L-L cells, IL-2 and IL-4, which may correlate with their eventual death; 3) Knockdown of STAT5 in human B cells reduces their proliferative capacity; 4) pTyr-STAT5 is constitutively expressed in various B cell malignancies. We compared the effects of wild type (WT) and constitutive active (CA) mutants of STAT5a and b on the growth of human B cells. Purified tonsil $CD19^+$ B cells were cocultured with CD40L-L cells, IL-2 and IL-4. At day 7, the cells were transduced with virus expressing CA-STAT5a-IRES-GFP, CA-STAT5b-IRES-GFP, WT-STAT5b-IRES-GFP or with control-IRES-GFP. Transduction efficiencies were 5%-20% (data not shown). The percentages of $GFP^+$ cells in the cultures transduced with CA-STAT5b-GFP (FIG. 17A) or CA-STAT5a-GFP (not shown) increased over time. At week 5-6, the control-IRES-GFP transduced and the untransduced B cells started to die, while at week 6 (i.e. 5 weeks after transduction) more than 95% of the CA-STAT5b-GFP transduced cultures were $GFP^+$ and continued to expand, and were kept in culture. B cells transduced with WT-STAT5b-GFP selectively survived but did not expand (FIGS. 17A and B), indicating that activation of STAT5 is suitable for expansion of B cells. The expanded CA-STAT5b-$GFP^+$ B cells expressed CD19, but not CD20 (FIG. 17C). To ensure that the replicative life-span extension of CA-STAT5b-GFP transduced cells was not due to EBV transformation we analyzed LMP-1 and EBNA1/2 mRNAs by a sensitive RT-PCR and confirmed that these genes were not expressed (results not shown). Importantly, the CA-STAT5b-GFP transduced B cells expressed several IgH variable gene segments joined to Cµ (FIG. 17D) or Cgamma (not shown) as determined by RT-PCR, indicating that the transduced B cell lines were not monoclonal.

Together these data show that constitutive expression of active STAT5 rescue in vitro cultured human B cells from cell death, and extend their replicative life span.

Figure 18:
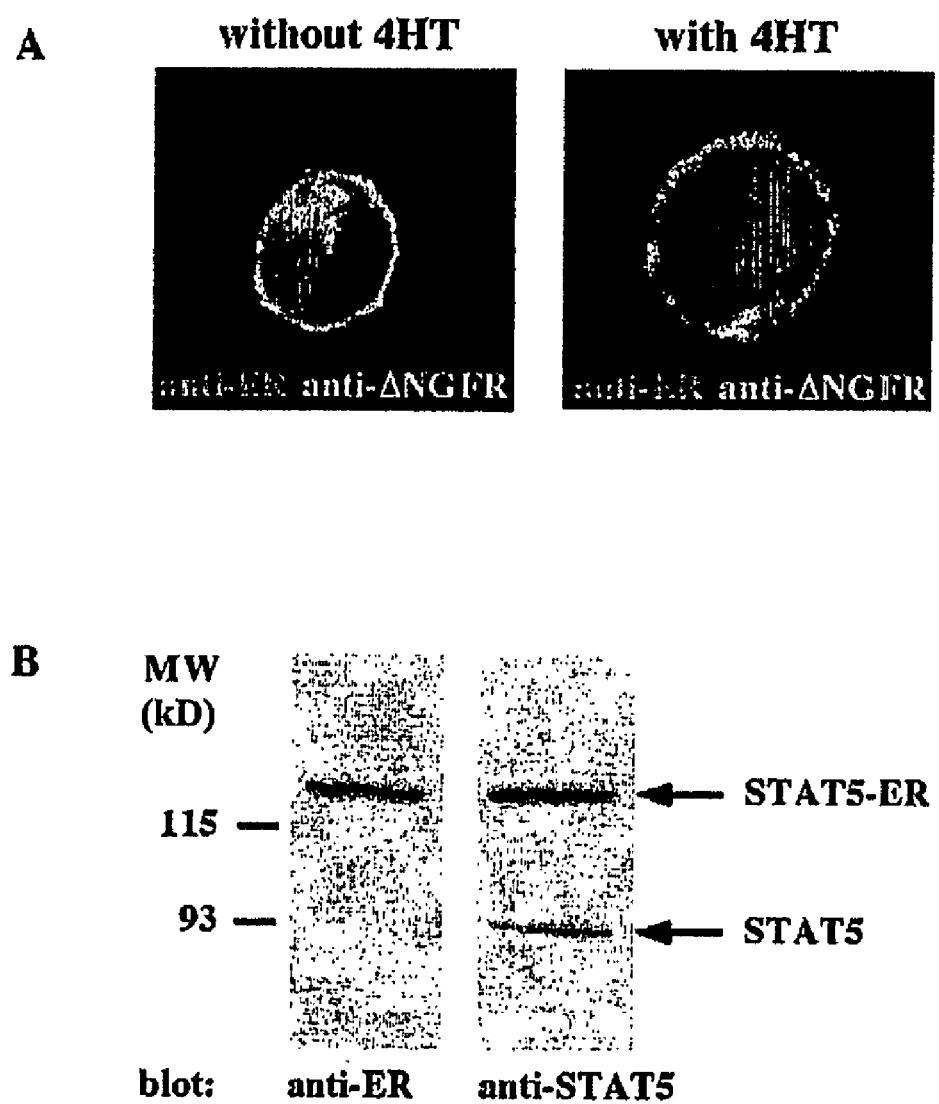
FIG. 18. CA-STAT5b-ER localizes to the nucleus in a 4HT dependent way. (A) B cells transduced with CA-STAT5b-ER-IRES-ΔNGFR were stained with anti-NGFR-FITC (green) and anti-ER-TexasRed (red) in the absence (left panel) or presence (right panel) of 4HT and analyzed by Confocal Laser Scan Microscopy. (B) Western blot analysis of cellular extracts of CA-STAT5b-ER-IRES-ΔNGFR$^+$ B cells using an antibody against STAT5 (right) or ER (left).

Generation of B Cell Lines Following Induction of CA-STAT5B-Er Expression with Tamoxifen To further confirm that only constitutive activation of STAT5b and not a secondary transforming event leads to an extended proliferative response of human B cells, we examined the effect of a regulatable STAT5b construct on B cell proliferation. To this end, we prepared a fusion of the estrogen receptor (ER) with the CA-STAT5b or WT-STAT5b and made a recombinant viral construct harboring CA-STAT5b-ER or WT-STAT5b-ER upstream of IRES-ΔNGFR, which is a truncated, signaling incompetent mutant of the nerve growth factor receptor (Bonini et al., 1997). Upon transduction, the STAT5b-ER fusion protein is expressed in the cytoplasm of the transduced cells as an inactive complex sequestered by heat shock proteins. After incubation with 4-Hydroxy-Tamoxifen (4HT) the ER-fusion protein dissociates from the heat shock proteins and translocates to the nucleus. Indeed, staining of the CA-STAT5b-ER-IRES-ΔNGFR$^+$ B cells with an anti-ER antibody in the absence or presence of 4HT and analysis using CLSM illustrates that CA-STAT5b localizes to the nucleus as expected in a 4HT dependent manner (FIG. 18A). Western blot analysis confirmed the presence of the fusion protein of the expected MW in the transduced cells (FIG. 18B).

Figure 19:
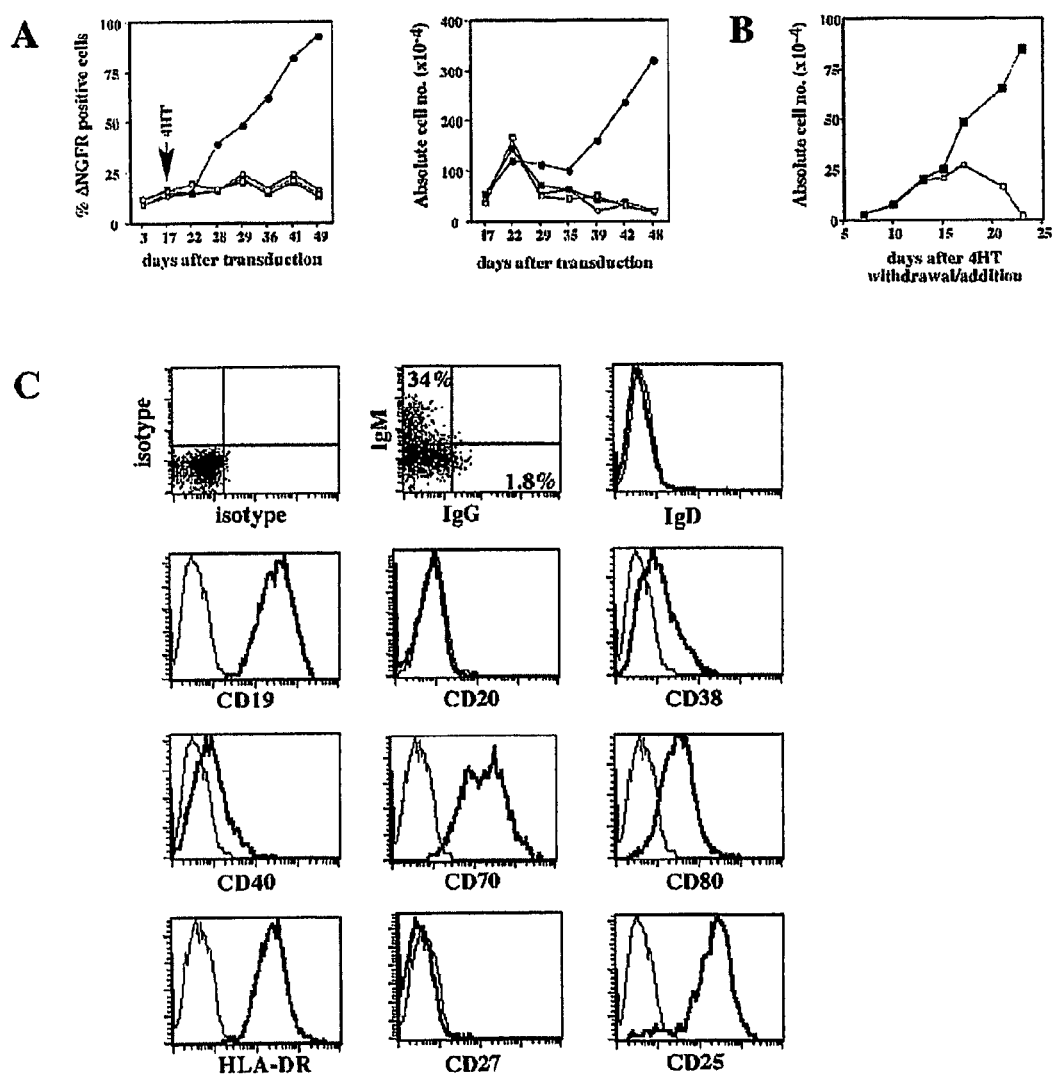
FIG. 19. Characteristics of B cells transduced with CA-STAT5b-ER. (A) Tonsil B cells were cultured in CD40L, IL-2 and IL-4 and transduced with CA-STAT5b-ER-IRES-ΔNGFR (circles) or with control-IRES-ΔNGFR (squares). Both cultures were split, one part was cultured without (open symbols) and another with 1 μM 4HT (closed symbols). At the indicated time points after transduction percentages of transduced cells were determined by flow cytometric analysis after staining with an APC-conjugated antibody against NGFR. Absolute cell number counts were determined based on the percentages of ΔNGFR$^+$ cells. The experiment shown is representative for 5 independent experiments performed. (B) CA-STAT5b-ER-IRES-ΔNGFR transduced B cells 30 days after transduction were cultured for 7 days in the absence of 4HT. Equal numbers of cells were cultured then either in the presence (closed squares) or absence of 4HT (open squares) and absolute cell numbers were determined. Shown is a representative experiment out of 3. (C) Flow cytometric analysis of a representative culture of CA-STAT5b-ER-IRES-ΔNGFR transduced B cells cultured in CD40L, IL-2 and IL-4 in the presence of 4HT. Isotype control stainings are shown as thin histograms.

We then transduced human tonsillar B cells with the CA-STAT5b-ER-IRES-ΔNGFR construct and examined the effect of 4HT on the proliferative capacity of these B cells. FIG. 19A shows that, following culture of tonsillar B cells transduced with CA-STAT5b-ER-IRES-ΔNGFR in CD40L, IL-2 and IL-4, a growth selection of CA-STAT5b-ER expressing cells (ΔNGFR$^+$) only occurred in the presence of 4HT. Importantly, removal of 4HT from CA-STAT5b-ER-IRES-ΔNGFR$^+$ transduced cells resulted in termination of the growth of the B cells and eventual death (FIG. 19B). The CA-STAT5b-ER-IRES-ΔNGFR$^+$ B cells cultured with CD40L, IL-2 and IL-4 cultured in the absence of 4HT initially proliferated, but they ceased to grow and then died after 7-20 days. When 4HT was added back after 7 days, the cells survived and then continued to grow (FIG. 19B). These results demonstrate that CA-STAT5b-induced growth of the tonsil B cells is not a consequence of irreversible genetic changes induced by CA-STAT5b transforming the B cells, but is only dependent on continued functional expression of CA-STAT5b in the nucleus. Part of the tonsil B cells transduced with CA-STAT5b-ER-IRES-ΔNGFR and cultured in CD40L, IL-2, IL-4 and 4HT for 3 months expressed cell surface IgM (FIG. 19C). The cells were negative for cell surface IgD and a small percentage (1-2%) expressed IgG, which lacked IgM. Strikingly, upon prolonged culture of the CA-STAT5b-ER-IRES-ΔNGFR$^+$ B cells expression of cell surface Ig was lost (data not shown). Similar effects were observed after introduction of STAT5 into either naïve or memory peripheral blood B cells (data not shown). Furthermore, the CA-STAT5b-ER-IRES-ΔNGFR$^+$ B cells expressed CD19, CD38, CD40, CD70, CD80 and HLA-DR, but were negative for CD20 and CD27. CD25 was highly expressed on these cells (FIG. 19C), consistent with the fact that STAT5b directly controls CD25 (IL-2Ralpha) transcription (John et al., 1996; John et al., 1999). Noteworthy, expression of the WT-STAT5b-ER fusion protein in B cells resulted in a similar 4HT-dependent growth effect and phenotype compared to expression of the CA-STAT5b-ER protein in B cells (data not shown). Presumably, this is caused by the fact that the ER domains dimerize as has been found for STAT6-ER (Kurata et al., 1999), creating STAT5b-ER dimers that are translocated to the nucleus.

Figure 20:
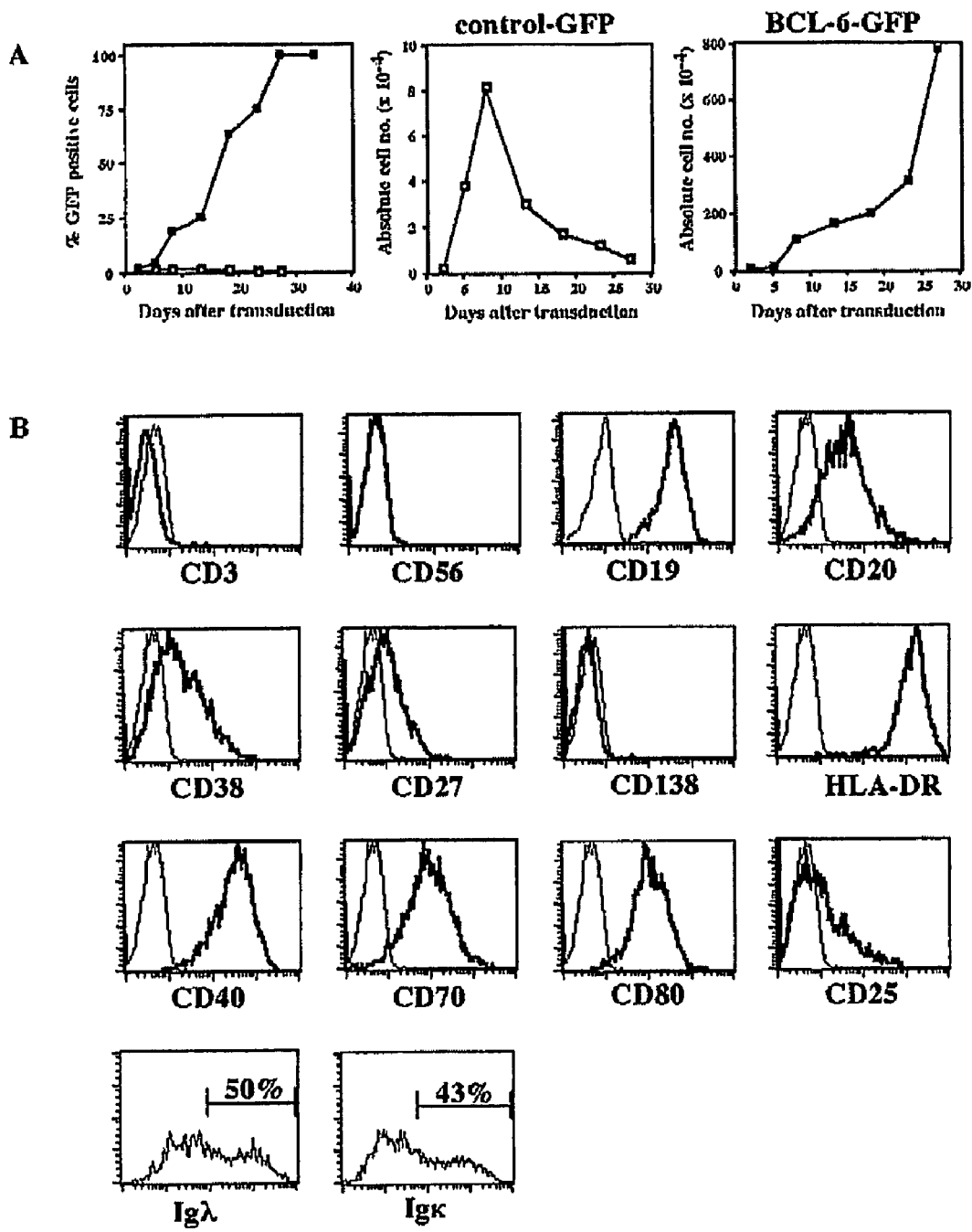
FIG. 20. Characteristics of peripheral B cells transduced with BCL-6-IRES-GFP and expanded in CD40L, IL-2 and IL-4. (A) Flow cytometric analysis of GFP expression and absolute cell number counts of peripheral blood B cells transduced with control-IRES-GFP (open symbol) or BCL-6-IRES-GFP (closed symbol) and cultured in CD40L, IL-2 and IL-4 for the indicated periods of time. This experiment is representative for 8 independent experiments performed. (B) Phenotype of BCL-6-transduced B cells of a representative experiment cultured in CD40L, IL-2 and IL-4 for 77 days after transduction as determined by flow cytometric analysis. Thin histogram lines represent isotype control stainings.

Ectopic Expression of BCL-6 into Human Peripheral Blood B Cells Results in Extension of the Replicative Life Span of the Cells Recently, we reported that ectopic expression of BCL-6 in human tonsil B cells of young children resulted in a growth advantage of B cells when cultured in CD40L, IL-2 and IL-4 (Shvarts et al., 2002). These cells expressed CD19 and were negative for CD3 and CD56. To extend these findings, we investigated whether BCL-6 also affects the proliferative capacity of adult peripheral blood B cells. Therefore, we introduced BCL-6-IRES-GFP into human B cells cultured with CD40L expressing L cells, IL-2 and IL-4. FIG. 20A shows that expression of BCL-6 resulted in a growth advantage of the peripheral B cells expressing the marker GFP starting 10-13 days after transduction of BCL-6. To obtain information about the phenotype of these cells, we performed an extensive analysis with a panel of monoclonal antibodies. FIG. 20B shows that BCL-6-IRES-GFP transduced B cells expressed CD19. In addition, the BCL-6-IRES-GFP transduced B cells expressed CD20, were weakly positive for CD38 and the memory B cell marker CD27, but were negative for the plasma cell marker CD138. Furthermore, the cells expressed the activation markers HLA-DR, CD40, CD70, and CD80, and were weakly positive for CD25. Importantly, the BCL-6-IRES-GFP transduced B cells expressed cell surface Ig kappa or lambda, consistent with the fact that these cells are arrested in their differentiation into cell surface Ig-negative plasma cells.

BCL-6 is a Direct Target of STAT5b

Figure 21:
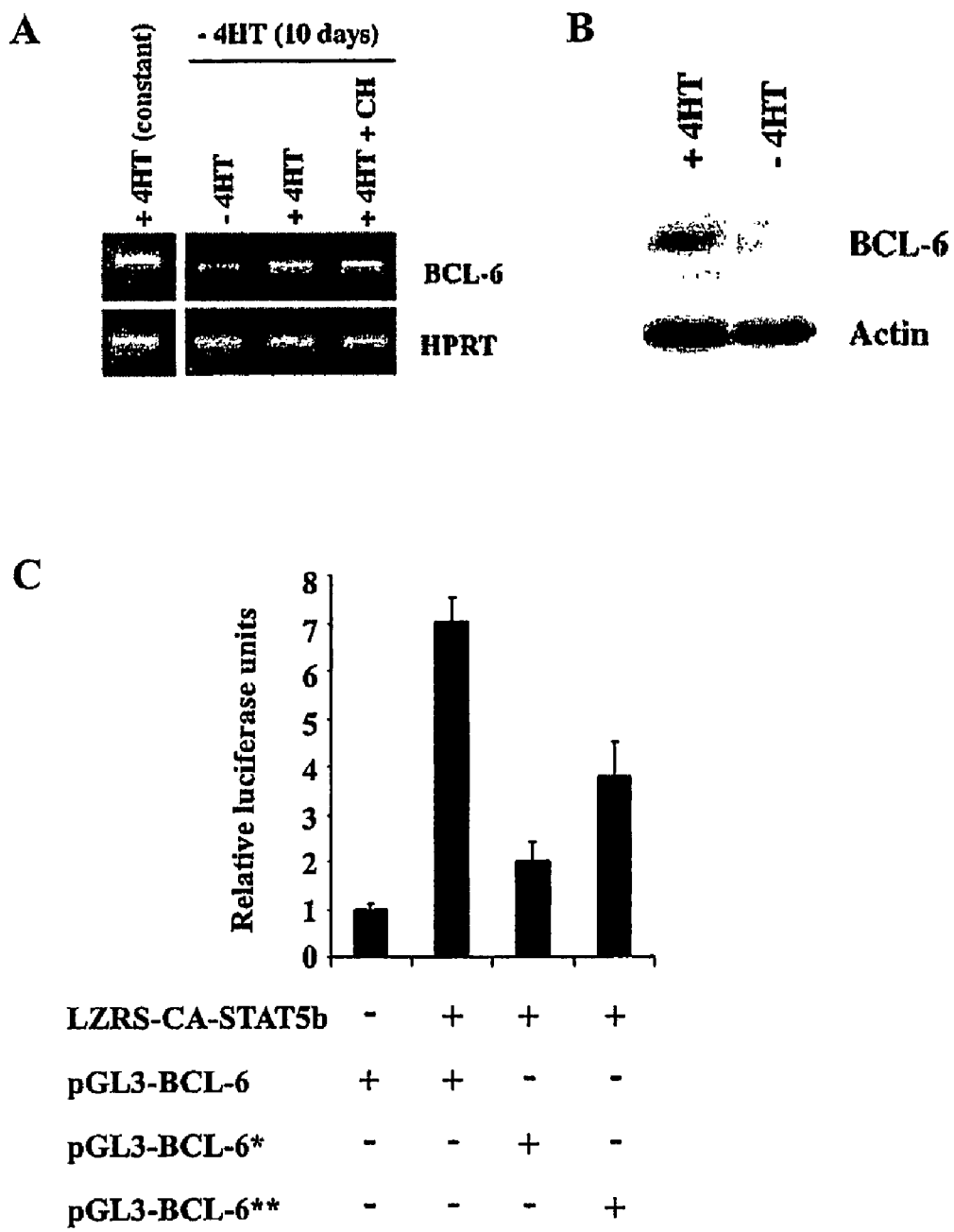
FIG. 21. Induction of BCL-6 expression by STAT5. (A) RT-PCR analysis of BCL-6 and HPRT in B cells transduced with CA-STAT5b-ER cultured in CD40L, IL-2 and IL-4 with 4HT. After incubation of the cells without 4HT for 10 days, 4HT was added back for 8 hr in the presence or absence of cyclohexamide (CH). This experiment was repeated 3 times with similar results. (B) Expression of BCL-6 protein in CA-STAT5b-ER-transduced B cells cultured in the presence of 4HT constantly or absence of 4HT for 12 days as determined by Western blot analysis using an anti-BCL-6 antibody. An antibody against actin was used as a protein loading control. Similar results were obtained in 3 independent experiments. (C) Dual luciferase reporter assay. Part of the promoter region of the BCL-6 gene (position −657/+471 bp) was linked to the firefly (*P. pyralis*) luciferase coding sequence and subcloned into the pGL3 vector. One potential STAT5 binding site in this promoter region (−548/−566 bp) was mutated from TTCTCTGAA to GTCTCTAAA, and two different clones (BCL-6* and BCL-6**) were subcloned into the pGL3-firefly luciferase backbone. These pGL3 constructs were cotransfected with LZRS-CA-STAT5b and the *Renilla* luciferase containing vector into 293T cells. Both luciferase activities were measured sequentially from a single sample and relative luciferase units were calculated and corrected for the *Renilla* luciferase activity.

The observation that CA-STAT5 and BCL-6 have similar effects on the growth of human B cells raises the possibility that BCL-6 is in fact regulated by STAT5. This notion is supported by the fact that the 1.5 kB promoter of BCL-6 (Ohashi et al., 1995) contains three potential STAT binding sites. To study whether STAT5b is able to regulate BCL-6 expression we cultured STAT5b-ER$^+$ tonsil B cells in the absence of 4HT for 10 days. Then, 4HT was added back and the cells were harvested 8 hr later and tested for expression of BCL-6 by RT-PCR. FIG. 21A shows that expression of the BCL-6 transcript is substantially higher in the culture with 4HT than in the culture without this hormone. Western blot analysis revealed that the B cells cultured in the presence of 4HT expressed significantly more BCL-6 protein than the cells cultured in the absence of 4HT (FIG. 21B). To determine whether BCL-6 is a direct or indirect target of STAT5b, the protein synthesis inhibitor cyclohexamide (CH) was added together with 4HT for 8 hr. Upregulation of BCL-6 mRNA was still observed when both 4HT and CH were added (FIG. 21A), while addition of CH alone did not affect BCL-6 expression (data not shown). These data indicate that BCL-6 expression is directly affected by STAT5b.

To extend this observation and to verify that BCL-6 is indeed a direct target of STAT5b, we performed a luciferase reporter gene assay using the BCL-6 promoter. Inspection of the BCL-6 promoter revealed the presence of three potential STAT5 binding sites: TTCTCAGAA at position 1863-1871 bp, TTCTCTGAA at position 1190-1198 bp, and TTCTCTGAA at position 548-556 bp. In addition, one potential STAT5 binding site is located in the noncoding first exon. To determine whether STAT5 was able to activate transcription through the BCL-6 promoter, we used a construct containing part of a BCL-6 promoter (−657/+471) and the noncoding first exon linked to the luciferase coding sequence. This construct harbors the one potential STAT5 binding site most proximal to the startcodon (−548/−556 bp) and the one within the non-coding first exon. This reporter construct was transfected into 293T cells together with a vector expressing CA-STAT5b or a control vector. Cotransfection of the reporter construct and CA-STAT5b led to an increased luciferase activity (FIG. 21C). To show that this increase in reporter activity was dependent on STAT5 activity, mutations were generated in the (−548/−556 bp) STAT5-binding site. We mutated the first STAT5-binding site in the BCL-6 promoter region from TTCTCTGAA to GTCTCTAAA. Mutation of this STAT5-binding site strongly impaired reporter activity when CA-STAT5b was cotransfected (FIG. 21C). These data clearly demonstrate the (−548/−556 bp) STAT5b binding site in the BCL-6 promotor is functional. Together, our results show that STAT5 directly regulates BCL-6 expression.

Figure 22:
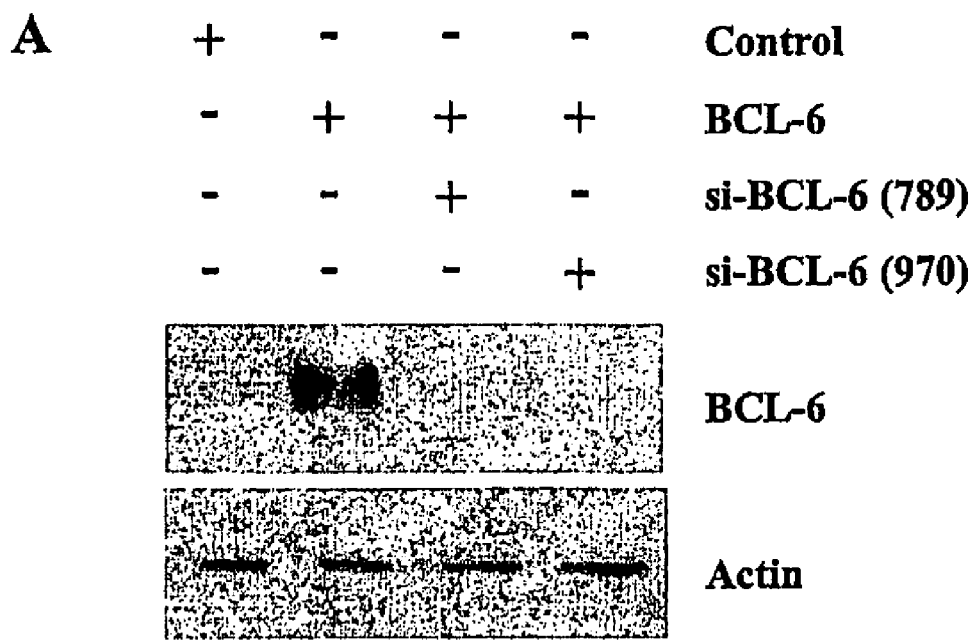
FIG. 22. Effect of BCL-6 knock down on the growth of CA-STAT5b transduced B cells. (A) The knock down efficiency of BCL-6 siRNA probes was tested after transfection into BCL-6 transduced 293T cells by Western blot analysis. After stripping, the blot was incubated with an antibody against actin to assure equal protein loading. (B) Flow cytometric analysis of GFP expression in CA-STAT5b-ER—ΔNGFR+ B cells transduced with control-GFP (open circles), siBCL-6(789)-GFP (closed squares), or siBCL-6(970)-GFP (closed diamonds) and cultured in CD40L, IL-2 and IL-4 for the indicated periods of time. This experiment was repeated in B cells from 4 different donors with similar results.
Figure 22:
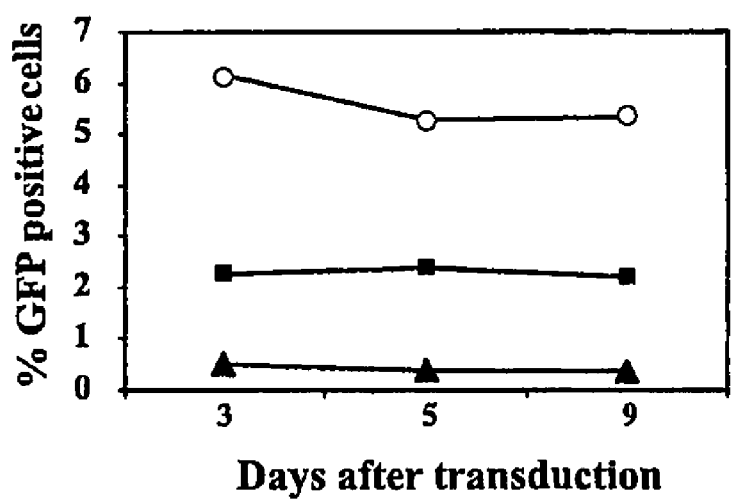

Prolonged Lifespan of CA-STAT5 B Cells does not Exclusively Depend on BCL-6 Expression To determine whether the BCL-6 protein is crucial for the STAT5b-ER prolonged lifespan, we designed two BCL-6 siRNA probes, which were cloned into pSUPER. First, to determine the knock down efficiency of the BCL-6 siRNAs, the pSUPER constructs were cotransfected with a vector expressing BCL-6 in 293T cells. As shown in FIG. 22A, both siBCL-6(789) and siBCL-6(970) probes very efficiently reduced the amount of BCL-6 protein. Both BCL-6 siRNAs were subcloned into the pSIN-GFP retroviral vector, and virus was produced to transduce CA-STAT5b-ER-ΔNGFR$^+$ B cells. The percentage of GFP$^+$ cells in the control-transduced cells was stable over time. The same observation was made for either of the two BCL-6 siRNAs transduced CA-STAT5b-ER-ΔNGFR$^+$ B cells (FIG. 22B), suggesting that CA-STAT5b-ER$^+$ B cells do not depend on BCL-6 for their survival. Strikingly, CD80 expression was 1.5-2 fold increased after BCL-6 knock down in CA-STAT5b-ER-ΔNGFR$^+$ B cells (data not shown). This confirmed the efficacy of the BCL-6 knock down constructs, since CD80 has been described to be directly repressed by BCL-6 (Niu et al., 2003). Our findings demonstrate that BCL-6 is not the sole mediator of the effect of STAT5b on the replicative lifespan of B cells.

REFERENCES

Ariyoshi, K., Nosaka, T., Yamada, K., Onishi, M., Oka, Y., Miyajima, A., and Kitamura, T. (2000). Constitutive activation of STAT5 by a point mutation in the SH2 domain. J Biol Chem 275, 24407-24413

Barry, S. C. et al. Lentivirus vectors encoding both central polypurine tract and posttranscriptional regulatory element provide enhanced transduction and transgene expression. Hum Gene Ther 12, 1103-8 (2001).

Bonini, C., Ferrari, G., Verzeletti, S., Servida, P., Zappone, E., Ruggieri, L., Ponzoni, M., Rossini, S., Mavilio, F., Traversari, C., and Bordignon, C. (1997). HSV-TK gene transfer into donor lymphocytes for control of allogeneic graft-versus-leukemia. Science 276, 1719-1724

Brummelkamp, T. R., Bernards, R., and Agami, R. (2002). A system for stable expression of short interfering RNAs in mammalian cells. Science 296, 550-553

Guikema, J. E., Vellenga, E., Veeneman, J. M., Hovenga, S., Bakkus, M. H., Klip, H., and Bos, N. A. (1999). Multiple myeloma related cells in patients undergoing autologous peripheral blood stem cell transplantation. Br J Haematol 104, 748-754

Heemskerk, M. H., Blom, B., Nolan, G., Stegmann, A. P., Bakker, A. Q., Weijer, K., Res, P. C., and Spits, H. (1997). Inhibition of T cell and promotion of natural killer cell development by the dominant negative helix loop helix factor Id3. J Exp Med 186, 1597-1602

Heemskerk, M. H., Hooijberg, E., Ruizendaal, J. J., van der Weide, M. M., Kueter, E., Bakker, A. Q., Schumacher, T. N., and Spits, H. (1999). Enrichment of an antigen-specific T cell response by retrovirally transduced human dendritic cells. Cell Immunol 195, 10-17

John, S., Robbins, C. M., and Leonard, W. J. (1996). An IL-2 response element in the human IL-2 receptor alpha chain promoter is a composite element that binds Stat5, Elf-1, HMG-I(Y) and a GATA family protein. Embo J 15, 5627-5635

John, S., Vinkemeier, U., Soldaini, E., Darnell, J. E., and Leonard, W. J. (1999). The significance of tetramerization in promoter recruitment by Stat5. Mol Cell Biol 19, 1910-1918

Kaplan, M. H., Schindler, U., Smiley, S. T., and Grusby, M. J. (1996). Stat6 is required for mediating responses to IL-4 and for development of Th2 cells. Immunity 4, 313-319.

Kinsella, T. M., and Nolan, G. P. (1996). Episomal vectors rapidly and stably produce high-titer recombinant retrovirus. Human Gene Therapy 7, 1405-1413

Kurata, H., Lee, H. J., O'Garra, A., and Arai, N. (1999). Ectopic expression of activated Stat6 induces the expression of Th2-specific cytokines and transcription factors in developing Th1 cells. Immunity 11, 677-688

Leonard, W. J., and O'Shea, J. J. (1998). Jaks and STATs: biological implications. Annu Rev Immunol 16, 293-322.

Lischke, A., Moriggl, R., Brandlein, S., Berchtold, S., Kammer, W., Sebald, W., Groner, B., Liu, X., Hennighausen, L., and Friedrich, K. (1998). The interleukin-4 receptor activates STAT5 by a mechanism that relies upon common gamma-chain. J Biol Chem 273, 31222-31229.

Niu, H., Cattoretti, G., and Dalla-Favera, R. (2003). BCL6 controls the expression of the B7-1/CD80 costimulatory receptor in germinal center B cells. J Exp Med 198, 211-221

Onishi, M., Nosaka, T., Misawa, K., Mui, A. L., Gorman, D., McMahon, M., Miyajima, A., and Kitamura, T. (1998). Identification and characterization of a constitutively active STAT5 mutant that promotes cell proliferation. Mol Cell Biol 18, 3871-3879

Reljic, R., Wagner, S. D., Peakman, L. J., and Fearon, D. T. (2000). Suppression of signal transducer and activator of transcription 3-dependent B lymphocyte terminal differentiation by BCL-6. J Exp Med 192, 1841-1848.

Rolling, C., Treton, D., Pellegrini, S., Galanaud, P., and Richard, Y. (1996). IL4 and IL13 receptors share the gamma c chain and activate STAT6, STAT3 and STAT5 proteins in normal human B cells. FEBS Lett 393, 53-56.

Scheeren, F. A., Naspetti, M., Diehl, S., Schotte, R., Nagasawa, M., Wijnands, E., Gimeno, R., Vyth-Dreese, F. A., Blom, B., and Spits, H. (2005). STAT5 regulates the self-renewal capacity and differentiation of human memory B cells and controls Bcl 6 expression. Nature Immunology. Vol 6, No. 3, 303-313.

Seppen, J, Rijnberg, M., Cooreman, M. P., and Oude Elferink, R. P. (2002). Lentiviral vectors for efficient transduction of isolated primary quiescent hepatocytes. J Hepatol 36, 459-65.

Shimoda, K., van Deursen, J., Sangster, M. Y., Sarawar, S. R., Carson, R. T., Tripp, R. A., Chu, C., Quelle, F. W., Nosaka, T., Vignali, D. A., et al. (1996). Lack of IL-4-induced Th2 response and IgE class switching in mice with disrupted Stat6 gene. Nature 380, 630-633.

Shvarts, A., Brummelkamp, T., Scheeren, F., Koh, E., Daley, G. Q., Spits, H., and Bernards, R. (2002). A senescence rescue screen identifies BCL6 as an inhibitor of anti-proliferative p19ARF— p53 signaling. Genes Dev in press Strathdee, C. A., McLeod, M. R. & Hall, J. R. Efficient control of tetracycline-responsive gene expression from an autoregulated bi-directional expression vector. Gene 229, 21-29 (1999).

Teglund, S., McKay, C., Schuetz, E., van Deursen, J. M., Stravopodis, D., Wang, D., Brown, M., Bodner, S., Grosveld, G., and Ihle, J. N. (1998). Stat5a and Stat5b proteins have essential and nonessential, or redundant, roles in cytokine responses. Cell 93, 841-850.

Traggiai E, Chicha L, Mazzucchelli L, bronz L, Piffaretti J-C, lanzavecchia A, Manz M. Development of a human adaptive immune system in cord blood cell-transplanted mice.

Verhoef, K., Marzio, G., Hillen, W., Bujard, H. & Berkhout, B. Strict control of human immunodeficiency virus type 1 replication by a genetic switch: Tet for Tat. J Virol 75, 979-87 (2001).

Von Lindern, M., Amelsvoort, M. P., van Dijk, T., Deiner, E., van Den Akker, E., van Emst-De Vries, S., Willems, P., Beug, H., and Lowenberg, B. (2000). Protein kinase C alpha controls erythropoietin receptor signaling. J Biol Chem 275, 34719-34727

Vyth-Dreese, F. A., Dellemijn, T. A., Majoor, D., and de Jong, D. (1995). Localization in situ of the co-stimulatory molecules B7.1, B7.2, CD40 and their ligands in normal human lymphoid tissue. Eur J Immunol 25, 3023-3029

Weijer K, Uittenbogaart C H, Voordouw A, Couwenberg F, Seppen J, Blom B, Vyth-Dreese F A, Spits H. Intrathymic and extrathymic development of human plasmacytoid dendritic cell precursors in vivo. Blood (2002). 99:2752-2759

Ye, B. H., Cattoretti, G., Shen, Q., Zhang, J., Hawe, N., de Waard, R., Leung, C., Nouri-Shirazi, M., Orazi, A., Chaganti, R. S., et al. (1997). The BCL-6 proto-oncogene controls germinal-centre formation and Th2-type inflammation. Nat Genet. 16, 161-170.

---

The invention claimed is:

1. A method for producing antibodies specifically directed towards an antigen of interest, the method comprising:
   providing a stem cell and/or a precursor cell of a B cell with a nucleic acid sequence which, when present and expressed in a B cell, is capable of stabilizing said B cell;
   providing a non-human animal with said stem cell and/or precursor cell;
   providing said non-human animal with said antigen of interest;
   allowing generation of a B cell which is capable of producing antibodies specifically directed towards said antigen of interest;
   obtaining said B cell;
   culturing said B cell ex vivo after it has been obtained from said animal; and
   harvesting antibodies produced by said B cell,
   wherein said nucleic acid sequence in an inactive state during in vivo differentiation of said stem cell and/or precursor cell into a B cell, and
   wherein said nucleic acid sequence is at least in part activated during the ex vivo culturing of the B cell, thereby stabilizing the B cell.

2. A method according to claim 1 wherein said precursor cell is a human CD34$^+$ precursor cell.

3. A method according to claim 1, wherein said precursor cell is provided with at least a functional part of a gene encoding a CA STAT protein and/or BCL 6, and/or with a nucleic acid sequence capable of at least in part inactivating p53 expression.

4. The method according to claim 1, wherein said non-human animal is a mouse.

5. The method according to claim 4, wherein said mouse is a RAG2$^{-/-}$ γc$^{-/-}$ mouse.

6. A method for producing antibodies specifically directed towards an antigen of interest, the method comprising:
   transducing a stem cell and/or a precursor cell of a B cell, with a nucleic acid sequence that, when expressed in a B cell, stabilizes said B cell, and wherein said nucleic acid sequence is under control of a promoter;
   growing said transduced cell in a non-human animal;

providing said non-human animal with the antigen of interest;

in vivo differentiating said transduced cell into a B cell in the non-human animal, wherein the nucleic acid sequence in said transduced cell is in an inactive state during said in vivo differentiation, and wherein the resulting B cell is able to produce antibodies specifically directed towards the antigen of interest;

obtaining the resulting B cell from the non-human animal;

culturing the thus obtained B cell ex vivo, wherein expression of the nucleic acid sequence in said B cell is activated to stabilize said B cell via said promoter; and harvesting antibodies produced by the B cell.

* * * * *

SEQUENCE LISTING

```
<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: p53 targeting sequence

<400> SEQUENCE: 1
gactccagtg gtaatctac                                                  19

<210> SEQ ID NO 2
<211> LENGTH: 24
<212> TYPE: DNA
<213> ORGANISM: Artificial Sequence
<220> FEATURE:
<223> OTHER INFORMATION: HPRT forward oligonucleotide

<400> SEQUENCE: 2
tatggacagg actgaacgtc ttgc                                            24

<210> SEQ ID NO 3
<211> LENGTH: 26
<212> TYPE: DNA
<213> ORGANISM: Artificial Sequence
<220> FEATURE:
<223> OTHER INFORMATION: HPRT reverse oligonucleotide

<400> SEQUENCE: 3
gacacaaaca tgattcaaat ccctga                                          26

<210> SEQ ID NO 4
<211> LENGTH: 20
<212> TYPE: DNA
<213> ORGANISM: Artificial Sequence
<220> FEATURE:
<223> OTHER INFORMATION: LMP-1 forward oligonucleotide

<400> SEQUENCE: 4
gcgactctgc tggaaatgat                                                 20

<210> SEQ ID NO 5
<211> LENGTH: 20
```

```
<212> TYPE: DNA
<213> ORGANISM: Artificial Sequence
<220> FEATURE:
<223> OTHER INFORMATION: LMP-1 reverse oligonucleotide

<400> SEQUENCE: 5
gacatggtaa tgcctagaag                                                    20

<210> SEQ ID NO 6
<211> LENGTH: 22
<212> TYPE: DNA
<213> ORGANISM: Artificial Sequence
<220> FEATURE:
<223> OTHER INFORMATION: EBNA1/2 forward oligonucleotide

<400> SEQUENCE: 6
agcaagaaga ggaggtggta ag                                                 22

<210> SEQ ID NO 7
<211> LENGTH: 22
<212> TYPE: DNA
<213> ORGANISM: Artificial Sequence
<220> FEATURE:
<223> OTHER INFORMATION: EBNA1/2 reverse oligonucleotide

<400> SEQUENCE: 7
ggctcaaagt ggtctctaat gc                                                 22

<210> SEQ ID NO 8
<211> LENGTH: 21
<212> TYPE: DNA
<213> ORGANISM: Artificial Sequence
<220> FEATURE:
<223> OTHER INFORMATION: BCL-6 forward oligonucleotide

<400> SEQUENCE: 8
aagggtctgg ttagtccaca g                                                  21

<210> SEQ ID NO 9
<211> LENGTH: 22
<212> TYPE: DNA
<213> ORGANISM: Artificial Sequence
<220> FEATURE:
<223> OTHER INFORMATION: BCL-6 reverse oligonucleotide

<400> SEQUENCE: 9
ggtcacactt gtagggtttg tc                                                 22

<210> SEQ ID NO 10
<211> LENGTH: 20
<212> TYPE: DNA
<213> ORGANISM: Artificial Sequence
<220> FEATURE:
<223> OTHER INFORMATION: VH1/7 forward oligonucleotide

<400> SEQUENCE: 10
tctggggctg aggtgaagaa                                                    20

<210> SEQ ID NO 11
<211> LENGTH: 21
<212> TYPE: DNA
<213> ORGANISM: Artificial Sequence
<220> FEATURE:
<223> OTHER INFORMATION: VH2 forward oligonucleotide

<400> SEQUENCE: 11
accttgaagg agtctggtcc t                                                  21
```

<210> SEQ ID NO 12
<211> LENGTH: 19
<212> TYPE: DNA
<213> ORGANISM: Artificial Sequence
<220> FEATURE:
<223> OTHER INFORMATION: VH3 forward oligonucleotide

<400> SEQUENCE: 12
gggggtccct gagactctc                                              19

<210> SEQ ID NO 13
<211> LENGTH: 18
<212> TYPE: DNA
<213> ORGANISM: Artificial Sequence
<220> FEATURE:
<223> OTHER INFORMATION: VH4 forward oligonucleotide

<400> SEQUENCE: 13
gcccaggact ggtgaagc                                               18

<210> SEQ ID NO 14
<211> LENGTH: 19
<212> TYPE: DNA
<213> ORGANISM: Artificial Sequence
<220> FEATURE:
<223> OTHER INFORMATION: VH5 forward oligonucleotide

<400> SEQUENCE: 14
ctggtgcagt ctggagcag                                              19

<210> SEQ ID NO 15
<211> LENGTH: 27
<212> TYPE: DNA
<213> ORGANISM: Artificial Sequence
<220> FEATURE:
<223> OTHER INFORMATION: Cmu reverse oligonucleotide

<400> SEQUENCE: 15
gaggatccgg gtgctgctga tgtcaga                                     27

<210> SEQ ID NO 16
<211> LENGTH: 32
<212> TYPE: DNA
<213> ORGANISM: Artificial Sequence
<220> FEATURE:
<223> OTHER INFORMATION: Cgamma reverse oligonucleotide

<400> SEQUENCE: 16
gggtctagac aggcagccca gggccgctgt gc                               32

<210> SEQ ID NO 17
<211> LENGTH: 23
<212> TYPE: DNA
<213> ORGANISM: Artificial Sequence
<220> FEATURE:
<223> OTHER INFORMATION: BCL-6 forward oligonucleotide primer

<400> SEQUENCE: 17
gaacatgtct ctaaagtgca gga                                         23

<210> SEQ ID NO 18
<211> LENGTH: 23
<212> TYPE: DNA
<213> ORGANISM: Artificial Sequence
<220> FEATURE:
<223> OTHER INFORMATION: BCL-6 reverse oligonucleotide primer

```
<400> SEQUENCE: 18
tcctgcactt tagagacatg ttc                                             23

<210> SEQ ID NO 19
<211> LENGTH: 19
<212> TYPE: DNA
<213> ORGANISM: Artificial Sequence
<220> FEATURE:
<223> OTHER INFORMATION: Region of STAT5

<400> SEQUENCE: 19
gcagcagacc atcatcctg                                                  19

<210> SEQ ID NO 20
<211> LENGTH: 19
<212> TYPE: DNA
<213> ORGANISM: Artificial Sequence
<220> FEATURE:
<223> OTHER INFORMATION: Region from STAT5

<400> SEQUENCE: 20
gacccagagg aagtttgca                                                  19

<210> SEQ ID NO 21
<211> LENGTH: 19
<212> TYPE: DNA
<213> ORGANISM: Artificial Sequence
<220> FEATURE:
<223> OTHER INFORMATION: Region from BCL-6

<400> SEQUENCE: 21
tgtgtgccac agcaatatc                                                  19

<210> SEQ ID NO 22
<211> LENGTH: 19
<212> TYPE: DNA
<213> ORGANISM: Artificial Sequence
<220> FEATURE:
<223> OTHER INFORMATION: Region from BCL-6

<400> SEQUENCE: 22
gatgagattg ccctgcatt                                                  19
```